US010208095B2

(12) United States Patent
Leach et al.

(10) Patent No.: US 10,208,095 B2
(45) Date of Patent: *Feb. 19, 2019

(54) METHODS FOR MAKING CYTOKINE COMPOSITIONS FROM TISSUES USING NON-CENTRIFUGAL METHODS

(71) Applicant: Biomet Biologics, LLC, Warsaw, IN (US)

(72) Inventors: Michael D. Leach, Warsaw, IN (US); Jennifer E. Woodell-May, Warsaw, IN (US); Joel C. Higgins, Claypool, IN (US); Krista O'Shaughnessey, Pierceton, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/839,280

(22) Filed: Mar. 15, 2013

(65) Prior Publication Data

US 2014/0274894 A1 Sep. 18, 2014

(51) Int. Cl.
A61K 38/18 (2006.01)
B01D 11/02 (2006.01)
B01D 12/00 (2006.01)
B01D 37/00 (2006.01)
C07K 14/435 (2006.01)
C07K 1/34 (2006.01)
A61K 38/17 (2006.01)
A61K 38/19 (2006.01)
A61K 35/14 (2015.01)
A61K 35/28 (2015.01)
A61K 35/35 (2015.01)
C07K 14/52 (2006.01)
A61K 38/20 (2006.01)
C07K 14/545 (2006.01)
G01N 33/50 (2006.01)

(52) U.S. Cl.
CPC ............ C07K 14/435 (2013.01); A61K 35/14 (2013.01); A61K 35/28 (2013.01); A61K 35/35 (2013.01); A61K 38/1793 (2013.01); A61K 38/1808 (2013.01); A61K 38/1841 (2013.01); A61K 38/1858 (2013.01); A61K 38/1866 (2013.01); A61K 38/191 (2013.01); A61K 38/2006 (2013.01); C07K 1/34 (2013.01); C07K 14/52 (2013.01); C07K 14/545 (2013.01); G01N 33/5002 (2013.01); G01N 33/5005 (2013.01)

(58) Field of Classification Search
None
See application file for complete search history.

(56) References Cited

U.S. PATENT DOCUMENTS

| | | |
|---|---|---|
| 593,333 A | 11/1897 | Park |
| 1,468,313 A | 9/1923 | Fritz |
| 1,593,814 A | 7/1926 | Robert |
| 2,722,257 A | 11/1955 | Lockhart |
| 3,013,557 A | 12/1961 | Pallotta |
| 3,141,846 A | 7/1964 | Laven, Jr. |
| 3,159,159 A | 12/1964 | Cohen |
| 3,300,051 A | 1/1967 | Mitchell |
| 3,409,165 A | 11/1968 | Creith |
| 3,420,374 A | 1/1969 | Umeda |
| 3,441,143 A | 4/1969 | Kudiaty |
| 3,469,369 A | 7/1969 | Flodin et al. |
| 3,508,653 A | 4/1970 | Coleman |
| 3,545,671 A | 12/1970 | Ross |
| 3,583,627 A | 6/1971 | Wilson |
| 3,596,652 A | 8/1971 | Winkelman |
| 3,647,070 A | 3/1972 | Adler |
| 3,654,925 A | 4/1972 | Holderith |
| 3,661,265 A | 5/1972 | Greenspan |
| 3,706,305 A | 12/1972 | Berger et al. |
| 3,706,306 A | 12/1972 | Berger et al. |
| 3,723,244 A | 3/1973 | Breillatt |
| 3,741,400 A | 6/1973 | Dick |
| 3,779,383 A | 12/1973 | Ayres |
| 3,785,549 A | 1/1974 | Latham |
| 3,814,248 A | 6/1974 | Lawhead |
| 3,849,072 A | 11/1974 | Ayres |
| 3,850,369 A | 11/1974 | Bull et al. |
| 3,879,295 A | 4/1975 | Glover et al. |
| 3,887,466 A | 6/1975 | Ayres |

(Continued)

FOREIGN PATENT DOCUMENTS

| | | |
|---|---|---|
| AU | 696278 B2 | 9/1998 |
| AU | 748575 B2 | 6/2002 |

(Continued)

OTHER PUBLICATIONS

Wang et al. Cell separation by dielectrophoretic field-flow-fractionation. Analytical Chemistry. 2000; 72(4): 832-839.*
Pommer et al. Dielectrophoretic separation of platelets from whole blood in microfluidic channels. Electrophoresis. 2008; 29:1213-1218.*
Alford, J. et al. "Cartilage Restoration, Part 1" The American Journal of Sports Medicine, vol. 33, No. 2 (2005) p. 295-306.
Anitua, E. et al. "Autologous platelets as a source of proteins for healing and tissue regeneration" Thromb Haemost, vol. 91 (pp. 4-15) 2004.
Anonymous: "Update for veterinarians" Dec. 2012. vet.osu.edu/sites/default/files/documents/pdf/news/vmc/ovmaVeternarianUp/date/20121112.pdf.

(Continued)

Primary Examiner — Vanessa L. Ford
Assistant Examiner — Sandra E Dillahunt
(74) Attorney, Agent, or Firm — Schwegman Lundberg & Woessner, P.A.

(57) ABSTRACT

Non-centrifugal methods for generating a solution rich in interleukin-1 receptor antagonist from a tissue comprising cytokine-producing cells. The solution rich in IL-1ra can also include at least one of sTNF-RI, sTNF-RII, IGF-I, EGF, HGF, PDGF-AB, PDGF-BB, VEGF, TGF-β1, and sIL-1 RII.

26 Claims, 3 Drawing Sheets

(56) References Cited

U.S. PATENT DOCUMENTS

| | | |
|---|---|---|
| 3,894,952 A | 7/1975 | Ayres |
| 3,896,733 A | 7/1975 | Rosenberg |
| 3,897,337 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,937,211 A | 2/1976 | Merten |
| 3,941,699 A | 3/1976 | Ayres |
| 3,945,928 A | 3/1976 | Ayres |
| 3,951,801 A | 4/1976 | Ayres |
| 3,957,654 A | 5/1976 | Ayres |
| 3,962,085 A | 6/1976 | Liston et al. |
| 3,965,889 A | 6/1976 | Sachs |
| 3,972,812 A | 8/1976 | Gresl, Jr. |
| 3,982,691 A | 9/1976 | Schlutz |
| 4,001,122 A | 1/1977 | Griffin |
| 4,020,831 A | 5/1977 | Adler |
| 4,046,699 A | 9/1977 | Zine, Jr. |
| 4,055,501 A | 10/1977 | Cornell |
| 4,059,108 A | 11/1977 | Latham, Jr. |
| 4,066,549 A | 1/1978 | Oeser et al. |
| 4,077,396 A | 3/1978 | Wardlaw et al. |
| 4,088,582 A | 5/1978 | Murty |
| 4,146,172 A | 3/1979 | Cullis et al. |
| 4,152,270 A | 5/1979 | Cornell |
| 4,154,690 A | 5/1979 | Ballies |
| 4,159,896 A | 7/1979 | Levine et al. |
| 4,187,979 A | 2/1980 | Cullis et al. |
| 4,189,385 A | 2/1980 | Greenspan |
| 4,203,840 A | 5/1980 | Stoeppler et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. |
| 4,322,298 A | 3/1982 | Persidsky |
| 4,332,351 A | 6/1982 | Kellogg |
| 4,362,567 A | 12/1982 | Schwarz et al. |
| 4,364,832 A | 12/1982 | Ballies |
| 4,377,572 A | 3/1983 | Schwarz et al. |
| 4,379,849 A | 4/1983 | Heimreid |
| 4,411,794 A | 10/1983 | Schwinn et al. |
| 4,414,976 A | 11/1983 | Schwarz et al. |
| 4,416,654 A | 11/1983 | Schoendorfer |
| 4,417,981 A | 11/1983 | Nugent |
| 4,424,132 A | 1/1984 | Iriguchi |
| 4,427,650 A | 1/1984 | Stroetmann |
| 4,427,651 A | 1/1984 | Stroetmann |
| 4,442,655 A | 4/1984 | Stroetmann |
| 4,443,345 A | 4/1984 | Wells |
| 4,445,550 A | 5/1984 | Davis et al. |
| 4,446,021 A | 5/1984 | Aufderhaar et al. |
| 4,453,927 A | 6/1984 | Sinko |
| 4,453,939 A | 6/1984 | Zimmerman et al. |
| 4,464,167 A | 8/1984 | Schoendorfer |
| 4,511,662 A | 4/1985 | Baran et al. |
| 4,537,767 A | 8/1985 | Rothman et al. |
| RE32,089 E | 3/1986 | Blatt et al. |
| 4,577,514 A | 3/1986 | Bradley et al. |
| 4,610,656 A | 9/1986 | Mortensen |
| 4,617,009 A | 10/1986 | Ohlin |
| 4,627,879 A | 12/1986 | Rose et al. |
| 4,631,055 A | 12/1986 | Redl et al. |
| 4,632,761 A | 12/1986 | Bowers |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger |
| 4,708,799 A | 11/1987 | Gerlach et al. |
| 4,714,457 A | 12/1987 | Alterbaum |
| 4,722,790 A | 2/1988 | Cawley et al. |
| 4,724,317 A | 2/1988 | Brown |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,835 A | 7/1989 | Grande |
| 4,850,952 A | 7/1989 | Figdor et al. |
| 4,853,137 A | 8/1989 | Ersson |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani |
| 4,900,453 A | 2/1990 | Sedlmayer |
| 4,902,281 A | 2/1990 | Avoy |
| 4,909,251 A | 3/1990 | Seelich |
| 4,915,847 A | 4/1990 | Dillon et al. |
| 4,917,801 A | 4/1990 | Luderer et al. |
| 4,928,603 A | 5/1990 | Rose et al. |
| 4,929,242 A | 5/1990 | Desecki et al. |
| 4,933,291 A | 6/1990 | Daiss et al. |
| 4,939,081 A | 7/1990 | Figdor et al. |
| 4,943,273 A | 7/1990 | Pages |
| 4,946,601 A | 8/1990 | Fiehler |
| 4,950,220 A | 8/1990 | Wells et al. |
| 4,957,637 A | 9/1990 | Cornell |
| 4,957,638 A | 9/1990 | Smith |
| 4,973,168 A | 11/1990 | Chan |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'donnell, Jr. |
| 5,019,243 A | 5/1991 | Mcewen et al. |
| 5,024,613 A | 6/1991 | Vasconcellos et al. |
| 5,030,215 A | 7/1991 | Morse et al. |
| 5,030,341 A | 7/1991 | Mcewen et al. |
| 5,039,401 A | 8/1991 | Columbus et al. |
| 5,045,048 A | 9/1991 | Kaleskas |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,075,222 A | 12/1991 | Hannum et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling |
| 5,178,602 A | 1/1993 | Wells |
| 5,185,001 A | 2/1993 | Galanakis |
| 5,188,583 A | 2/1993 | Guigan |
| 5,190,057 A | 3/1993 | Sarfarazi |
| 5,190,759 A | 3/1993 | Lindblad et al. |

(56) References Cited

U.S. PATENT DOCUMENTS

| | | |
|---|---|---|
| 5,197,985 A | 3/1993 | Caplan |
| 5,203,825 A | 4/1993 | Haynes |
| 5,204,537 A | 4/1993 | Bennet et al. |
| 5,206,023 A | 4/1993 | Hunziker |
| 5,207,638 A | 5/1993 | Choksi et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |
| 5,251,786 A | 10/1993 | Sarrine |
| 5,258,126 A | 11/1993 | Pall et al. |
| 5,260,420 A | 11/1993 | Burnouf-radosevich et al. |
| 5,269,927 A | 12/1993 | Fiehler |
| 5,271,852 A | 12/1993 | Luoma, II |
| 5,279,825 A | 1/1994 | Wehling |
| 5,281,342 A | 1/1994 | Biesel et al. |
| 5,290,552 A | 3/1994 | Sierra et al. |
| 5,290,918 A | 3/1994 | Bui-khac |
| 5,298,171 A | 3/1994 | Biesel |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-fogh |
| 5,321,126 A | 6/1994 | Van Dommelen et al. |
| 5,322,620 A | 6/1994 | Brown et al. |
| 5,330,974 A | 7/1994 | Pines et al. |
| 5,344,752 A | 9/1994 | Murphy |
| 5,354,483 A | 10/1994 | Furse |
| 5,359,032 A | 10/1994 | Dayer et al. |
| 5,370,221 A | 12/1994 | Magnusson et al. |
| 5,370,802 A | 12/1994 | Brown |
| 5,372,945 A | 12/1994 | Alchas et al. |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-khac et al. |
| 5,403,272 A | 4/1995 | Deniega et al. |
| 5,405,607 A | 4/1995 | Epstein |
| 5,409,833 A | 4/1995 | Hu et al. |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,474,687 A | 12/1995 | Van Vlasselaer |
| 5,480,378 A | 1/1996 | Weis-fogh et al. |
| 5,484,383 A | 1/1996 | Fitch, Jr. et al. |
| 5,486,359 A | 1/1996 | Caplan et al. |
| 5,494,578 A | 2/1996 | Brown |
| 5,494,592 A | 2/1996 | Latham, Jr. et al. |
| 5,501,371 A | 3/1996 | Schwartz-feldman |
| 5,505,685 A | 4/1996 | Antwiler |
| 5,510,102 A | 4/1996 | Cochrum |
| 5,520,885 A | 5/1996 | Coelho et al. |
| 5,525,477 A | 6/1996 | Hassouna |
| 5,533,518 A | 7/1996 | Vogler |
| 5,560,830 A | 10/1996 | Coleman et al. |
| 5,571,418 A | 11/1996 | Lee et al. |
| 5,575,778 A | 11/1996 | Hardt et al. |
| 5,577,513 A | 11/1996 | Van Vlasselaer |
| 5,585,007 A | 12/1996 | Antanavich et al. |
| 5,588,958 A | 12/1996 | Cunningham et al. |
| 5,589,462 A | 12/1996 | Patat et al. |
| 5,599,558 A | 2/1997 | Gordinier et al. |
| 5,601,711 A | 2/1997 | Sklar et al. |
| 5,601,727 A | 2/1997 | Bormann et al. |
| 5,603,845 A | 2/1997 | Holm |
| 5,607,579 A | 3/1997 | Latham, Jr. et al. |
| 5,614,106 A | 3/1997 | Payrat et al. |
| 5,618,663 A | 4/1997 | Delmas |
| 5,632,895 A | 5/1997 | Tsukagoshi et al. |
| 5,632,905 A | 5/1997 | Haynes |
| 5,641,414 A | 6/1997 | Brown |
| 5,641,622 A | 6/1997 | Lake et al. |
| 5,643,192 A | 7/1997 | Hirsh |
| 5,643,193 A | 7/1997 | Papillon et al. |
| 5,645,540 A | 7/1997 | Henniges et al. |
| 5,646,004 A | 7/1997 | Van Vlasselaer |
| 5,648,223 A | 7/1997 | Van Vlasselaer |
| 5,649,903 A | 7/1997 | Deniega et al. |
| 5,663,051 A | 9/1997 | Vlasselaer |
| 5,674,173 A | 10/1997 | Hlavinka et al. |
| 5,707,331 A | 1/1998 | Wells et al. |
| 5,707,647 A | 1/1998 | Dunn et al. |
| 5,707,876 A | 1/1998 | Levine |
| 5,716,616 A | 2/1998 | Prockop et al. |
| 5,723,331 A | 3/1998 | Tubo et al. |
| 5,724,988 A | 3/1998 | Dennehey et al. |
| 5,733,466 A | 3/1998 | Benebo et al. |
| 5,733,545 A | 3/1998 | Hood, III |
| 5,736,033 A | 4/1998 | Coleman et al. |
| 5,738,784 A | 4/1998 | Holm et al. |
| 5,738,796 A | 4/1998 | Bormann et al. |
| 5,750,025 A | 5/1998 | Holmes et al. |
| 5,750,658 A | 5/1998 | Coelho et al. |
| 5,762,798 A | 6/1998 | Wenthold et al. |
| 5,785,700 A | 7/1998 | Olson |
| 5,786,217 A | 7/1998 | Tubo et al. |
| 5,788,662 A | 8/1998 | Antanavich et al. |
| 5,792,344 A | 8/1998 | Holm |
| 5,792,450 A | 8/1998 | Wilson et al. |
| 5,795,489 A | 8/1998 | Holm |
| 5,795,571 A | 8/1998 | Cederholm-Williams et al. |
| 5,795,751 A | 8/1998 | Apel |
| 5,811,094 A | 9/1998 | Caplan et al. |
| 5,811,151 A | 9/1998 | Hendriks et al. |
| 5,817,519 A | 10/1998 | Zelmanovic et al. |
| 5,823,986 A | 10/1998 | Peterson |
| 5,824,084 A | 10/1998 | Muschler |
| 5,830,359 A | 11/1998 | Knight et al. |
| 5,833,866 A | 11/1998 | Brown |
| 5,834,418 A | 11/1998 | Brazeau et al. |
| 5,837,150 A | 11/1998 | Langley et al. |
| 5,840,502 A | 11/1998 | Van Vlasselaer |
| 5,842,477 A | 12/1998 | Naughton et al. |
| 5,846,427 A | 12/1998 | Kessler et al. |
| 5,853,600 A | 12/1998 | Mcneal et al. |
| 5,860,937 A | 1/1999 | Cohen |
| 5,863,892 A | 1/1999 | Stern et al. |
| 5,865,785 A | 2/1999 | Bischof |
| 5,885,239 A | 3/1999 | Headley et al. |
| 5,889,584 A | 3/1999 | Wardlaw |
| 5,895,346 A | 4/1999 | Wells et al. |
| 5,899,874 A | 5/1999 | Jonsson |
| 5,900,245 A | 5/1999 | Sawhney et al. |
| 5,906,934 A | 5/1999 | Grande et al. |
| 5,916,557 A | 6/1999 | Berlowitz-tarrant et al. |
| 5,916,743 A | 6/1999 | Lake et al. |
| 5,918,622 A | 7/1999 | Perez |
| 5,924,972 A | 7/1999 | Turvaville et al. |
| 5,934,803 A | 8/1999 | Hutter |
| 5,938,621 A | 8/1999 | Kelly et al. |
| 5,951,160 A | 9/1999 | Ronk |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm |
| 5,961,210 A | 10/1999 | Mccardel et al. |
| 5,980,734 A | 11/1999 | Itoh |
| 5,980,757 A | 11/1999 | Brown et al. |
| 5,985,315 A | 11/1999 | Patat et al. |
| 5,997,544 A | 12/1999 | Nies et al. |
| 6,007,811 A | 12/1999 | Sawyer et al. |
| 6,010,627 A | 1/2000 | Hood, III |
| 6,011,490 A | 1/2000 | Tonnesen et al. |
| 6,020,196 A | 2/2000 | Hu et al. |
| 6,022,306 A | 2/2000 | Dumont et al. |
| 6,025,201 A | 2/2000 | Zelmanovic et al. |
| 6,027,655 A | 2/2000 | Holm |

(56) References Cited

U.S. PATENT DOCUMENTS

| | | |
|---|---|---|
| 6,049,026 A | 4/2000 | Muschler |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,096,728 A | 8/2000 | Collins et al. |
| 6,102,843 A | 8/2000 | Kelley et al. |
| 6,117,425 A | 9/2000 | Macphee et al. |
| 6,123,655 A | 9/2000 | Fell |
| 6,150,163 A | 11/2000 | McPherson et al. |
| 6,153,113 A | 11/2000 | Goodrich et al. |
| 6,183,737 B1 | 2/2001 | Zaleske et al. |
| 6,196,987 B1 | 3/2001 | Holmes et al. |
| 6,197,325 B1 | 3/2001 | Macphee et al. |
| 6,200,287 B1 | 3/2001 | Keller et al. |
| 6,200,606 B1 | 3/2001 | Peterson et al. |
| 6,214,338 B1 | 4/2001 | Antanavich et al. |
| 6,221,315 B1 | 4/2001 | Giesler et al. |
| 6,245,900 B1 | 6/2001 | Yamasaki et al. |
| 6,264,890 B1 | 7/2001 | Boehringer et al. |
| 6,274,090 B1 | 8/2001 | Coelho et al. |
| 6,277,961 B1 | 8/2001 | Hock et al. |
| 6,280,400 B1 | 8/2001 | Niermann |
| 6,286,670 B1 | 9/2001 | Smith |
| 6,287,558 B1 | 9/2001 | Lanza et al. |
| 6,296,602 B1 | 10/2001 | Headley |
| 6,316,247 B1 | 11/2001 | Katz et al. |
| 6,322,785 B1 | 11/2001 | Landesberg et al. |
| 6,327,491 B1 | 12/2001 | Franklin et al. |
| 6,328,765 B1 | 12/2001 | Hardwick et al. |
| 6,334,842 B1 | 1/2002 | Hlavinka et al. |
| 6,337,072 B1 | 1/2002 | Ford et al. |
| 6,342,157 B1 | 1/2002 | Hood, III |
| 6,351,659 B1 | 2/2002 | Vilsmeier |
| 6,355,239 B1 | 3/2002 | Bruder et al. |
| 6,368,298 B1 | 4/2002 | Beretta et al. |
| 6,368,498 B1 | 4/2002 | Guilmette |
| 6,398,972 B1 | 6/2002 | Blasetti et al. |
| 6,406,671 B1 | 6/2002 | Dicesare et al. |
| 6,409,528 B1 | 6/2002 | Bodnar |
| 6,410,344 B1 | 6/2002 | Chung |
| 6,417,004 B1 | 7/2002 | Brady et al. |
| 6,440,444 B2 | 8/2002 | Boyce et al. |
| 6,444,228 B1 | 9/2002 | Baugh et al. |
| 6,464,624 B2 | 10/2002 | Pages |
| 6,471,069 B2 | 10/2002 | Lin et al. |
| 6,472,162 B1 | 10/2002 | Coelho et al. |
| 6,487,992 B1 | 12/2002 | Hollis |
| 6,508,778 B1 | 1/2003 | Verkaart et al. |
| 6,516,953 B1 | 2/2003 | Dicesare et al. |
| 6,523,698 B1 | 2/2003 | Dennehey et al. |
| 6,544,162 B1 | 4/2003 | Van et al. |
| 6,544,727 B1 | 4/2003 | Hei |
| 6,558,341 B1 | 5/2003 | Swisher |
| 6,563,953 B2 | 5/2003 | Lin et al. |
| 6,596,180 B2 | 7/2003 | Baugh et al. |
| 6,599,873 B1 | 7/2003 | Sommer et al. |
| 6,623,472 B1 | 9/2003 | Reincke et al. |
| 6,623,959 B2 | 9/2003 | Harris |
| 6,629,919 B2 | 10/2003 | Egozy et al. |
| 6,638,503 B2 | 10/2003 | Chitte |
| 6,641,708 B1 * | 11/2003 | Becker .................. B03C 5/026 204/547 |
| 6,649,072 B2 | 11/2003 | Brandt et al. |
| 6,676,629 B2 | 1/2004 | Andrew et al. |
| 6,713,246 B1 | 3/2004 | Reinecke et al. |
| 6,716,187 B1 | 4/2004 | Jorgensen |
| 6,719,901 B2 | 4/2004 | Dolecek et al. |
| 6,733,471 B1 | 5/2004 | Ericson et al. |
| 6,758,978 B1 | 7/2004 | Bedell |
| 6,759,188 B2 | 7/2004 | Reinecke et al. |
| 6,764,531 B2 | 7/2004 | Hogan |
| 6,777,231 B1 | 8/2004 | Katz et al. |
| 6,790,371 B2 | 9/2004 | Dolecek |
| 6,803,022 B2 | 10/2004 | Dicesare et al. |
| 6,811,777 B2 | 11/2004 | Mishra |
| 6,830,762 B2 | 12/2004 | Baugh et al. |
| 6,835,353 B2 | 12/2004 | Smith et al. |
| 6,835,377 B2 | 12/2004 | Goldberg et al. |
| RE38,730 E | 4/2005 | Jakary et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E | 7/2005 | Jakary et al. |
| 6,979,307 B2 | 12/2005 | Beretta et al. |
| 7,011,644 B1 | 3/2006 | Andrew et al. |
| 7,011,852 B2 | 3/2006 | Sukavaneshvar et al. |
| 7,077,273 B2 | 7/2006 | Ellsworth et al. |
| 7,077,827 B2 | 7/2006 | Greenfield |
| 7,155,288 B2 | 12/2006 | Soykan et al. |
| 7,166,283 B2 | 1/2007 | Tsuji et al. |
| 7,179,391 B2 | 2/2007 | Leach et al. |
| 7,195,606 B2 | 3/2007 | Ballin |
| 7,223,346 B2 | 5/2007 | Dorian et al. |
| 7,273,886 B2 | 9/2007 | Olivero |
| 7,302,882 B2 | 12/2007 | Reuter |
| 7,354,515 B2 | 4/2008 | Coull et al. |
| 7,374,678 B2 | 5/2008 | Leach et al. |
| 7,411,006 B2 | 8/2008 | Shanbrom |
| 7,465,293 B2 | 12/2008 | Reinecke et al. |
| 7,470,371 B2 | 12/2008 | Dorian et al. |
| 7,531,355 B2 | 5/2009 | Rodríguez et al. |
| 7,553,413 B2 | 6/2009 | Dorian et al. |
| 7,608,258 B2 | 10/2009 | Mishra |
| 7,678,385 B2 | 3/2010 | Reddi |
| 7,694,828 B2 | 4/2010 | Swift et al. |
| 7,708,152 B2 | 5/2010 | Dorian et al. |
| 7,806,276 B2 | 10/2010 | Leach et al. |
| 7,845,499 B2 | 12/2010 | Higgins et al. |
| 7,867,765 B2 | 1/2011 | Faustman et al. |
| 7,901,344 B2 | 3/2011 | Yoo |
| 7,901,584 B2 | 3/2011 | Dorian et al. |
| 7,914,689 B2 | 3/2011 | Higgins et al. |
| 7,987,995 B2 | 8/2011 | Dorian et al. |
| 7,992,725 B2 | 8/2011 | Leach et al. |
| 8,048,297 B2 | 11/2011 | Leach et al. |
| 8,048,321 B2 | 11/2011 | Leach et al. |
| 8,062,534 B2 | 11/2011 | Higgins et al. |
| 8,067,534 B2 | 11/2011 | Jagota |
| 8,093,211 B2 | 1/2012 | Tennenbaum et al. |
| 8,202,539 B2 | 6/2012 | Behnam et al. |
| 8,567,609 B2 | 10/2013 | Landrigan et al. |
| 8,596,470 B2 | 12/2013 | Leach et al. |
| 8,753,690 B2 | 6/2014 | Higgins et al. |
| 8,783,470 B2 | 7/2014 | Hecker et al. |
| 8,801,586 B2 | 8/2014 | Dorian et al. |
| 8,808,551 B2 | 8/2014 | Leach et al. |
| 8,950,586 B2 | 2/2015 | Dorian et al. |
| 8,992,862 B2 | 3/2015 | Leach et al. |
| 9,011,800 B2 | 4/2015 | Leach et al. |
| 9,119,829 B2 | 9/2015 | Higgins et al. |
| 9,308,224 B2 | 4/2016 | Higgins et al. |
| 9,556,243 B2 | 1/2017 | Leach et al. |
| 9,701,728 B2 | 7/2017 | Higgins et al. |
| 9,758,806 B2 | 9/2017 | Woodell-May et al. |
| 9,763,875 B2 | 9/2017 | Higgins et al. |
| 9,878,011 B2 | 1/2018 | Landrigan et al. |
| 9,895,418 B2 | 2/2018 | Landrigan et al. |
| 2001/0009757 A1 | 7/2001 | Bischof et al. |
| 2001/0016195 A1 | 8/2001 | Tobinick |
| 2001/0053764 A1 | 12/2001 | Sims et al. |
| 2002/0009454 A1 | 1/2002 | Boone et al. |
| 2002/0032112 A1 | 3/2002 | Pages |
| 2002/0035820 A1 | 3/2002 | Farris |
| 2002/0076400 A1 | 6/2002 | Katz et al. |
| 2002/0077276 A1 | 6/2002 | Fredeking et al. |
| 2002/0082220 A1 | 6/2002 | Hoemann et al. |

(56) References Cited

U.S. PATENT DOCUMENTS

| | | |
|---|---|---|
| 2002/0090711 A1 | 7/2002 | Karlsson |
| 2002/0104808 A1 | 8/2002 | Blasetti et al. |
| 2002/0114775 A1 | 8/2002 | Pathak |
| 2002/0119179 A1 | 8/2002 | Rezania et al. |
| 2002/0161449 A1 | 10/2002 | Muschler |
| 2002/0169408 A1 | 11/2002 | Beretta et al. |
| 2002/0172666 A1 | 11/2002 | Sacchi et al. |
| 2002/0182664 A1 | 12/2002 | Dolecek et al. |
| 2002/0192632 A1 | 12/2002 | Hei et al. |
| 2003/0033021 A1 | 2/2003 | Plouhar et al. |
| 2003/0033022 A1 | 2/2003 | Plouhar et al. |
| 2003/0050709 A1 | 3/2003 | Noth et al. |
| 2003/0050710 A1 | 3/2003 | Petersen et al. |
| 2003/0055511 A1 | 3/2003 | Schryver et al. |
| 2003/0082152 A1 | 5/2003 | Hedrick et al. |
| 2003/0091536 A1 | 5/2003 | Frisbie et al. |
| 2003/0099650 A1 | 5/2003 | Ho et al. |
| 2003/0138910 A1 | 7/2003 | Reinecke et al. |
| 2003/0185803 A1 | 10/2003 | Kadiyala et al. |
| 2003/0191429 A1 | 10/2003 | Andrew et al. |
| 2003/0194397 A1 | 10/2003 | Mishra |
| 2003/0205538 A1 | 11/2003 | Dorian et al. |
| 2004/0005246 A1 | 1/2004 | Efthimiadis et al. |
| 2004/0013575 A1 | 1/2004 | Stevens et al. |
| 2004/0120942 A1 | 6/2004 | McGinnis et al. |
| 2004/0171146 A1 | 9/2004 | Katz et al. |
| 2004/0182395 A1 | 9/2004 | Brookman |
| 2004/0182788 A1 | 9/2004 | Dorian et al. |
| 2004/0182795 A1 | 9/2004 | Dorian et al. |
| 2004/0219182 A1 | 11/2004 | Gomes et al. |
| 2004/0251217 A1 | 12/2004 | Leach et al. |
| 2004/0258671 A1 | 12/2004 | Watkins |
| 2005/0059589 A1 | 3/2005 | Mullarkey |
| 2005/0076396 A1 | 4/2005 | Katz et al. |
| 2005/0084961 A1 | 4/2005 | Hedrick et al. |
| 2005/0084962 A1 | 4/2005 | Simon |
| 2005/0100536 A1 | 5/2005 | Mishra |
| 2005/0109716 A1 | 5/2005 | Leach et al. |
| 2005/0130301 A1 | 6/2005 | Mckay et al. |
| 2005/0145187 A1 | 7/2005 | Gray |
| 2005/0152905 A1 | 7/2005 | Omoigui |
| 2005/0153441 A1 | 7/2005 | Hedrick et al. |
| 2005/0153442 A1 | 7/2005 | Katz et al. |
| 2005/0186120 A1 | 8/2005 | Dorian et al. |
| 2005/0196393 A1 | 9/2005 | Shanbrom |
| 2005/0196874 A1 | 9/2005 | Dorian et al. |
| 2005/0197293 A1 | 9/2005 | Mellis et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0046960 A1 | 3/2006 | McKay et al. |
| 2006/0051865 A1 | 3/2006 | Higgins et al. |
| 2006/0057223 A1 | 3/2006 | DiMauro et al. |
| 2006/0057693 A1 | 3/2006 | Simon |
| 2006/0083720 A1 | 4/2006 | Fraser et al. |
| 2006/0121002 A1 | 6/2006 | Rolland et al. |
| 2006/0140923 A1 | 6/2006 | Evangelista |
| 2006/0151384 A1 | 7/2006 | Ellsworth et al. |
| 2006/0171948 A1 | 8/2006 | Weinstein et al. |
| 2006/0175242 A1 | 8/2006 | Dorian et al. |
| 2006/0175244 A1 | 8/2006 | Dorian et al. |
| 2006/0175268 A1 | 8/2006 | Dorian et al. |
| 2006/0178610 A1 | 8/2006 | Nowakowski |
| 2006/0196885 A1 | 9/2006 | Leach et al. |
| 2006/0243676 A1 | 11/2006 | Swift et al. |
| 2006/0263408 A1 | 11/2006 | Rezania et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0027082 A1 | 2/2007 | Hasty et al. |
| 2007/0034579 A1 | 2/2007 | Dorian et al. |
| 2007/0036768 A1 | 2/2007 | Fraser et al. |
| 2007/0075016 A1 | 4/2007 | Leach |
| 2007/0092494 A1 | 4/2007 | Higgins et al. |
| 2007/0207161 A1 | 9/2007 | Ralph |
| 2007/0208321 A1 | 9/2007 | Leach et al. |
| 2008/0011684 A1 | 1/2008 | Dorian et al. |
| 2008/0019964 A1 | 1/2008 | Olmarker et al. |
| 2008/0064626 A1 | 3/2008 | Zanella |
| 2008/0164204 A1 | 7/2008 | Hatamian et al. |
| 2008/0173593 A1 | 7/2008 | Coull et al. |
| 2008/0193424 A1 | 8/2008 | McKale et al. |
| 2008/0217263 A1 | 9/2008 | Higgins et al. |
| 2008/0217264 A1 | 9/2008 | Leach et al. |
| 2008/0217265 A1 | 9/2008 | Leach et al. |
| 2008/0268064 A1 | 10/2008 | Woodell-May |
| 2008/0269762 A1 | 10/2008 | Simon et al. |
| 2008/0283474 A1 | 11/2008 | Leach et al. |
| 2008/0306431 A1 | 12/2008 | Yoo |
| 2008/0318317 A1 | 12/2008 | Roche et al. |
| 2009/0014391 A1 | 1/2009 | Leach et al. |
| 2009/0018313 A1 | 1/2009 | Shanbrom |
| 2009/0047242 A1 | 2/2009 | Reinecke et al. |
| 2009/0101599 A1 | 4/2009 | Dorian et al. |
| 2009/0112146 A1 | 4/2009 | Wratten et al. |
| 2009/0181019 A1 | 7/2009 | Solinger |
| 2009/0191217 A1 | 7/2009 | de Wildt et al. |
| 2009/0192528 A1 | 7/2009 | Higgins et al. |
| 2009/0220482 A1* | 9/2009 | Higgins ............... A61K 9/0019 424/94.64 |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0263319 A1 | 10/2009 | Wohabrebbi et al. |
| 2009/0289014 A1 | 11/2009 | Hoeppner |
| 2009/0317439 A1 | 12/2009 | Turzi et al. |
| 2010/0008992 A1 | 1/2010 | Ichim |
| 2010/0015129 A1 | 1/2010 | Abramson et al. |
| 2010/0055087 A1 | 3/2010 | Higgins et al. |
| 2010/0125236 A1 | 5/2010 | Bare et al. |
| 2010/0140182 A1 | 6/2010 | Chapman et al. |
| 2010/0186676 A1 | 7/2010 | Van Der |
| 2010/0198130 A1 | 8/2010 | Swift et al. |
| 2010/0206798 A1 | 8/2010 | Dorian et al. |
| 2010/0226909 A1 | 9/2010 | Hecker et al. |
| 2010/0256595 A1 | 10/2010 | Leach et al. |
| 2010/0323870 A1 | 12/2010 | Leach et al. |
| 2010/0324450 A1 | 12/2010 | Leach et al. |
| 2011/0014705 A1 | 1/2011 | Leach et al. |
| 2011/0020196 A1 | 1/2011 | Grippi et al. |
| 2011/0021334 A1 | 1/2011 | Leach et al. |
| 2011/0036786 A1 | 2/2011 | Ellsworth |
| 2011/0052561 A1 | 3/2011 | Hoeppner |
| 2011/0056893 A1 | 3/2011 | Leach et al. |
| 2011/0059082 A1 | 3/2011 | Germer et al. |
| 2011/0059083 A1 | 3/2011 | Aigner et al. |
| 2011/0059084 A1 | 3/2011 | Osterroth et al. |
| 2011/0065183 A1 | 3/2011 | Dorian et al. |
| 2011/0077596 A1 | 3/2011 | Higgins et al. |
| 2011/0129441 A1 | 6/2011 | Lentz |
| 2011/0168193 A1 | 7/2011 | Leach et al. |
| 2011/0189172 A1 | 8/2011 | Solinger et al. |
| 2011/0192804 A1 | 8/2011 | Landrigan et al. |
| 2011/0251041 A1 | 10/2011 | Chavarria et al. |
| 2011/0268708 A1 | 11/2011 | Lin et al. |
| 2011/0300102 A1 | 12/2011 | Chung et al. |
| 2012/0010559 A1 | 1/2012 | Higgins et al. |
| 2012/0015796 A1 | 1/2012 | Leach et al. |
| 2012/0027746 A1 | 2/2012 | Dorian et al. |
| 2012/0093936 A1 | 4/2012 | Lindenberg et al. |
| 2012/0145652 A1 | 6/2012 | Leach et al. |
| 2012/0150086 A1 | 6/2012 | Cohen |
| 2012/0172836 A1 | 7/2012 | Higgins et al. |
| 2012/0228203 A1 | 9/2012 | Hecker et al. |
| 2013/0068676 A1 | 3/2013 | Leach et al. |
| 2013/0102452 A1 | 4/2013 | Leach et al. |
| 2013/0178425 A1 | 7/2013 | Higgins et al. |
| 2013/0196425 A1 | 8/2013 | Dorian et al. |
| 2013/0259951 A1 | 10/2013 | O'Connell, Jr. |
| 2013/0294983 A1 | 11/2013 | Dorian et al. |
| 2014/0051061 A1 | 2/2014 | Landrigan et al. |
| 2014/0054246 A1 | 2/2014 | Landrigan et al. |

(56) References Cited

U.S. PATENT DOCUMENTS

| | | |
|---|---|---|
| 2014/0091048 A1 | 4/2014 | Leach et al. |
| 2014/0242045 A1 | 8/2014 | Higgins et al. |
| 2014/0271587 A1 | 9/2014 | Landrigan et al. |
| 2014/0271588 A1 | 9/2014 | Landrigan et al. |
| 2014/0271589 A1 | 9/2014 | Matuska et al. |
| 2014/0271870 A1 | 9/2014 | O'Shaughnessey et al. |
| 2014/0274893 A1 | 9/2014 | Woodell-May et al. |
| 2014/0274895 A1 | 9/2014 | Binder et al. |
| 2014/0275497 A1 | 9/2014 | Leach et al. |
| 2014/0349388 A1 | 11/2014 | Dorian et al. |
| 2014/0356446 A1 | 12/2014 | Leach et al. |
| 2015/0141332 A1 | 5/2015 | Toler |
| 2015/0147300 A1 | 5/2015 | Woodell-May et al. |
| 2016/0000870 A1 | 1/2016 | Higgins et al. |
| 2016/0017010 A1 | 1/2016 | Higgins et al. |
| 2016/0074479 A1 | 3/2016 | Serbousek et al. |
| 2016/0136245 A1 | 5/2016 | Toler et al. |
| 2016/0166645 A1 | 6/2016 | Matuska et al. |
| 2017/0334960 A1 | 11/2017 | Higgins et al. |
| 2018/0099026 A1 | 4/2018 | Landrigan et al. |

FOREIGN PATENT DOCUMENTS

| | | |
|---|---|---|
| BR | 9103724 A | 3/1993 |
| CA | 1321138 C | 8/1993 |
| CA | 2182862 A1 | 6/1996 |
| CA | 2448415 A1 | 12/2002 |
| CA | 2772084 C | 10/2016 |
| CN | 1074709 A | 7/1993 |
| CN | 1321103 A | 11/2001 |
| CN | 1322146 A | 11/2001 |
| CN | 103702729 A | 4/2014 |
| CN | 105209478 A | 12/2015 |
| CN | 105338990 A | 2/2016 |
| CN | 105339007 A | 2/2016 |
| CN | 105358161 A | 2/2016 |
| CN | 105492015 A | 4/2016 |
| DE | 56103 C | 10/1960 |
| DE | 1443359 A1 | 11/1968 |
| DE | 4202667 C1 | 5/1993 |
| EP | 090997 A2 | 10/1983 |
| EP | 0102773 A2 | 3/1984 |
| EP | 0109374 A1 | 5/1984 |
| EP | 0142339 A1 | 5/1985 |
| EP | 0244834 A2 | 11/1987 |
| EP | 0253198 A1 | 1/1988 |
| EP | 0295771 A2 | 12/1988 |
| EP | 0417818 A1 | 3/1991 |
| EP | 0534178 A2 | 3/1993 |
| EP | 0592242 A1 | 4/1994 |
| EP | 1005910 A2 | 6/2000 |
| EP | 1006360 A2 | 6/2000 |
| EP | 1289618 A1 | 3/2003 |
| EP | 1427279 A1 | 6/2004 |
| EP | 1467746 A2 | 10/2004 |
| EP | 1509326 A2 | 3/2005 |
| EP | 1652538 A2 | 5/2006 |
| EP | 1670315 A2 | 6/2006 |
| EP | 1716901 A1 | 11/2006 |
| EP | 1406492 B1 | 12/2009 |
| EP | 2186877 A2 | 5/2010 |
| EP | 2968409 A1 | 1/2016 |
| EP | 2968412 A1 | 1/2016 |
| EP | 2470163 B1 | 9/2016 |
| GB | 854715 A | 11/1960 |
| JP | 60053845 A | 3/1985 |
| JP | 60250014 A | 12/1985 |
| JP | 2036872 A | 2/1990 |
| JP | 02071747 A | 3/1990 |
| JP | 02129224 A | 5/1990 |
| JP | 069684 A | 1/1994 |
| JP | 07101874 A | 4/1995 |
| JP | 2002509529 A | 3/2000 |
| JP | 2000189407 A | 7/2000 |
| JP | 2000199760 A | 7/2000 |
| JP | 2003525696 A | 9/2003 |
| JP | 2004305439 A | 11/2004 |
| JP | 2005013783 A | 1/2005 |
| JP | 2005098704 A | 4/2005 |
| JP | 2005524451 A | 8/2005 |
| JP | 2006305365 A | 11/2006 |
| JP | 2006527025 A | 11/2006 |
| JP | 2007105186 A | 4/2007 |
| JP | 2007509601 A | 4/2007 |
| JP | 2008104789 A | 5/2008 |
| JP | 2009155234 A | 7/2009 |
| JP | 5551250 B2 | 7/2014 |
| WO | WO-8400905 A1 | 3/1984 |
| WO | WO-8802259 A1 | 4/1988 |
| WO | WO-9010031 A1 | 9/1990 |
| WO | WO9222312 A1 | 12/1992 |
| WO | WO-9305067 A1 | 3/1993 |
| WO | WO-9308904 A1 | 5/1993 |
| WO | WO-9407548 A1 | 4/1994 |
| WO | WO-9617871 A1 | 6/1996 |
| WO | WO-1998024477 A1 | 6/1998 |
| WO | WO-9848938 A1 | 11/1998 |
| WO | 9905989 A2 | 2/1999 |
| WO | 9967277 A1 | 12/1999 |
| WO | WO-0061256 A1 | 10/2000 |
| WO | WO-0074713 A1 | 12/2000 |
| WO | WO-0103756 A1 | 1/2001 |
| WO | WO-0183068 A1 | 11/2001 |
| WO | WO-0238610 A1 | 5/2002 |
| WO | WO-02060925 A1 | 8/2002 |
| WO | WO-02098566 A2 | 12/2002 |
| WO | WO-03015800 A1 | 2/2003 |
| WO | WO-03024215 A1 | 3/2003 |
| WO | WO-03053362 A2 | 7/2003 |
| WO | 03063799 A2 | 8/2003 |
| WO | 03080104 A2 | 10/2003 |
| WO | 03088905 A2 | 10/2003 |
| WO | WO-03092894 A2 | 11/2003 |
| WO | WO-03099412 A1 | 12/2003 |
| WO | 2004/009207 | 1/2004 |
| WO | WO-2004065564 A2 | 8/2004 |
| WO | WO-2004104553 A2 | 12/2004 |
| WO | WO-2005034843 A2 | 4/2005 |
| WO | 2006/043972 A1 | 4/2006 |
| WO | WO-2006041406 A1 | 4/2006 |
| WO | 2007/121538 A1 | 11/2007 |
| WO | 2007/128973 A2 | 11/2007 |
| WO | WO-2007127834 A2 | 11/2007 |
| WO | WO-2007142908 A1 | 12/2007 |
| WO | 2008/021237 A1 | 2/2008 |
| WO | WO-2008127639 A1 | 10/2008 |
| WO | WO-2009021257 A1 | 2/2009 |
| WO | WO-2009108890 A1 | 9/2009 |
| WO | WO-2009111338 A1 | 9/2009 |
| WO | WO-2010115190 A1 | 10/2010 |
| WO | WO-2010149164 A2 | 12/2010 |
| WO | WO-2011008836 A1 | 1/2011 |
| WO | 2011/031553 A2 | 3/2011 |
| WO | WO-2011031524 A2 | 3/2011 |
| WO | WO-2011031524 A3 | 3/2011 |
| WO | WO-2011031525 A1 | 3/2011 |
| WO | 2012/030593 A2 | 3/2012 |
| WO | WO 2012030593 A2 * | 3/2012 | ............. A61K 35/15 |
| WO | WO2012030593 A2 * | 3/2012 |
| WO | WO-2012030593 A3 | 3/2012 |
| WO | WO-2014144505 A2 | 9/2014 |
| WO | WO-2014144505 A3 | 9/2014 |
| WO | WO-2015099684 A1 | 7/2015 |

OTHER PUBLICATIONS

Arend, W. et al. "Interleukin-1 Receptor Antagonist: Role in Biology" Annu. Rev. Immunol., vol. 16 (pp. 27-55) 1998.

Baltzer AW, et al. Autologous conditioned serum (Orthokine) is an effective treatment for knee osteoarthritis. Osteoarthritis Cartilage Feb. 1, 2009; 17(2):152-60.

Becker C. et al. Efficacy of epidural perineural injections with autologous conditioned serum for lumbar radicular compression: an

(56) References Cited

OTHER PUBLICATIONS

Investigator-initiated, prospective, double-blind, reference-controlled study. Spine Aug. 1, 2007; 32(17):1803-8.
Bendele et al. "Combination benefit of treatment with the cytokine inhibitors interleukin-1 receptor antagonist and PEGylated soluble tumor necrosis factor receptor type I in animal models of rheumatoid arthritis" Arthritis & Rheumatism, vol. 43, No. 12, Dec. 2000, pp. 2648-2659.
Bielecki, T. et al, "Antibacterial effect of autologous platelet gel enriched with growth factors and toher acive substances" J Bone Joint Surg, vol. 89-B, No. 3 (p. 417-420) Mar. 2007.
Bio-Rad Laboratories. Bio-Gel P Polyacrylamide Gel Instruction Manual, Obtained from www.bio-rad.com/webmaster/pdfs/9154_Bio-Gel_P.pdf on Jun. 20, 2012 (14 pages).
Biomet Biologics, Inc. "GPS® II Platelet Concentrate System: The New Gold Standard" Product Brochure (14 pages) Sep. 2006.
Biomet Biologics, Inc. "GPS® III Platelet Separation System" Product Brochure (8 pages) 2007.
Biomet Biologics, Inc. "Plasmax Plasma Concentrate" Product Brochure (6 pages) 2006.
Biomet Biologics, Inc. "Vortech Concentration System Product" Product Brochure (16 pages) Aug. 2005.
Biomet Biologics, Inc. "GPS System Shoulder Recovery with the GPS Platelet Concentrate System" Product Brochure (6 pages) 2004.
Burnouf, T. "Blood-derived, tissue engineering biomaterials" Biomedical Engineering-Applications, Basis & Communications, vol. 16, No. 6, Dec. 2004 (pp. 294-304).
Cell Factor Technologies, Inc. "GPS® Platelet Concentrate System" Product Brochure (9 pages) 2004.
Cell Factor Technologies, Inc., Biomet Europe. "GPS® II System, Gravitational Platelet Separation System" User Manual (13 pages), http://www.cellfactortech.com/global_products.cfm, printed Sep. 16, 2005.
Cell Factor Technologies, Inc., Biomet Europe. "GPS® II System, Gravitational Platelet Separation System, Accelerating the Body's Natural Healing Process" Product Bruchure (16 pages) 2005.
Dallari et al. "Enhanced Tibial Osteotomy Healing with Use of Bone Grafts Supplemented with Platelet Gel or Platelet Gel and Bone Marrow Stromal Cells" The Journal of Bone and Joint Surgery, vol. 89 (2007) pp. 2413-2420.
Dinarello, C. "Interleukin-1 and Interleukin-1 Antagonism" Blood, vol. 77, No. 8 (pp. 1627-1652) Apr. 1991.
Dinarello, C. A. Interleukin-1 in the pathogenesis and treatment of inflammatory diseases. Blood, 2011, vol. 117 (14), p. 3720-3732.
Eppley, et al. "Platelet Quantification and Growth Factor Analysis from Platelet-Rich Plasma: Implications for Wound Healing," Plastic and Reconstructive Surgery, 114(6):1502-1508 (Nov. 2004).
Evans, C.H.Novel biological approaches to the intra-articular treatment of osteoarthritis. BioDrugs 2005; 19(6):355-62.
Fiotti et al. "Atherosclerosis and Inflammation. Patterns of Cytokine Regulation in Patients with Peripheral Arterial Disease" Atherosclerosis, Elsevier Ireland Ltd, IE, vol. 145, No. 1, pp. 51-60. Jul. 1, 1999.
Floryan, K. et al. "Home Study Program: Intraoperative use of Autologous Platelet-Rich and Platelet-Poor Plasma for Orthopedic Surgery Patients" vol. 80, No. 4 (Oct. 2004) p. 667-674.
Hou, WH et al. "Microfluidic Devices for Blood Fractionation" Micromachines (2011) 2, 319-343.
Juge-Aubry, C. et al. "Adipose Tissue is a Major Source of Interleukin-1 Receptor Antagonist" Diabetes, vol. 52, May 2003 (pp. 1104-1110).
Kaufman, A. et al. "Human macrophage response to UHMWPE, TiAIV, CoCr, and alumina particles: Analysis of multiple cytokines using protein arrays" Journal of Biomedical Materials Research Part A, published online in Wiley InterScience DOI: 10.1002/jbm.a.31467 (pp. 464-474) Jul. 2007.

Kim, Seon Hee et al. "Ex vivo gene delivery of Il-1Ra and soluble TNF receptor confers a distal synergistic therapeutic effect in antigen-induced arthritis", Molecular Therapy, vol. 6, No. 5, Nov. 1, 2002 (pp. 591-600).
King, W. et al. "A simple method to Correlate the Concentration of an Anti-Inflammatory Cytokine with White Blood Cells in an Autologous Protein Solution" Feb. 24, 2014.
Klingenberg et al. "Treating inflammation in Atherosclerotic Cardiovascular Disease: Emerging Therapies" European Heart Journal., vol. 30, No. 23, pp. 2838-2844, Dec. 2009.
Lavi, G. et al. "Sustained delivery of IL-1Ra from biodegradable microspheres reduces the number of murine B16 melanoma lung metastases" Journal of Controlled Release. 123, 123-130 (2007).
Lucarelli, E. et al. "Platelet-derived growth factors enhance proliferation of human stromal stem cells" Biomaterials, vol. 24 (2003) pp. 3095-3100.
Matthews, J. et al. "Comparison of the response of primary human peripheral blood mononuclear phagocytes from different donors to challenge with model polyethylene particles of known size and dose" Biomaterials, vol. 21 (pp. 2033-2044) 2000.
Meijer, H. et al. "The production of antiinflammatory cytokines in whole blood by physico-chemical induction" Inflamm. Res., vol. 52 (pp. 404-407) Oct. 2003.
Miltenyi Biotec GmbH, Isolation of Granulocytes From Human Peripheral Blood by Density Gradient Centrifugation (2008) 2 pages.
Morizaki et al. "The Effects of Platelet-Rich Plasma on Bone Marrow Stromal Cell Transplants for Tendon Healing in Vitro" J. Hand Surg. Am., vol. 35, No. 11 (Nov. 2010) pp. 1833-1841.
Murphy et al. "Autologous Bone Marrow Mononuclear Cell Therapy is Safe and Promotes Amputation-free Survival in Patients with Critical Limb Ischemia" Journal of Vascular Surgery, C.V. Mosby Co., vol. 53, No. 6, Jan. 28, 2011.
Muzio, M. et al. "Interleukin-13 Induces the Production of Interleukin-1 Receptor Antagonist (IL-1ra) and the Expression of the mRNA for the Intracellular (Keratinocyte) Form of IL-1ra in Human Myelomonocytic Cells" Blood, vol. 83, No. 7 (pp. 1738-1743) Apr. 1994.
Nursen Düzgün et al. "Cytokine inhibitors: soluble tumor necrosis factor receptor 1 and interleukin-1 receptor antagonist in Behçet's disease" Rheumatology International ; Clinical and Experimental Investigations, Springer, Berlin, DE vol. 25, No. 1, Jan. 2005. p. 1-5.
O'Shaughnessey, K.M. et al. Blood-derived anti-inflammatory protein solution blocks the effect of IL-1beta on human macrophages in vitro. Inflamm Res Oct. 2011; 60(10):929-36.
Plasmax® Plasma Concentration System. 2007. Biomet Biologics. p. 1-20.
Rader, C. et al. "Cytokine Response of Human Macrophage-like Cells After Contact With Polyethylene and Pure Titanium Particles" The Journal of Arthroplasty, vol. 14, No. 7 pp. 840-848 (Oct. 1999).
Sorbera L A "Pegsunercept. Pegylated Soluble Tumor Necrosis Factor Receptor Type 1 PEG-STNF-RI" Drugs of the Future, Prous Science, ES, vol. 28, No. 12. Jan. 1, 2003. p. 1182-1188.
Swift, M. et al. "Characterization of Growth Factors in Platelet Rich Plasma" Cell Factor Technologies, Inc. Printed Sep. 16, 2005 from www.cellfactortech.com/global_products.cfm.
Tateishi-Yuyama, E. et al. "Therapuetic angiogenesis for patients with limb ischaemia by autologous transplantation of bone-barrow cells: a pilot study and randomised controlled trial" The Lancet 2002; 360:427-435.
Ulich, T.R. et al. "Intratrachael Administration of Endotoxin and Cytokines: IV. The Soluble Tumor Necrosis Factor Receptor Type 1 Inhibits Acute Inflammation" American Journal of Pathology; vol. 142, No. 5, May 1993.
Vangsness, T. et al. "Stimulation of IL-1ra Production from Platelet-Rich Plasma" Poster No. 488 presented at 54th Annual Meeting of the Orthopeadic Research Society in San Francisco, CA (1 page) Mar. 2-5, 2008.
Woodell-May, J. et al. "Effect of Incubation Time on Production of IL-1ra and sTNF-RI from Platelet-Rich Plasma" Paper No. 200, 55th Annual Meeting of the Orthopaedic Research Society (1 page) Feb. 2009.

(56) References Cited

OTHER PUBLICATIONS

Woodell-May, J. et al. "Elution of IL-1ra from a concentrated-plasma matrix—An in vitro study" Poster Presentation at 8th World Congress of the International Cartilage Repair Society, Miami, FL. (1 page) May 2009.
"U.S. Appl. No. 12/394,723, Response filed Mar. 6, 2017 to Non Final Office Action dated Oct. 5, 2016", 25 pgs.
"U.S. Appl. No. 13/392,266, Notice of Allowance dated Mar. 6, 2017", 8 pgs.
"U.S. Appl. No. 13/392,266, Response filed Jan. 4, 2017 to Non Final Office Action dated Oct. 4, 2016", 22 pgs.
"U.S. Appl. No. 13/837,005, Response filed Dec. 22, 2016 to Advisory Action dated Dec. 2, 2016", 10 pgs.
"U.S. Appl. No. 13/841,083, Examiner Interview dated Feb. 24, 2017", 1 pg.
"U.S. Appl. No. 13/841,083, Non Final Office Action dated Feb. 24, 2017", 12 pgs.
"U.S. Appl. No. 13/841,103, Response filed Mar. 13, 2017 to Final Office Action dated Dec. 14, 2016", 14 pgs.
"U.S. Appl. No. 14/803,414, Non Final Office Action dated Apr. 19, 2017", 35 pgs.
"U.S. Appl. No. 14/803,414, Response filed Dec. 19, 2016 to Restriction Requirement dated Oct. 20, 2016", 7 pgs.
"U.S. Appl. No. 14/808,828, Response filed Mar. 8, 2017 to Non Final Office Action dated Dec. 8, 2016", 9 pgs.
"U.S. Appl. No. 14/830,977, Response filed Jan. 20, 2017 to Final Office Action dated Oct. 20, 2016", 27 pgs.
"Application Serial No. 14709014.6, Response filed Feb. 27, 2017 to Non Final Office Action dated Oct. 20, 2016", 22 pgs.
"Application Serial No. 14714491.9, Non Final Office Action dated Mar. 6, 2017", 9 pgs.
"Canadian Application No. 2,810,202, Response filed Jan. 26, 2017 to Non Final Office Action dated Aug. 11, 2016", 8 pgs.
"Canadian Application Serial No. 2,810,202, Office Action dated Aug. 11, 2016", 4 pgs.
"Chinese Application Serial No. 201480027178.3, Voluntary Amendment filed Jul. 15, 2016", w/English claims, 35 pgs.
"European Application No. 15184504.7, Response filed Jan. 25, 2017 to Non Final Office Action dated Sep. 16, 2016", 10 pgs.
"European Application No. 10754613.7, Non Final Office Action dated Feb. 7, 2017", 5 pgs.
"European Application Serial No. 14707069.2, Response Filed Mar. 27, 2017 to Communication Pursuant to Article 94(3) EPC dated Nov. 5, 2016", 16 pgs.
"European Application Serial No. 14707909.9, Communication Pursuant to Article 94(3) EPC dated Dec. 16, 2016", 5 pgs.
"European Application Serial No. 14714491.9, Communication Pursuant to Article 94(3) EPC dated Feb. 28, 2017", 9 pgs.
"European Application Serial No. 15184504.7, Communication Pursuant to Article 94(3) EPC dated Feb. 13, 2016", 5 pgs.
"European Application Serial No. 15184504.7, Communication Pursuant to Article 94(3) EPC dated Feb. 13, 2017", 6 pgs.
Abegao, K., et al., "Effects of heterologous platelet-rich plasma gel on standardized dermal wound healing in rabbits", Acta Cirurgica Brasileira—vol. 30(3), (2015), pp. 208-215.
Abramson, S. B., et al., "Blocking the effects o IL-1 in rheumatoid arthritis protects bone and cartilage", Rheumatology; 41, (2002), 972-980 pgs.
Agu, R. U., et al., "The lung as a route for systemic delivery of therapeutic proteins and peptides", Respir Res.; vol. 2, (2001), pp. 198-209.
Danis, V. A., et al., "Cytokine production by normal human monocytes: inter-subject variation and relationship to an IL-1 receptor antagonist (IL-IRa) gene polymorphism", Clin Exp Immunol; (99), (1995), p. 303-310.
Fini, M., et al., "Effects of pulsed electromagnetic fields on articular hyaline cartilage: review of experimental and clinical studies", Biomed Pharmacother; vol. 59, (2005), pp. 388-394.

Greppi, N., et al., "Treatment of recalcitrant ulcers with allogeneic platelet gel from pooled platelets in aged hypomobile patients", Biologicals. Academic Press Ltd. vol. 39. No. 2, (Jan. 6, 2011), 73-80 pgs.
Gullung, Gregory B., et al., "Platelet-rich plasma effects on degenerative disc disease: analysis of histology and imaging in an animal model", Evidence-Based Spine-Care Journal, vol. 2, Issue 4, (2011), 13-18.
Ma, Chaoyong, "Animal Models of Disease: These systems are becoming increasingly important secondary screes of in vitro hits.", Modern Drug Discovery, (Jun. 2004), pp. 30-36.
Obata, Shuji, et al., "Effect of autologous platelet-rich plasma-releasate on intervertebral disc degeneration in the rabbit anular puncture model: a preclinical study", Arthritis Research & Therapy. vol. 14 http://arthritis-research.com/content/14/6/R241, (2012), 12 pgs.
Ravi Kumar, H. S., et al., "Autologous Conditioned Serum as a Novel Alternative Option in the Treatment of Unilateral Lumbar Radiculopathy: A Prospective Study", Asian Spine Journal; 9(6), (2015), 916-922.
Sampson, Steven, et al., "Platelet rich plasma injection grafts for musculoskeletal injuries: a review", Curr Rev Musculoskelet Med, vol. 1, (Jul. 16, 2008), 165-174.
Stankiewicz, W., et al., "Low energy electromagnetic fields and immunity", Int. Rev. Allergol. Clin. Immunol, vol. 15, No. 1-2, (2009), pp. 36-41.
Xie, X., et al., "Biology of platelet-rich plasma and its clinical application in cartilage repair", Arthritis Research & Therapy, 16:204, (2014), 15 pgs.
Zhang, et al., "Nanosecond pulse electric field (nanopulse): A novel non-ligand agonist for platelet activation", Archives of Biochemistry and Biophysics, Academic Press, US, vol. 471, No. 2, (Dec. 23, 2007), 240-248.
"U.S. Appl. No. 12/101,586, Final Office Action dated Feb. 3, 2011", 11 pgs.
"U.S. Appl. No. 12/101,586, Non Final Office Action dated Sep. 20, 2010", 12 pgs.
"U.S. Appl. No. 12/101,586, Notice of Allowance dated Mar. 24, 2011", 5 pgs.
"U.S. Appl. No. 12/101,594, Final Office Action dated Mar. 18, 2010", 8 pgs.
"U.S. Appl. No. 12/101,594, Non Final Office Action dated Oct. 16, 2009", 8 pgs.
"U.S. Appl. No. 12/101,594, Notice of Allowance dated May 27, 2010", 7 pgs.
"U.S. Appl. No. 12/394,723, Appeal Brief filed Jun. 15, 2015", 42 pgs.
"U.S. Appl. No. 12/394,723, Decision on Pre-Appeal Brief dated Feb. 13, 2015", 2 pgs.
"U.S. Appl. No. 12/394,723, Examiner's Answer to Appeal Brief dated Sep. 9, 2015", 11 pgs.
"U.S. Appl. No. 12/394,723, Final Office Action dated Apr. 19, 2016", 13 pgs.
"U.S. Appl. No. 12/394,723, Non Final Office Action dated Dec. 24, 2015", 9 pgs.
"U.S. Appl. No. 12/394,723, Response filed Jan. 8, 2015 to Pre-Appeal Brief Request dated Dec. 19, 2014", 4 pgs.
"U.S. Appl. No. 12/394,723, Response filed Aug. 19, 2016 to Final Office Action dated Apr. 19, 2016", 23 pgs.
"U.S. Appl. No. 12/394,723, Response filed Nov. 9, 2015 to Final Office Action dated Sep. 8, 2014", 19 pgs.
"U.S. Appl. No. 12/394,723, Response filed Mar. 24, 2016 to Non Final Office Action dated Dec. 24, 2015", 18 pgs.
"U.S. Appl. No. 12/549,116, Decision on Pre-Appeal Brief dated Feb. 5, 2015", 2 pgs.
"U.S. Appl. No. 12/549,116, Final Office Action dated Jan. 4, 2016", 15 pgs.
"U.S. Appl. No. 12/549,116, Non Final Office Action dated Jun. 4, 2015", 12 pgs.
"U.S. Appl. No. 12/549,116, Pre-Appeal Brief Request filed Jan. 8, 2015", 5 pgs.
"U.S. Appl. No. 12/549,116, Response filed Mar. 3, 2016 to Final Office Action dated Jan. 4, 2016", 11 pgs.

(56) References Cited

OTHER PUBLICATIONS

"U.S. Appl. No. 12/549,116, Response filed Sep. 4, 2015 to Non Final Office Action dated Jun. 4, 2015", 9 pgs.
"U.S. Appl. No. 12/897,401, Non Final Office Action dated Nov. 16, 2010", 9 pgs.
"U.S. Appl. No. 12/897,401, Notice of Allowance dated Oct. 18, 2011", 6 pgs.
"U.S. Appl. No. 13/392,266, Final Office Action dated Jul. 30, 2015", 12 pgs.
"U.S. Appl. No. 13/392,266, Non Final Office Action dated Feb. 26, 2015", 9 pgs.
"U.S. Appl. No. 13/392,266, Response filed Jan. 22, 2016 to Final Office Action dated Jul. 30, 2015", 24 pgs.
"U.S. Appl. No. 13/392,266, Response filed Jul. 8, 2015 to Non-Final Office Action dated Feb. 26, 2015", 13 pgs.
"U.S. Appl. No. 13/782,421, Final Office Action dated Jan. 15, 2015", 30 pgs.
"U.S. Appl. No. 13/782,421, Notice of Allowance dated Apr. 27, 2015", 8 pgs.
"U.S. Appl. No. 13,782,421, Response filed Apr. 15, 2015 to Final Office Action dated Jan. 15, 2015", 6 pgs.
"U.S. Appl. No. 13/837,005, Final Office Action dated Aug. 23, 2016", 9 pgs.
"U.S. Appl. No. 13/837,005, Non Final Office Action dated Feb. 17, 2016", 13 pgs.
"U.S. Appl. No. 13/837,005, Non Final Office Action dated Jun. 9, 2015", 13 pgs.
"U.S. Appl. No. 13/837,005, Response filed Mar. 5, 2015 to Final Office Action dated Dec. 5, 2014", 11 pgs.
"U.S. Appl. No. 13/837,005, Response filed May 17, 2016 to Non Final Office Action dated Feb. 17, 2016", 13 pgs.
"U.S. Appl. No. 13/837,005, Response filed Nov. 9, 2015 to Non Final Office Action dated Jun. 9, 2015", 11 pgs.
"U.S. Appl. No. 13/837,480, Final Office Action dated May 23, 2016", 11 pgs.
"U.S. Appl. No. 13/837,480, Non Final Office Action dated Aug. 11, 2015", 10 pgs.
"U.S. Appl. No. 13/837,480, Response filed Jan. 11, 2016 to Non Final Office Action dated Aug. 11, 2015", 14 pgs.
"U.S. Appl. No. 13/840,129, Final Office Action dated Jun. 18, 2015", 9 pgs.
"U.S. Appl. No. 13/840,562, Final Office Action dated Jan. 20, 2016", 14 pgs.
"U.S. Appl. No. 13/840,562, Non Final Office Action dated Apr. 24, 2015", 23 pgs.
"U.S. Appl. No. 13/840,562, Response filed Apr. 18, 2016 to Final Office Action dated Jan. 20, 2016", 18 pgs.
"U.S. Appl. No. 13/840,562, Response filed Jul. 29, 2015 to Non Final Office Action dated Apr. 24, 2015", 13 pgs.
"U.S. Appl. No. 13/841,083, Examiner Summary dated Jan. 29, 2016", 1 pg.
"U.S. Appl. No. 13/841,083, Non Final Office Action dated Jan. 29, 2016", 11 pgs.
"U.S. Appl. No. 13/841,083, Non Final Office Action dated Jul. 15, 2015", 8 pgs.
"U.S. Appl. No. 13/841,083, Response filed Apr. 10, 2015 to Non Final Office Action dated Dec. 10, 2014", 17 pgs.
"U.S. Appl. No. 13/841,083, Response filed Apr. 28, 2016 to Non Final Office Action dated Jan. 29, 2016", 11 pgs.
"U.S. Appl. No. 13/841,083, Response filed Aug. 27, 2014 to Restriction Requirement dated Jul. 21, 2014", 3 pgs.
"U.S. Appl. No. 13/841,083, Response filed Oct. 13, 2015 to Non Final Office Action dated Jul. 15, 2015", 10 pgs.
"U.S. Appl. No. 13/841,103, Final Office Action dated Aug. 13, 2015", 13 pgs.
"U.S. Appl. No. 13/841,103, Non Final Office Action dated Jun. 7, 2016", 16 pgs.
"U.S. Appl. No. 13/841,083, Response filed Jan. 13, 2016 to Final Office Action dated Aug. 13, 2015", 11 pg.
"U.S. Appl. No. 13/841,103, Response filed Apr. 18, 2016 to Restriction Requirement dated Feb. 19, 2016", 8 pgs.
"U.S. Appl. No. 13/841,103, Response filed May 4, 2015 to Non Final Office Action dated Dec. 4, 2014", 18 pgs.
"U.S. Appl. No. 13/841,103, Response filed Aug. 31, 2016 to Non Final Office Action dated Jun. 7, 2016", 15 pgs.
"U.S. Appl. No. 13/841,103, Restriction Requirement dated Feb. 19, 2016", 7 pgs.
"U.S. Appl. No. 13/987,480, Response filed Jul. 25, 2016 to Final Office Action dated May 23, 2016", 13 pgs.
"U.S. Appl. No. 14/050,950, Final Office Action dated Jun. 17, 2016", 9 pgs.
"U.S. Appl. No. 14/050,950, Non Final Office Action dated Nov. 19, 2015", 13 pgs.
"U.S. Appl. No. 14/050,950, Response filed Feb. 19, 2016 to Non Final Office Action dated Nov. 19, 2015", 11 pgs.
"U.S. Appl. No. 14/050,950, Response filed Jun. 23, 2015 to Restriction Requirement dated Apr. 23, 2015", 1 pgs.
"U.S. Appl. No. 14/050,950, Response filed Aug. 17, 2016 to Final Office Action dated Jun. 17, 2016", 8 pgs.
"U.S. Appl. No. 14/050,950, Restriction Requirement dated Apr. 23, 2015", 7 pgs.
"U.S. Appl. No. 14/271,722, Notice of Allowance dated Jan. 15, 2016", 13 pgs.
"U.S. Appl. No. 14/803,414, Preliminary Amendment filed Sep. 16, 2015", 7 pgs.
"U.S. Appl. No. 14/803,414, Supplemental Preliminary Amendment Filed Feb. 3, 2016", 8 pgs.
"U.S. Appl. No. 14/808,828,Preliminary Amendment filed Jul. 24, 2015", 12 pgs.
"U.S. Appl. No. 14/808,828, Restriction Requirement dated Aug. 2, 2016", 6 pgs.
"U.S. Appl. No. 14/808,828, Supplemental Preliminary Amendment filed Jul. 27, 2015", 10 pgs.
"U.S. Appl. No. 14/808,828, Supplemental Preliminary Amendment filed Oct. 6, 2015", 7 pgs.
"U.S. Appl. No. 14/830,977, Non Final Office Action dated Apr. 13, 2016", 16 pgs.
"U.S. Appl. No. 14/830,977, Response filed Jul. 13, 2016 to Non Final Office Action dated Apr. 13, 2016", 10 pgs.
"U.S. Appl. No. 14/973,913, Preliminary Amendment filed Mar. 2, 2016", 10 pgs.
"Australian Application Serial No. 2011296356, Response filed Jun. 11, 2015 to First Examiner Report dated Jun. 20, 2014", 20 pgs.
"BioCUE™ Platelet Concentration System", (Jun. 2010), 2 pgs.
"Canadian Application Serial No. 2,772,067, Office Action dated Jan. 8, 2015", 3 pgs.
"Canadian Application Serial No. 2,772,067, Office Action dated Nov. 24, 2015", 3 pgs.
"Canadian Application Serial No. 2,772,067, Response filed Mar. 1, 2016 to Office Action dated Nov. 24, 2015", 7 pgs.
"Canadian Application Serial No. 2,772,067, Response filed Jul. 8, 2015 to Office Action dated Jan. 8, 2015", 24 pgs.
"Canadian Application Serial No. 2,772,069, Office Action dated Sep. 16, 2015", 3 pgs.
"Canadian Application Serial No. 2,772,084, Office Action dated Jun. 11, 2015", 3 pgs.
"Canadian Application Serial No. 2,810,202, Office Action dated Jul. 2, 2015", 5 pgs.
"Canadian Application Serial No. 2,810,202, Response filed Dec. 30, 2015 to Office Action dated Jul. 2, 2015", 19 pgs.
"Canadian Application Serial No. 2,905,552, Voluntary Amendment filed Sep. 11, 2015".
"Canadian Application Serial No. 2,906,310, Voluntary Amendment filed Sep. 14, 2015", 2 pgs.
"Caps for Corning® and Costar® Plastic Labware", Technical Bulletin, (Dec. 2008), 2 pgs.
"Cell Isolation Techniques, Methods and Materials, Working with Enzymes", Worthington Biochemical Corp, (2004), 9 pgs.
"Cell Isolation Theory, Tissue Types", Worthington Biochemical Corp, (2004), 5 pgs.
"Centrifuge Tubes", Corning Costar, (1996/1997), 76-77.

(56) References Cited

OTHER PUBLICATIONS

"Chinese Application Serial No. 201080019707.7, Office Action dated Jun. 30, 2014", in English, 7 pgs.
"Chinese Application Serial No. 2010800447744, Notification of Reexamination dated Feb. 23, 2016", W/ English Translation, 9 pgs.
"Chinese Application Serial No. 2010800447744, Response filed Feb. 19, 2015 to Decision on rejection dated Nov. 15, 2014", (W/ English Translation), 13 pgs.
"Chinese Application Serial No. 2010800447744, Response filed Apr. 11, 2016 to Notification of Reexamination dated Feb. 23, 2016", with English translation of claims, 23 pgs.
"Chinese Application Serial No. 2011800457327, Office Action dated Sep. 28, 2015", No English translation, 6 pgs.
"Chinese Application Serial No. 201280030026.X, Office Action dated Nov. 21, 2014", w/ English Translation, 27 pgs.
"Chinese Application Serial No. 201480027541.1, Voluntary Amendment dated May 5, 2016", w/ English Translation, 15 pgs.
"Clotalyst® Autologous Clotting Factor", "Would you like to have an autologous thrombin for rapid clotting and haemostasis?" Biomet Biologics, (Jan. 2007), 16 pgs.
"Corning® 15 and 50 ml Centrifuge Tubes", Life Sciences. Corning Incorporated., (Jun. 2005), 2 pgs.
"Cytori Celution Cell Concentrate Device", Exhibit 14, 501(k) Summary, FDA approval K060482, (Sep. 28, 2006), 7 pgs.
"European Application Serial No. 10712677.3, Examination Notification Art. 94(3) dated Jun. 5, 2013", 5 pgs.
"European Application Serial No. 10754379.5, Response filed Apr. 13, 2015 to Examination Notification Art. 94(3) dated Dec. 15, 2014", 8 pgs.
"European Application Serial No. 10754613.7, Communication Pursuant to Article 94(3) EPC dated Nov. 13, 2015", 4 pgs.
"European Application Serial No. 10754613.7, Response filed Mar. 15, 2016 to Communication Pursuant to Article 94(3) EPC dated Nov. 13, 2015", 26 pgs.
"European Application Serial No. 13165543.3, Response filed Oct. 24, 2014 to Non Final Office Action dated Jun. 27, 2014", 6 pgs.
"European Application Serial No. 14707069.2, Response filed May 23, 2016 to Communication pursuant to Rules 161(1) and 162 EPC dated Nov. 12, 2015", 12 pgs.
"European Application Serial No. 14707909.9, Communication Pursuant to Article 94(3) EPC dated Jul. 22, 2016", 9 pgs.
"European Application Serial No. 14707909.9, Preliminary Amendment filed on May 13, 2016", 14 pgs.
"European Application Serial No. 14707909.9, Response filed May 13, 2016 to Communication pursuant to Rules 161(1) and 162 EPC dated Nov. 3, 2015", 14 pgs.
"European Application Serial No. 14709014.6, Office Action dated Nov. 19, 2015", 2 pgs.
"European Application Serial No. 14709803.2, Response filed May 16, 2016 to Communication pursuant to Rules 161(1) and 162 EPC dated Nov. 5, 2015", 14 pgs.
"European Application Serial No. 14714491.9, Response filed Aug. 1, 2016 to Communication Pursuant to Rules 161 and 162 EPC dated Jan. 21, 2016", 11 pgs.
"European Application Serial No. 14724817.3, Office Action dated Oct. 27, 2015", 2 pgs.
"European Application Serial No. 14724817.3, Response filed May 6, 2016 to Communication pursuant to Rules 161(1) and 162 EPC dated Oct. 27, 2015", 13 pgs.
"European Application Serial No. 14729994.5, Response filed May 9, 2016 to Communication pursuant to Rules 161(1) and 162 EPC dated Oct. 30, 2015", 14 pgs.
"European Application Serial No. 15184504.7, Extended European Search Report dated Oct. 20, 2015", 7 pgs.
"Fibrostik™ Plasma Concentrator", Attention Operating Surgeon, Cell Factor Technologies, Inc., (Jul. 2003), 2 pgs.
"Frequently Asked Questions, 1. Kits, 2. Enzymes", Worthington Biochemical Corp, (2003), 3 pgs.
"GPS® III Platelet Separation System, Leadership through Technology", Biomet Biologics, Inc, (Jul. 2007), 8 pgs.

"Hemocor HPH® Hemoconcentrator", Minntech® Filtration Technologies Group, Minntech Corporation (2004), <http://www.minntech.com/ftg/products/hph/index.html>, (Jul. 15, 2004), 2 pgs.
"Increasing bone graft bioactivity through reproducible concentrations of natural growth factors", Symphony II Platelet Concentrate System/PCS brochure, (Jan. 2003), 8 pgs.
"International Application Serial No. PCT/US2003/016506, International Search Report dated Oct. 13, 2003", 2 pgs.
"International Application Serial No. PCT/US2007/012587, International Search Report dated Nov. 6, 2007", 2 pgs.
"International Application Serial No. PCT/US2008/004687, International Preliminary Report on Patentability dated Aug. 13, 2009", 19 pgs.
"International Application Serial No. PCT/US2008/004687, International Search Report dated Jul. 2, 2008", 3 pgs.
"International Application Serial No. PCT/US2008/004687, Written Opinion dated Mar. 17, 2009", 5 pgs.
"International Application Serial No. PCT/US2008/004687, Written Opinion dated Jul. 2, 2008", 5 pgs.
"International Application Serial No. PCT/US2009/035564, International Preliminary Examination Report dated Aug. 31, 2010", 6 pgs.
"International Application Serial No. PCT/US2009/035564, International Search Report dated Jul. 3, 2009", 3 pgs.
"International Application Serial No. PCT/US2009/035564, Written Opinion dated Jul. 3, 2009", 5 pgs.
"International Application Serial No. PCT/US2010/029957, International Preliminary Report on Patentability dated Oct. 13, 2011", 10 pgs.
"International Application Serial No. PCT/US2010/029957, International Search Report dated Jul. 30, 2010", 6 pgs.
"International Application Serial No. PCT/US2010/029957, Written Opinion dated Jul. 30, 2010", 9 pgs.
"International Application Serial No. PCT/US2010/041942, International Preliminary Report on Patentability dated Jan. 26, 2012", 9 pgs.
"International Application Serial No. PCT/US2010/041942, International Search Report dated Oct. 8, 2010", 3 pgs.
"International Application Serial No. PCT/US2010/041942, Written Opinion dated Oct. 8, 2010", 8 pgs.
"international Application Serial No. PCT/US2011/031954, Written Opinion dated Aug. 9, 2011", 9 pgs.
"International Application Serial No. PCT/US2011/045290, International Search Report dated Nov. 7, 2011", 5 pgs.
"International Application Serial No. PCT/US2011/045290, Written Opinion dated Nov. 7, 2011", 5 pgs.
"International Application Serial No. PCT/US2012/034104, International Preliminary Report on Patentability dated Oct. 31, 2013", 7 pgs.
"International Application Serial No. PCT/US2012/034104, International Search Report dated Oct. 29, 2012", 5 pgs.
"International Application Serial No. PCT/US2012/034104, Written Opinion dated Oct. 29, 2012", 6 pgs.
"International Application Serial No. PCT/US2013/056793, International Preliminary Report on Patentability dated Mar. 12, 2015", 8 pgs.
"International Application Serial No. PCT/US2013/056793, International Search Report dated Dec. 5, 2013", 3 pgs.
"International Application Serial No. PCT/US2013/056793, Written Opinion dated Dec. 5, 2013", 6 pgs.
"International Application Serial No. PCT/US2014/016384, International Preliminary Report on Patentability dated Sep. 24, 2015", 16 pgs.
"International Application Serial No. PCT/US2014/016421, International Preliminary Report on Patentability dated Sep. 24, 2015", 16 pgs.
"International Application Serial No. PCT/US2014/016895, International Preliminary Report on Patentability dated Sep. 24, 2015", 16 pgs.
"International Application Serial No. PCT/US2014/016900, International Preliminary Report on Patentability dated Sep. 24, 2015", 9 pgs.

(56) References Cited

OTHER PUBLICATIONS

"International Application Serial No. PCT/US2014/021707, International Preliminary Report on Patentability dated Sep. 24, 2015", 16 pgs.

"International Application Serial No. PCT/US2014/023091, International Preliminary Report on Patentability dated Sep. 24, 2015", 11 pgs.

"International Application Serial No. PCT/US2014/028942, International Preliminary Report on Patentability dated Sep. 24, 2015", 15 pgs.

"Japanese Application Serial No. 2010-503066, Office Action dated Jan. 22, 2013", w/ English Translation, 17 pgs.

"Japanese Application Serial No. 2012-503768, Office Action dated May 20, 2014", w/ English Translation, 5 pgs.

"Japanese Application Serial No. 2012-520742, Office Action dated Sep. 9, 2014", w/ English Translation, 6 pgs.

"Japanese Application Serial No. 2012-526990, Examiners Decision of Final Refusal dated Jun. 3, 2016", W/ English Translation, 6 pgs.

"Japanese Application Serial No. 2012-526990, Office Action dated Jun. 26, 2015", (W/ English Translation), 12 pgs.

"Japanese Application Serial No. 2012-526990, Response filed Dec. 25, 2015 to Office Action dated Jun. 26, 2015", (W/ English Translation), 14 pgs.

"Japanese Application Serial No. 2012-527030, Office Action dated Jun. 12, 2015", (English translation), 2 pgs.

"Japanese Application Serial No. 2013-174962, Notice of Reasons for Rejection dated Jul. 31, 2015", W/ English Translation, 10 pgs.

"Japanese Application Serial No. 2013-174962, Response filed Mar. 12, 2015 to Office Action dated Sep. 12, 2014", (W/ English Translation), 18 pgs.

"Japanese Application Serial No. 2013-174962, Response filed Oct. 30, 2015 to Notice of Reasons for Rejection dated Jul. 31, 2015", W/ English Claims, 16 pgs.

"Japanese Application Serial No. 2013-527119, Office Action dated Mar. 1, 2016", W/ English Translation, 12 pgs.

"Japanese Application Serial No. 2013-527119, Office Action dated Jun. 12, 2015", (W/ English Translation), 11 pgs.

"Japanese Application Serial No. 2013-527119, Response filed Aug. 1, 2016 to Office Action dated Mar. 1, 2016", 13 pgs.

"Japanese Application Serial No. 2013-527119, Response filed Oct. 1, 2015 to Office Action dated Jun. 12, 2015", 12 pgs.

"Japanese Application Serial No. 2014-024420, Preliminary Notice of Reasons for Rejection dated Feb. 24, 2015", w/ English Translation, 15 pgs.

"Knee Cartilage Implantation Carticel™, Autologous Cultured Chondrocyte Implantation", The Sports Medicine Center, [Online]. Retrieved from the Internet: <http://www.orthoassociates.com/carticel.htm>, (Apr. 6, 2006), 7 pgs.

"Letter CryoSeal FS System. Vaccines, Blood & Biologics", FDA U.S. Food and Drug Administration., http://www.fda.gov/BiologicsBioodVaccines/BioodBioodProducts/ApprovedProducts/Premarket ApprovalsPMAs/ucm091631.htm, (Jul. 26, 2007), 21 pgs.

"MarrowStim™ Concentration Kit Peripheral Arterial Disease (PAD) Study", Retrieved From Intenet : <http://www.biomet.com/patients/clinical recruitment padstudy.cfm>, (Jul. 2, 2009), 2 pgs.

"MarrowsTim™ Concentration System", Biomet Biologics, Inc, (Feb. 15, 2008), 20 pgs.

"Medical Applications: Blood Filtration", Minntech® Filtration Technologies Group, Minntech Corporation (2004), <http://www.minntech.com/ftg/industries/medical/blood_filter.html>, (Jul. 15, 2004), 1 pg.

"Minivalve international: duckbill valves—du 054.001 sd", [Online]. Retrieved from the Internet: <http://www.minivalve.com/htm/DV054.htm>, 1 pg.

"Momentive Silopren*LSR 2050", (Jun. 30, 2014), 3 pg.

"Platelet Rich Plasma (PRP)", The Stone Clinic, (May 2006), 2 pgs.

"Prosys PRP Kit", Tozai Holdings, Inc. EC21 Global B2B Marketplace, Retrieved From Internet : <http://www.ec21.com/product-details/Prosys-PRP-Kit--5467061.html Printed from Web>, (Jul. 18, 2011), 5 pgs.

"Renaflo® II Hemofilter", Minntech® Filtration Technologies Group, Minntech Corporation (2004), <http://www.minntech.com/ftg/products/renaflo/index.html>, (Jul. 15, 2004), 2 pgs.

"Sigma-Aldrich® Alkaline Phosphatase (Procedure No. 85), drug fact sheet", Sigma-Aldrich, (2003), 1-2.

"SmartPrep PRP-20 Procedure Pack—Instructions for Use", Harvest, 12 pgs.

"ThermoGenesis Corp. to Supply Autologous Thrombin Kits to Biomet, Inc", noblood: Transfusion Alternatives Patient Blood Mangement, [Online]. Retrieved from the Internet: <URL: http://noblood.org/forum/threads/2128-ThermoGenesis-Corp-to-Supply-Autologous-Thrombin-Kits-to-Biomet-Inc>, (Apr. 5, 2005), 3 pgs.

"Vernay Product Information Sheet, Umbrella Check Valve", Part No. V251010200. (Jul. 2013), 2 pgs.

Andia, Isabel, et al., "Platelet-rich plasma for managing pain and inflammation in osteoarthritis", Nature Reviews Rheumatology, vol. 9. No. 12., (Oct. 1, 2013), 721-730.

Badiavas, Evangelos V., et al., "Treatment of Chronic Wounds With Bone Marrow-Derived Cells", Arch Dermatol. 139, (Apr. 2003), 510-516.

Bang, N U, et al., "Plasma Protein Requirements for Human Platelet Aggregation", Acad Sci, 201, (1972), 280-299.

Berguer, R, et al., "Warning: fatal reaction to the use of fibrin glue in deep hepatic wounds. Case reports", J Trauma 31. (1991), 408-411.

Berruyer, M, et al., "Immunization by bovine thrombin used with fibrin glue during cardiovascular operations. Development of thrombin and factor V inhibitors", J Thorac Cardiovasc Sura 105, (1993), 892-7.

Boomgaard, et al., "Pooled Platelet Concentrates Prepared by the Platelet-Rich-Plasma Method and Filtered with Three Different Filters and Stored for 8 Days", Vox Sanq, vol. 68, (Feb. 1995), 82-89.

Brodke, et al., "Bone Grafts Prepared with Selective Cell Retention Technology Heal Canine Segmental Defects as Effectively as Autograft", SCR-Enriched Bone Grafts Heal Canine Seqmental Defects, Journal of Orthopaedic Research, (May 2006), 857-866.

Carpenter, et al., "Rationale Design of stable protein formulations-theory and practice", Rationale design of stable lyophilized protein formulations: theory and practice,, (2002), 109-133.

Casali, B, et al., "Fibrin glue from single-donation autologous plasmapheresis", Transfusion 32, (1992), 641-643.

Clayden, J D, et al., "Improved segmentation reproducibility in group tractography using a quantitative tract similarity measure", Neuroimage, Academic Press, Orlando, FL, US vol. 33, No. 2, (Nov. 1, 2006), 482-492.

Collier, B S, et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda Blood, vol. 47, No. 5, (May 1976).

Connolly, John, et al., "Development of an Osteogenic Bone-Marrow Preparation", The Journal of Bone and Joint SurQery, Incorporated. vol. 71-A, No. 5, (Jun. 1989), 684-691.

Connolly, John F., "Injectable Bone Marrow Preparations to Stimulate Osteogenic Repair", Clinical Orthopaedics and Related Research 313, (Apr. 1995), 8-18.

Dallari, et al., "In Vivo Study on the Healing of Bone Defects Treated with Bone Marrow Stromal Cells, Platelet-Rich Plasma, and Freeze-Dried Bone Allografts, Alone and in Combination", Healing of Bone Defects, Journal of Orthopaedic Research, (May 2006), 877-888.

Dayer, Jean-Michel, et al., "Adipose tissue has anti-inflammatory properties: focus on IL-1 receptor antagonist (IL-1Ra)", Annals of the New York Academy of Sciences. vol. 1069, (Jun. 2006), 444-53.

De Ugarte, et al., "Comparison of Multi-Lineage Cells from Human Adipose Tissue and Bone Marrow", Cells Tissues Organs 174, (2003), 101-109.

(56) References Cited

OTHER PUBLICATIONS

De Ugarte, et al., "Differential Expression of Stem Cell Mobilization-Associated Molecules on Multi-Lineage Cells from Adipose Tissue and Bone Marrow", Immunology Letters 89, (2003), 267-270.

De Wit, et al., "Experiments on the Preparation of Blood Components with the IBM 2991 Blood Cell Processor", Vox Sang. 29, (Feb. 10, 1975), 352-362.

Delrossi, A, et al., "Platelet-rich plasma reduces postoperative blood loss after cardiopulmonary bypass", J Thorac Cardiovasc Sura 100, (Aug. 1990), 281-285.

Depalma, L, "The preparation of fibrinogen concentrate for use as fibrin glue by four different methods", Transfusion vol. 33, No. 9, (1993), 717-720.

Deugarte, M D, et al., "Future of Fat as Raw Material for Tissue Regeneration", Lippincott Williams & Wilkins, Inc., (2007), 215-219.

Dimuzio, Paul, et al., "Development of a Tissue-Engineered Bypass Graft Seeded with Stem Cells", Vasucular, vol. 14, No. 6, (2006), 338-342.

Edlich, Richard F, et al., "Surgical Devices in Wound Healing Management", In Wound Healing: Biochemical & Clinical Aspects 1st ed., vol. Philadelphia: W.B. Saunders Company, (1992), 581-601.

Ehricke, H H, et al., "Visualizing MR diffusion tensor fields by dynamic fiber tracking and uncertainty mapping", Computers and Graphics, Elsevvier vol. 30, No. 2, (Apr. 1, 2006), 255-264.

Epstein, G H, et al., "A new autologous fibrinogen-based adhesive for otologic surgery", Ann Otol Rhinol Laryngol 95, (May 25-26, 1985), 40-45.

Fini, et al., "Effects of pulsed electromagnetic fields on articular hyaline cartilage: review of experimental and clinical studies", Biomedicine and Pharmacotherapy, Elsevier, FR, vol. 59, No. 7, (Aug. 1, 2005), 388-394.

Fraser, John K, et al., "Plasticity of human adipose stem cells toward endothelial cells and cardiomyocytes", Nature Clinical Practice Cardiovascular Medicine, vol. 3, Supplement 1, (Mar. 2006), S33-S37.

Friesen, Robert, et al., "Blood Conservation During Pediatric Cardiac Surgery: Ultrafiltration of the Extracorporeal Circuit Volume After Cardiopulmonary Bypass", Anesth, Analg, (1993), 702-707.

Galois, et al., "Cartilage Tissue Engineering: State-of-the-Art and Future Approaches", Pathol Bioi (Paris), 53—Abstract only, (Dec. 2005), 2 pgs.

Gerald, Marx, "Mechanism of Fibrin Coagulation Based on Selective, Cation-Driven, Protofibral Association", Biopolymers, vol. 27, (1988), 763-774.

Gibble, et al., "Fibrin glue: the perfect operative sealant", Transfusion, 1990, vol. 30, No. 8., (1990), 741-747.

Gimble, Jeffrey M, "Adipose-Derived Stem Cells for Regenerative Medicine", Circulation Research American Heart Association, Inc., (May 11, 2007), 1249-1260.

Gomillion, Cheryl T, et al., "Stem cells and adipose tissue engineering", Biomaterials 27, Science Direct Elsevier, (2006), 6052-6063.

Grove, et al., "Plasticity of Bone Marrow-Derived Stem Cells", Stem Cells: Concise Review, (Jan. 2004), 487-500.

Guilak, Farshid, et al., "Adipose-derived adult stem cells for cartilage tissue engineering", Biorheology 41, (2004), 389-399.

Harris, E. L.V, et al., "Protein Purification Methods—A Practical Approach", Clarification and Extraction, (1989), 7 pgs.

Hartman, A. R, et al., "Autologous whole plasma fibrin gel. Intraoperative procurement", Arch Surg 127, (Mar. 1992), 357-359.

Hattori, et al., "Osteogenic Potential of Human Adipose Tissue-Derived Stromal Cells as an Alternative Stem Cell Source", Cells Tissues Organs, (2004), 2-12.

Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.

Hennis, H L, et al., "Infectious disease risks of fibrin glue [letter]", Ophthalmic Sura 23, (Sep. 1992), 1 pg.

Hernigou, et al., "Percutaneous Autologous Bone-Marrow Grafting for Nonunions. Influence of the Number and Concentration of Progenitor Cells", Journal of Bone & Joint Surgery, (Jul. 2005), 1430-1437.

Hiromasa, Mitsuhata, et al., "An Anaphylactic Reaction to Topical Fibrin Glue", Anesthesiology, vol. 81, No. 4, (Oct. 1994), 1074-1077.

Hom, D, et al., "Promoting Healing with Recombinant Human Platelet-Derived Growth Factor-BB in a Previously Irradiated Problem Wound", The Laryngoscope, vol. 113, (Sep. 2003), 1566-1571.

Hood, Andrew G, et al., "Perioperative Autologous Sequestration III: A New Physiologic Glue with Wound Healing Properties", (Jan. 1993), 126-129.

Ishida, et al., "Platelet-Rich Plasma With Biodegradable Gelatin Hydrogel Promotes Rabbit Meniscal Tissue Regeneration", 52nd Annual Meeting of the Orthopaedic Research Society Paper No. 1035, (2006), 1 pg.

Jackson, C M, et al., "Blood coagulation", Annu Rev Biochem 49: 765-811, (1980), 22 pgs.

Jayadev, Suprya, "Trypsinization of Adherent Cells", (Aug. 8, 1991), 1 pg.

Johnstone, et al., "Autologous Mesenchymal Progenitor Cells in Articular Cartilage Repair", Clinical Orthopaedics and Related Research 367S:, (Oct. 1999), S156-S162.

Jones, D K, et al., "Confidence mapping in diffusion ensor magnetic resonance imaging tractography using a bootstrap approach", Magnetic Resonance in Medicine Wiley USA, vol. 53 , No. 5, (May 2005), 1143-1149.

Jorgensen, et al., "Stem Cells for Repair of Cartilage and Bone: The Next Challenge in Osteoarthritis and Rheumatoid Arthritis", Annals of Rheumatic Diseases, (Aug. 2000), 5 pgs.

Karpatkin, S., "Heterogeneity of Human Platelets. VI., Correlation of Platelet Function with Platelet Volume", Blood, vol. 51, No. 2, (Feb. 1978), 307-316.

Kim, Sun Jin, et al., "Development of a novel sustained release formulation of recombinant human growth homrone using sodium hyaluronate microparticles", Journal of Controlled Release, 2005, vol. 104,, (2005), 323-335.

Kjaergard, H. K, et al., "A simple method of preparation of autologous fibrin glue by means of ethanol", Surg Gynecol Obstet 175, (1992), 72-3.

Kjaergard, H. K, "Preparation of autologous fibrin glue from pericardial Blood", Ann Thorac Sur 55, (1993), 543-4.

Kohsaka, Hitoshi, "Gene Transfer Therapy for Rheumatoid Arthritis", Japanese Journal of Clinical Medicine, No. 63, No. 9, (2005), 8 pgs.

Kuderma, H. et al., "Die klinische Anwendung der Klebung van Nervenanastomosen mit Gerinnungssubstanzen bei der Rekonstruction verletzter peripherer Nerven", Wein Klin Wochenschr 87—Not in English, (Aug. 15, 1975), 6 pgs.

Kumar, Vijay, et al., "Autologous Thrombin: Intraoperative Production From Whole Blood", Journal of American Society of Extra-Corporeal Technology. JECT, 40, (2008), 94-98.

Kumar, Vijay, et al., "Stability of Human Thrombin Produced From 11 ml of Plasma Using the Thrombin Processing Device", Journal of American Society of Extra-Corporeal Technology JECT, 37, (Mar. 2005), 390-395.

Kumar, Vijay, et al., "Whole Blood Thrombin: Development of a Process for Intra-Operative Production of Human Thrombin", Journal of American Society of Extra-Corporeal Technology JECT, 39, (Apr. 2007), 18-23.

Kwon, Young-Bae, et al., "Topical application of epidermal growth factor accelerates wound healing by myofibroblast proliferation and collagen synthesis in rat", Journal of Vetrinary Science 7(2), (2006), 105-109 pgs.

Kyosti Laitakari, M D, et al., "Autologous and Homologous Fibrinogen Sealants: Adhesive Strength", Laryngoscope vol. 99, (Sep. 1989), 974-976.

Laplante, Ben L, et al., "Spine osteoarthritis", PM&R, vol. 4, (2012), S28-S36.

(56) References Cited

OTHER PUBLICATIONS

Lasher, Lisa, "My Experience with PRP", PowerPoint presentation, <http://www.cellfactortech.com/global_products.cfm>, (Sep. 16, 2005), 35 pgs.

Lendeckel, Stefan, et al., "Autologous stem cells (adipose) and fibrin glue used to treat widespread traumatic calvarial defects: case report", Journal of Cranio-Maxillofacial Surgery (2004) European Association for Cranio-Maxillofacial Surgery, (2004), 370-373.

Lerner, R, et al., "Current status of surgical adhesives", J Surg Res 48, (Feb. 1990), 165-80.

Longas, Maria O, "An Improved Method for the Purification of Human Fibrinogen", J. Biochem vol. 11, (1980), 559-564.

Lori, N F, et al., "Diffusion tensor fiber tracking of human brain connectivity: acquisition methods, reliability analysis and biological results", NMR in Biomedicine Wiley UK, vol. 15, No. 7-8, (Nov. 2002), 493-515.

Lu, X, et al., "Bone Marrow Mesenchymal Stem Cells: Progress in Bone/Cartilage Defect Repair", 19(1) Abstract, (Jan. 2002), 2 pgs.

Marx, Gerard, et al., "Heat Denaturation of Fibrinogen to Develop a Biomedical Matrix", Journal of Biomedical Materials Research Part B: Applied Biomaterials, (Apr. 2007), 49-57.

Masri, Marwan A, et al., "Isolation of Human Fibrinogen of High Purity and in High Yield Using Polyethylene Glycol 1000", Thromb Haemostas (Struttgart) vol. 49 (2), (1983), 116-119.

Matras, Helene, "Fibrin Seal: The State of the Art", Journal of Oral Maxillofacial Surgery, vol. 43, (1985), 605-611.

Matuska, et al., "Autologous Solution Protects Bovine Cartilage Explants from IL-1a and STFa-Induced Cartilage Degradation", Journal of Orthopaedic Research, (Jul. 16, 2013), 7 pgs.

Mehmet, C, et al., "Autologous Fibrin Glue From Intraoperatively Collected Platelet-Rich Plasma", Ann Thorac Surg, vol. 53, (1992), 530-531.

Molnar, Amy, "Stem Cells from Muscles Can Repair Cartilage, Study Finds Genetically Engineered Muscle-Derived Stem Cells Improved Cartilage Repair in Rats", American College of Rheumatology, (2005), 2 pgs.

Moretz, W., et al., "A simple autologous fibrinogen glue for otologic surgery", Otolarvnaol Head Neck Surg 95, (Jul. 1986), 122-4.

Nakagami, Hironori, et al., "Novel Autologous Cell Therapy in Ischemic Limb Disease Through Growth Factor Secretion by Cultured Adipose Tissue-Derived Stromal Cells", Angiogenesis by Adipose Tissue-Derived Cells, American Heart Association, Inc., (Dec. 2005), 2542-2547.

Nathan, Suresh, et al., "Cell-Based Therapy in the Repair of Osteochondral Defects: A Novel Use for Adipose Tissue", Tissue Engineering, vol. 9, No. 4, Mary Ann Liebert, Inc., (2003), 733-744.

Nilsson, et al., "Bone Repair Induced by Bone Morphogenetic Protein in Ulnar Defects in Dogs", The Journal of Bone and Joint Surgery, vol. 68 B., No. 4, (Aug. 1986), 635-642.

Okamoto, Y, et al., "Determination of soluble tumor necrosis factor-alpha receptor type (TNFRI) and II (TNFRII) in the urine of healthy Japanese subjects", Journal of Immunoassay and Immunochemistry, 2011, vol. 32, (2011), 145-155.

Orphardt, Charles E, "Denaturation of Proteins", Virtual Chembook, Elmhurst College, <http://www.elmhurst.edu/chm/vchembook/568denaturation.html> (web accessed Mar. 9, 2011), (2003), 3 pgs.

Parchment, et al., "Roles for in vitro myelotoxicity tests in preclincial drug development and clinical trial planning, Toxicology Pathology, Society of Toxicological Pathologist", vol. 21, No. 2, (1993), 241-250.

Parker, Anna M, et al., "Adipose-derived stem cell for the regeneration of damaged tissues", Expert Opinion, Cell- & Tissue-based Therapy, Expert Opin. Bioi. Ther., Informa UK Ltd, (2006), 567-578.

Planat-Benard, V., et al., "Spontaneous Cardiomyocyte Differentiation From Adipose Tissue Stroma Cells", Adipose-Derived Cell Cardiomyocyte, American Heart Association, Inc., (Feb. 6, 2004), 223-229.

Ponticiello, Michael S, "A Rapid Technique for the Isolation and Concentration of Stem Cells from Human Bone Marrow", Cell Factor Technologies, Inc., (2006), 1 pg.

Rangappa, Sunil, et al., "Transformation of Adult Mesenchymal Stem Cells Isolated From the Fatty Tissue Into Cardiomyocytes", Adult Stem Cells Transformed into Cardiomyoctyes, Ann Thorac Surg, (2003), 775-779.

Rigotti, M D, et al., "Clinical Treatment of Radiotherapy Tissue Damage by Lipoaspirate Transplant: A Healing Process Mediated by Adipose-Derived Adult Stem Cells", Plastic and Reconstructive Surgery, Breast, PRS Journal vol. 119, No. 5, Stem Cell Therapy for Angiogenesis, (Apr. 15, 2007), 1409-1422.

Robert, Quigley L, et al., "Intraoperative Procurement of Autologous Fibrin Glue", Ann Thorac Surg, vol. 56, (1993), 387-389.

Rubin, M. D., et al., "Clinical Treatment of Radiotherapy Tissue Damage by Lipoaspirate Transplant: A Healing Process Mediated by Adipose-Derived Adult Stem Cells", Plastic and Reconstructive Surgery, Discussion vol. 119, No. 5, Stem Cell Therapy for Angiogenesis, (Apr. 15, 2007), 1423-1424.

Sadeghi, M, et al., "Strikingly higher interleukin (IL)-1a, IL-1b and soluble interleukin-1 receptor antagonist (sIL-1RA) but similar IL-2, sll-2R, IL-3, IL-4, IL-6, sll-6R, IL-10, tumour necrosis factor (TNF)-a, transforming growth factor (TGF)-B2, (cont.)", (Title cont. "transforming growth factor (TGF)-(32 and interferon IFN-y urine Levels in healthy females compared to healthy males: protection against urinary tract injury?") Clinical and Experimental Immunology, vol. 142, (2005), 312-317.

Sanal, M, et al., "Does fibrin glue cause foreign body reactions?", Eu r J Pediatr Sura 2, (1992), 285-6.

Schaffler, Andreas, et al., "Concise Review: Adipose Tissue-Derived Stromal Cells—Basic and Clinical Implications for Novel Cell-Based Therapies", Tissue-Specific Stem Cells, Stem Cells®, (Apr. 10, 2007), 12 pgs.

Schmidt, K G, "Labelling of Human and Rabbit Platelets with Indium-Oxine Complex", (1979), 97-106.

Schmidt, K G, et al., "Preparation of Platelet Suspensions from Whole Blood in Buffer", Scand. J. Hoemato, 23, (1979), 88-96.

Semple, Elisabeth, et al., "Quality of Thrombin Produced From the Patient's Own Plasma Using the TPD™, a New Thrombin-Processing Device", Journal of American Society Extra-Corporeal Technology, 37(2), (2005), 196-200.

Sevenoaks, Martin J., et al, "Chronic Obstructive Pulmonary Disease, inflammation and co-morbidity—a common inflammatory phenotype?", respiratory Research vol. 7:70, (2006), 1-9.

Shiozawa, Kazuko, et al., "Gene Therapy, Is a total therapy for rheumatoid arthritis possible?", Pharma Medica, vol. 17, No. 10 w/ partial English Translation, (1999), 16 pgs.

Shu-Li, Lin, et al., "Static magnetic field attenuates mortality rate of mice by increasing the production of IL-1 receptor antagonist", Int. J. Radiat. Biol. 2009, 85(7), (Jul. 31, 2009), 633-640.

Siedentop, Karl H, et al., "Autologous Fibrin Tissue Adhesive", Laryngoscope, vol. 95, (Sep. 1985), 1074-1076.

Siedentop, Karl H, et al., "Extended Experimental and Preliminary Surgical Findings with Autologous Fibrin Tissue Adhesive Made from Patient's Own Blood", Laryngoscope, vol. 96, (Oct. 1986), 1062-1064.

Sierra, D H, "Fibrin sealant adhesive systems: a review of their chemistry, material properties and clinical applications", J Biomater Appl 7, (Apr. 1993), 309-52.

Silver, Frederick H, et al., "Review Preparation and use of fibrin glue in surgery", Biomaterials 16 (1995), (1995), 891-903.

Solem, Jan Otto, et al., "Hemoconcentration by Ultrafiltration During Open-Heart Surgery", Scand J Thor Cardiovasc Surg 22, (1988), 271-274.

Spotnitz, William D, et al., "Successful Use of Fibrin Glue During 2 Years of Surgery at a University Medical Center", The American Surgeon, vol. 55,, (Mar. 1989), 166-168.

Sutton, Robin G, et al., "Comparison of Three Blood-Processing Techniques During and After Cardiopulmonary Bypass", Ann Thorac Surg (1993) vol. 56, (1993), 6 pgs.

Takahashi, Kazutoshi, et al., "Induction of Pluripotent Stem Cells from Adult Human Fibroblasts by Defined Factors", Cell, Elsevier Inc., (Nov. 30, 2007), 1-12.

(56) References Cited

OTHER PUBLICATIONS

Tawes, Jr., Roy L, et al., "Autologous Fibrin Glue: The Last Step in Operative Hemostatis", The American Journal of Surgery, vol. 168, (Aug. 1994), 120-122.

Thompson, et al., "Fibrin Glue: A Review of Its Preparation, Efficacy, and Adverse Effects as a Topical Hemostat", Drug Intelligence and Clinical Pharmacy, vol. 22, (Dec. 1988), 946-952.

Toriumi, Dean M, et al., "Surgical Tissue Adhesives in Otolaryngology-Head and Neck Surgery", Otolaryngologic Clinics of North America, vol. 27, No. 1, (Feb. 1994), 203-209.

Weis-Fogh, U S, "Fibrinogen prepared from small blood samples for autologous use a tissue adhesive system", Eur Surg Res 20, (1988), 381-9.

Weisman, M D, "Biochemical Characterization of Autologous Fibrinogen Adhesive", Laryngoscope 97, (Oct. 1987), 1186-1190.

Wiseman, David M, et al., "Wound Dressings: Design and Use", In Wound Healing: Biochemical & Clinical Aspects 1st ed., vol., (1992), 562-580.

Yoon, Eulsik, et al., "In Vivo Osteogenic Potential of Human Adipose-Derived Stem Cells/Poly Lactide-Co-Glycolic Acid Constructs for Bone Regeneration in a Rat Critical-Sized Calvarial Defect Model", Tissue Engineering, vol. 13, No. 3, (2007), 619-627.

Zhang, Duan-Zhen, et al., "Transplantation of autologous adipose-derived stem cells ameliorates cardiac function in rabbits with myocardial infarction", Chinese Medical Journal, vol. 120, No. 4 General Hospital of Shenyang Military Region, (2007), 300-307.

Zuk, P. A, et al., "Multilineage cells from human adipose tissue: Implications for cellbased therapies", Tissue Engineering, 7(2), XP00219871 0, ISSN: 1076-3279, (Apr. 1, 2001), 211-228.

"U.S. Appl. No. 12/394,723, Non Final Office Action dated Oct. 5, 2016", 16 pgs.

"U.S. Appl. No. 12/549,116, Non Final Office Action dated Oct. 6, 2016", 15 pgs.

"U.S. Appl. No. 13/392,266, Non Final Office Action dated Oct. 4, 2016", 21 pgs.

"U.S. Appl. No. 13/837,005, Advisory Action dated Dec. 2, 2016", 3 pgs.

"U.S. Appl. No. 13/837,005, Response filed Oct. 24, 2016 Final Office Action dated Aug. 23, 2016", 9 pgs.

"U.S. Appl. No. 13/837,480, Non Final Office Action dated Sep. 13, 2016", 9 pgs.

"U.S. Appl. No. 13/837,480, Response filed Jul. 25, 2016 to Final Office Action dated May 23, 2016", 13 pgs.

"U.S. Appl. No. 13/837,480, Response filed Dec. 12, 2016 to Non Final Office Action dated Sep. 13, 2016", 13 pgs.

"U.S. Appl. No. 13/841,083, Final Office Action dated Sep. 9, 2016", 10 pgs.

"U.S. Appl. No. 13/841,083, Response filed Nov. 29, 2016 to Final Office Action dated Sep. 9, 2016", 12 pgs.

"U.S. Appl. No. 13/841,103, Final Office Action dated Dec. 14, 2016", 24 pgs.

"U.S. Appl. No. 14/050,950, Notice of Allowance dated Oct. 6, 2016", 12 pgs.

"U.S. Appl. No. 14/803,414, Restriction Requirement dated Oct. 20, 2016", 7 pgs.

"U.S. Appl. No. 14/808,828, Non Final Office Action dated Dec. 8, 2016", 10 pgs.

"U.S. Appl. No. 14/808,828, Response filed Oct. 3, 2016 to Restriction Requirement dated Aug. 2, 2016", 7 pgs.

"U.S. Appl. No. 14/830,977, Final Office Action dated Oct. 20, 2016", 12 pgs.

"U.S. Appl. No. 14/841,086, Examiners Interview Summary dated Nov. 7, 2016", 3 pgs.

"Arthritis", Mayo Clinic, (Jan. 22, 2013), 1-5.

"Canadian Application Serial No. 2,772,069, Office Action dated Jul. 20, 2016", 5 pgs.

"Chinese Application Serial No. 201480027408.6, Voluntary Amendment dated Jun. 8, 2016", W/ English Claims, 50 pgs.

"European Application Serial No. 10749582.2, Communication Pursuant to Article 94(3) EPC dated May 10, 2016", 4 pgs.

"European Application Serial No. 10749582.2, Response filed Aug. 26, 2016 to Communication Pursuant to Article 94(3) EPC dated May 10, 2016", 13 pgs.

"European Application Serial No. 14707069.2, Communication Pursuant to Article 94(3) EPC dated Nov. 15, 2016", 7 pgs.

"European Application Serial No. 14707909.9, Response filed Dec. 6, 2016 to Communication Pursuant to Article 94(3) EPC dated Jul. 22, 2016", 11 pgs.

"European Application Serial No. 14709014.6, Communication Pursuant to Article 94(3) EPC dated Oct. 20, 2016", 12 pgs.

"European Application Serial No. 14709014.6, Response filed May 27, 2016 to Office Action dated Nov. 19, 2015", 15 pgs.

"European Application Serial No. 15184504.7, Communication Pursuant to Article 94(3) EPC dated Sep. 16, 2016", 5 pgs.

"Japanese Application Serial No. 2013-527119, Examiners Decision of Final Refusal dated Oct. 18, 2016", W/ English Translation, 9 pgs.

Belal, Mahmoud Helmy, "Recombinant Human Platelet-Derived Growth Factor-BB: a promising role for fibroblast cell attachment in chronic periodontitis. A concentration-dependent effect on human cell adhesion: SEM study", Rev. Clín. Pesq. Odontol., Curitiba, v. 5, n. 3, (2009), p. 225-240.

Honore, Prisca, et al., "Interleukin-1aB gene-deficient mice show reduced nociceptive sensitivity in models of inflammatory and neuropathic pain but not post-operative pain", Behavioral Brain Research, (2006), 355-364.

Nalamachu, Srinivas, "An Overview of Pain Management: The Clinical Efficacy and Value of Treatment", Am. J. Manag. Care. 19, (2013), 261-266.

Re, Fabio, et al., "Expression of interleukin-1 receptor antagonist (IL-ra) by human circulating polymorphonuclear cells", European Journal of Immunology, 23, (1993), 570-573 pgs.

Sarzi-Puttini, Piercarlo, et al., "The Appropriate Treatment of Chronic Pain", Clin. Drug Investig. 32, (2012), 21-33.

Shrivastava, Abha, et al., "Effects of Electromagnetic Forces of Earth on Human Biological System", Indian J. Prev. Soc. Med, Retrieved from the Internet: <URL:http://medind.nic.in/ibl/t09/i3/iblt09i3p162.pdf>, (Jan. 1, 2009), 162-167.

Tiaka, Elisavet K., et al., "Epidermal Growth Factor in the Treatment of Diabetic Foot Ulcers: An Update", Perspectives in Vascular Surgery and Endovascular Therapy 24(1), (2012), p. 37-44.

Younger, Jarred, et al., "Pain Outcomes: A Brief Review of Instruments and Techniques", Curr Pain Headache Rep. 13(1), (Feb. 2009), p. 39-43.

"U.S. Appl. No. 12/394,723, Final Office Action dated May 15, 2017", 14 pgs.

"U.S. Appl. No. 13/837,005, Notice of Allowance dated May 18, 2017", 10 pgs.

"U.S. Appl. No. 13/837,480, Final Office Action dated May 4, 2017", 12 pgs.

"U.S. Appl. No. 13/837,480, Response filed Aug. 7, 2017 to Final Office Action dated May 4, 2017", 12 pgs.

"U.S. Appl. No. 13/841,083, Notice of Allowance dated Sep. 7, 2017", 8 pgs.

"U.S. Appl. No. 13/841,083, Response filed May 24, 2017 to Non Final Office Action dated Feb. 24, 2017", 18 pgs.

"U.S. Appl. No. 13/841,083, Supplemental Amendment filed Aug. 29, 2017 to Non Final Office Action dated Feb. 24, 2017", 9 pgs.

"U.S. Appl. No. 13/841,103, Examiner Interview Summary dated Jun. 8, 2017", 1 pg.

"U.S. Appl. No. 13/841,103, Non Final Office Action dated Jun. 8, 2017", 13 pgs.

"U.S. Appl. No. 13/841,103, Response filed Sep. 8, 2017 to Non Final Office Action dated Jun. 8, 2017", 12 pgs.

"U.S. Appl. No. 14/803,414, Response filed Jul. 10, 2017 to Non Final Office Action dated Apr. 19, 2017", 15 pgs.

"U.S. Appl. No. 14/808,828, Amendment Under 37 C.F.R. § 1.312 Filed", 6 pgs.

"U.S. Appl. No. 14/808,828, Notice of Allowance dated May 19, 2017", 9 pgs.

"U.S. Appl. No. 14/808,828, PTO Response to Rule 312 Communication dated Jun. 8, 2017", 2 pgs.

(56) References Cited

OTHER PUBLICATIONS

"U.S. Appl. No. 14/830,977, Non Final Office Action dated Aug. 7, 2017", 12 pgs.
"U.S. Appl. No. 15/616,548, Preliminary Amendment filed Jun. 7, 2017", 6 pgs.
"U.S. Appl. No. 15/616,548, Supplemental Preliminary Amendment Filed Aug. 17, 2017", 6 pgs.
"Chinese Application Serial No. 201480027655.6, Office Action dated May 15, 2017", (W/ English Translation), 11 pgs.
"European Application No. 14707909.9, Summons to Attend Oral Proceedings dated Aug. 10, 2017", 7 pgs.
"European Application Serial No. 10754613.7, Response filed Aug. 16, 2017 to Non Final Office Action dated Feb. 7, 2017", 20 pgs.
"European Application Serial No. 14707909.9, Response filed Apr. 26, 2017 to Communication Pursuant to Article 94(3) EPC dated Dec. 16, 2016", 25 pgs.
"European Application Serial No. 14709014.6, Summons to Attend Oral Proceedings dated Jun. 7, 2017", 8 pgs.
"European Application Serial No. 14724817.3, Office Action dated Jun. 29, 2017", 5 pgs.
"European Application Serial No. 15184504.7, Communication Pursuant to Article 94(3) EPC dated Jul. 28, 2017", 13 pgs.
"European Application Serial No. 15184504.7, Response filed Jun. 12, 2017 to Communication Pursuant to Article 94(3) EPC dated Feb. 13, 2017", 10 pgs.
Pettit, et al., "The development of site-specific drug-delivery systems for protein and peptide biopharmaceuticals", Trends in Biotechnology, (1998), 343-349.
"U.S. Appl. No. 12/394,723, Final Office Action dated May 18, 2018", 9 pgs.
"U.S. Appl. No. 12/394,723, Response filed Jun. 18, 2018 to Final Office Action dated May 18, 2018", 7 pgs.
"U.S. Appl. No. 14/830,977, Response filed May 23, 2018 to Final Office Action dated Feb. 23, 2018", 11 pgs.
"U.S. Appl. No. 14/973,913, Response filed Apr. 16, 2018 to Non Final Office Action dated Jan. 16, 2018", 12 pgs.
"U.S. Appl. No. 15/836,249, Non Final Office Action dated Apr. 6, 2018", 10 pgs.
"Australian Application Serial No. 2014237269, Response filed May 21, 2018 to First Examination Report dated Dec. 11, 2017", 25 pgs.
"Australian Application Serial No. 2014237679, Response filed Apr. 23, 2018 to First Examination Report dated Dec. 11, 2017".
"Australian Application Serial No. 2014237679, Subsequent Examiners Report dated May 29, 2018", 4 pgs.
"Australian Application Serial No. 2014238304, Response filed May 15, 2018 to First Examination Report dated Jan. 29, 2018", 50 pgs.
"Australian Application Serial No. 2014238363, Response filed May 14, 2018 to First Examination Report dated Feb. 8, 2018", 14 pgs.
"Australian Application Serial No. 2014238367, Response filed May 15, 2018 to First Examination Report dated Feb. 16, 2018", 23 pgs.
"Chinese Application Serial No. 201480027178.3, Response filed Feb. 26, 2018 to Office Action dated Oct. 10, 2017", (W/ English Claims), 10 pgs.
"Chinese Application Serial No. 201480027541.1, Office Action dated Mar. 14, 2018", (W/ English Translation), 14 pgs.
"Chinese Application Serial No. 201480027655.6, Office Action dated Feb. 23, 2018", (W/ English translation), 15 pgs.
"European Application Serial No. 10754613.7, Response filed Mar. 29, 2018 to Communication Pursuant to Article 94(3) EPC dated Nov. 28, 2017", 15 pgs.
"European Application Serial No. 14724817.3, Communication Pursuant to Article 94(3) EPC dated Apr. 5, 2018", 4 pgs.
"European Application Serial No. 18160602.1, Extended European Search Report dated Apr. 30, 2018", 9 pgs.

Botti, C, et al., "Autologous bone marrow cell therapy for peripheral arterial disease", Stem Cells and Cloning: Advances and Applications, No. 5, (2012), 5-14.
Kubis, N, et al., "Vasculogenesis and Angiogenesis: Molecular and Cellular Controls Part 1: Growth Factors", vol. 9, No. 3, (2003), 227-237.
Milkiewicz, M, et al., "Regulators of angiogenesis and strategies for their therapeutic manipulation", The International Journal of Biochemistry & Cell Biology, vol. 38, No. 3, (2006), 333-357.
Morishita, R, et al., "Safety evaluation of clinical gene therapy using hepatocyte growth factor to treat peripheral arterial disease", Hypertension, vol. 44, No. 2, (2004), 203-209.
Richard, J Powell, et al., "Safety and efficacy of patient specific intramuscular injection of HGF plasmid gene therapy on limb perfusion and wound healing in patients with ischemic lower extremity ulceration: Results of the HGF-0205 trial", Journal of Vascular Surgery, vol. 52, No. 6, (2010), 1525-1530.
"U.S. Appl. No. 12/394,723, Non Final Office Action dated Nov. 14, 2017", 18 pgs.
"U.S. Appl. No. 12/394,723, Response filed Feb. 14, 2018 to Non Final Office Action dated Nov. 14, 2017", 27 pgs.
"U.S. Appl. No. 12/394,723, Response filed Oct. 16, 2017 to Final Office Action dated May 15, 2017", 18 pgs.
"U.S. Appl. No. 13/837,480, Non Final Office Action dated Dec. 8, 2017", 9 pgs.
"U.S. Appl. No. 13/837,480, Response filed Mar. 8, 2018 to Non Final Office Action dated Dec. 8, 2017", 13 pgs.
"U.S. Appl. No. 13/841,103, Notice of Allowance dated Oct. 11, 2017", 8 pgs.
"U.S. Appl. No. 13/841,103, Supplemental Preliminary Amendment filed Sep. 26, 2017", 7 pgs.
"U.S. Appl. No. 14/803,414, Final Office Action dated Oct. 18, 2017", 26 pgs.
"U.S. Appl. No. 14/803,414, Response field Dec. 18, 2017 to Final Office Action dated Oct. 18, 2017", 13 pgs.
"U.S. Appl. No. 14/830,977, Final Office Action dated Feb. 23, 2018", 10 pgs.
"U.S. Appl. No. 14/830,977, Response filed Nov. 6, 2017 to Non Final Office Action dated Aug. 7, 2017", 13 pgs.
"U.S. Appl. No. 14/973,913, Non Final Office Action dated Jan. 16, 2018", 7 pgs.
"U.S. Appl. No. 14/973,913, Response filed Dec. 20, 2017 to Restriction Requirement dated Oct. 20, 2017", 8 pgs.
"U.S. Appl. No. 14/973,913, Restriction Requirement dated Oct. 20, 2017", 7 pgs.
"U.S. Appl. No. 15/836,249, Preliminary Amendment filed Mar. 9, 2018", 9 pgs.
"Australian Application Serial No. 2014229070, First Examination Report dated Nov. 24, 2017", 3 pgs.
"Australian Application Serial No. 2014229070, Response filed Jan. 15, 2018 to First Examination Report dated Nov. 24, 2017", 25 pgs.
"Australian Application Serial No. 2014237269, First Examination Report dated Dec. 11, 2017", 6 pgs.
"Australian Application Serial No. 2014237679, First Examination Report dated Dec. 11, 2017", 4 pgs.
"Australian Application Serial No. 2014238304, First Examination Report dated Jan. 29, 2018", 4 pgs.
"Australian Application Serial No. 2014238363, First Examination Report dated Feb. 8, 2018", 3 pgs.
"Australian Application Serial No. 2014238367, First Examination Report dated Feb. 16, 2018", 3 pgs.
"Chinese Application Serial No. 201480027178.3, Office Action dated Oct. 10, 2017", W/ English Translation, 14 pgs.
"Chinese Application Serial No. 201480027655.6, Response filed Oct. 9, 2017 to Office Action dated May 15, 2017", W/ English Translation of Claims, 9 pgs.
"European Application Serial No. 10754613.7, Communication Pursuant to Article 94(3) EPC dated Nov. 28, 2017", 3 pgs.
"European Application Serial No. 14707909.9, Summons to Attend Oral Proceedings dated Oct. 18, 2017", 2 pgs.
"European Application Serial No. 14709014.6, Summons to Attend Oral Proceedings dated Oct. 18, 2017", 2 pgs.

(56) References Cited

OTHER PUBLICATIONS

"European Application Serial No. 14714491.9, Communication Pursuant to Article 94(3) EPC dated Feb. 8, 2018", 6 pgs.
"European Application Serial No. 14714491.9, Response filed Oct. 16, 2017 to Non Final Office Action dated Feb. 28, 2017", 18 pgs.
"European Application Serial No. 14724817.3, Response filed Nov. 9, 2017 to Office Action dated Jun. 29, 2017", 19 pgs.
"European Application Serial No. 14729994.5, Communication Pursuant to Article 94(3) EPC dated Oct. 10, 2017", 8 pgs.
Bendinelli, Paola, et al., "Molecular Basis of Anti-Inflammatory Action of Platelet-Rich Plasma on Human Chondrocytes: Mechanisms of NF-kB Inhibition Via HGF", Journal of Cellular Physiology 225, (2010), 757-766.
Le Meur, Yannick, et al., "Whole blood production of monocytic cytokines (IL-1β, IL-6, TNF-a, sIL-6R, IL-1Ra) in haemodialysed patients", Nephrology Dialysis Transplantation; 14, (1999), pp. 2420-2426.
Ulich, Thomas R., et al., "Endotoxin-Induced Cytokine Gene Expression in Vivo: IV. Expression of Interleukin-1 a/ß and Interleukin-1 Receptor Antagonist mRNA During Endotoxemia and During Endotoxin-initiated Local Acute Inflammation", American Journal of Pathology, vol. 141, No. 1, (Jul. 1992), pp. 61-68.
Woodell-May, J. et al. "Producing Accurate Platelet Counts for Platelet Rich Plasma: Validation of a Hematology Analyzer and Preparation Techniques for Counting" Scientific Foundation, Journal of Carniofacial Surgery, vol. 16, No. 5 (pp. 749-756) Sep. 2005.
Woodell-May, J. et al. Autologous protein solution inhibits MMP-13 production by IL-1beta and TNFalpha-stimulated human articular chondrocytes. J Orthop Res Sep. 15, 2011; 29:1320-6.
Wright-Carpenter, T. "Treatment of Muscle Injuries by Local Administration of Autologous Conditioned Serum: A Pilot Study on Sportsmen with Muscle Strains" Int J Sports Med, vol. 25 (pp. 588-593) Oct. 2004.
Yang, S. et al. "Protective effects of IL-1Ra or vIL-10 gene transfer on a murine model of wear debris-induced osteolysis" Gene Therapy, vol. 11 (pp. 483-491) 2004.
Yang, T. et al. "Recent Applications of Polyacrylamide as Biomaterials" Recent Patents on Materials Science, vol. 1 (pp. 29-40) 2008.
Yoshida S. et al. "Elevation of serum soluble tumour necrosis factor (TNF) receptor and IL-1 receptor antagonist levels in bronchial asthma" Clinical and Experimental Immunology, Wiley-Blackwell Publishing Ltd. vol. 106, No. 1, Oct. 1996.
Zhang et al."IL-1ra alleviates inflammatory hyperalgesia through preventing phosphorylation of NMDA receptor NR-1 subunit in rats" PAIN. vol. 135, No. 3, Mar. 5, 2008, pp. 232-239.
"Australian Application Serial No. 2014237269, Response filed Jul. 28, 2018 to Subsequent Examiners Report dated Jun. 29, 2018", 15 pgs.
"Australian Application Serial No. 2014237269, Subsequent Examiners Report dated Jun. 29, 2018", 10 pgs.
"Australian Application Serial No. 2014237679, Response filed Jul. 19, 2018 to Subsequent Examiners Report dated May 29, 2018", 54 pgs.
"Australian Application Serial No. 2014238304, Subsequent Examiners Report dated Jun. 9, 2018", 3 pgs.
"Chinese Application Serial No. 201480027178.3, Office Action dated Jun. 15, 2018", w/ English translation, 9 pgs.
"European Application Serial No. 10754613.7, Communication Pursuant to Article 94(3) EPC dated Jun. 26, 2018", 3 pgs.
"U.S. Appl. No. 12/394,723, Corrected Notice of Allowability dated Jul. 30, 2018", 5 pgs.
"U.S. Appl. No. 12/394,723, Notice of Allowance dated Jul. 17, 2018", 10 pgs.
"U.S. Appl. No. 13/837,480, Notice of Allowance dated Jun. 28, 2018", 7 pgs.
"U.S. Appl. No. 14/973,913, Final Office Action dated Aug. 9, 2018", 11 pgs.
"U.S. Appl. No. 15/836,249, Response filed Jul. 2, 2018 to Non Final Office Action dated Apr. 6, 2018", 11 pgs.
U.S. Appl. No. 14/271,722, filed May 7, 2014, Higgins et al.
U.S. Appl. No. 13/840,562, filed Mar. 15, 2013, Binder et al.
U.S. Appl. No. 13/841,083, filed Mar. 15, 2013, Landrigan et al.
U.S. Appl. No. 13/837,005, filed Mar. 15, 2013, Woodell-May et al.
U.S. Appl. No. 13/837,480, filed Mar. 15, 2013, O'Shaughnessey et al.
U.S. Appl. No. 13/840,129, filed Mar. 15, 2013, Matuska et al.
U.S. Appl. No. 13/841,103, filed Mar. 15, 2013, Landrigan et al.
U.S. Appl. No. 15/836,249, filed Dec. 8, 2017, Treatment of Peripheral Vascular Disease Using Protein Solutions.

* cited by examiner

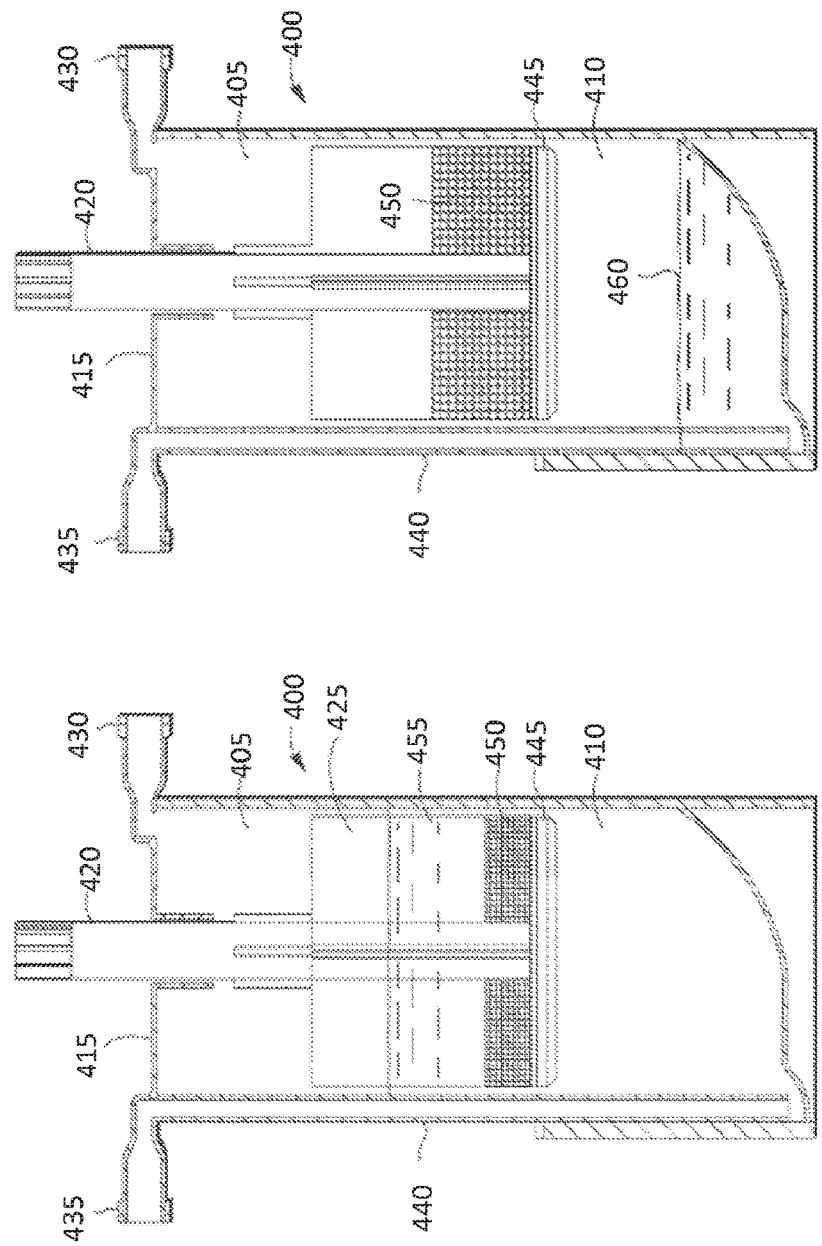

METHODS FOR MAKING CYTOKINE COMPOSITIONS FROM TISSUES USING NON-CENTRIFUGAL METHODS

INTRODUCTION

The present technology relates to methods of treating inflammatory disorders, including osteoarthritis. In particular, methods comprise use of solutions comprising cytokines, including such solutions derived from blood fractions obtained by non-centrifugal methods.

Inflammation is a complex cellular and biochemical process that occurs in the affected blood vessels and adjacent tissues in response to an injury or abnormal stimulation caused by a physical, chemical, or biologic agent, such as a pathogen, allergen or irritant. The inflammatory process includes local reactions and resulting morphologic changes in tissue; the destruction or removal of the causative agent; and the responses that lead to repair and healing. In most instances, inflammation is a beneficial and transient process, which subsides as the body attacks and overcomes an infectious or other harmful agent. However, in some instances, inflammation can be chronic self-perpetuating process, for example, as part of an ongoing degenerative process (such as arthritis) or autoimmune disease, leading to destruction of tissue. Chronic inflammation is associated with a variety of disorders, including rheumatoid arthritis, atherosclerosis, ischemic heart disease, periodontitis, colitis, and some cancers.

An inflammatory response consists of a cascade of biochemical events, involving the local vascular system and immune system, and various cells within the injured tissue. The process involves the release of numerous cell-derived mediators, including histamine, interferon-gamma, interleukin-8, leukotriene, nitric oxide, prostaglandins, tumor necrosis factor-alpha, and interleukin-1. In particular, interleukin-1 (IL-1) includes a family of cytokines that can stimulate lymphocytes and macrophages, activate phagocytes, increase prostaglandin production, contribute to degeneration of bone joints, increase bone marrow cell proliferation, and are involved in many chronic inflammatory conditions. IL-1 can be generated by macrophages, monocytes, and dendritic cells, and can be part of the inflammatory response against infection.

The mode of action of IL-1 can be mediated by interleukin-1 receptor antagonist protein (IL-1ra; also known as "IRAP"). IL-1ra binds to the same receptor on the cell surface as IL-1, and thus prevents IL-1 from sending a signal to that cell. IL-1ra is secreted from white blood cells, including monocytes, macrophages, neutrophils, polymorphonuclear cells (PMNs), and other cells, and can modulate a variety of IL-1 related immune and inflammatory responses, as described by Arend W P, Malyak M, Guthridge C J, Gabay C (1998) "Interleukin-1 receptor antagonist: role in biology" Annu. Rev. Immunol. 16: 27-55. Production of IL-1ra is stimulated by several substances including adherent immunoglobulin G (IgG), other cytokines, and bacterial or viral components. IL-1ra, as well as other cytokines such as soluble tumor necrosis factor receptor 1 (sTNF-R1), soluble tumor necrosis factor receptor 2 (sTNF-R2) and (soluble interleukin receptor II (sIL-1RII), is an important natural anti-inflammatory protein in arthritis, colitis, and granulomatous pulmonary disease.

IL-1ra can be used in the treatment of rheumatoid arthritis, an autoimmune disease in which IL-1 plays a key role, reducing inflammation and cartilage degradation associated with the disease. For example, Kineret™ (anakinra) is a recombinant, non-glycosylated form of IL-1ra (Amgen Manufacturing, Ltd., Thousand Oaks, Calif.). Various recombinant interleukin-1 inhibitors and methods of treatment are described in U.S. Pat. No. 6,599,873, Sommer et al., issued Jul. 29, 2003; U.S. Pat. No. 5,075,222, Hannum et al., issued Dec. 24, 1991; and U.S. Application Publication No. 2005/0197293, Mellis et al., published Sep. 8, 2005 In addition, methods for producing IL-1ra from body fluids, including the use of autologous fluids, are described in U.S. Pat. No. 6,623,472, Reinecke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004.

Many such treatments for inflammation are known in the art. Therapies known in the art may be directed to removal of the underlying irritant or agent causing the inflammatory reaction, or by mediating one or more aspects of the inflammatory response. Examples include glucocorticoid steroids (such as hydrocortisone, cortisone, prednisone, and beclomethasone), non-steroidal anti-inflammatory drugs (such as aspirin, ibuprofen and naproxen), and immune selective anti-inflammatories. However, many such treatments present side effects, particularly during chronic administration, or have pharmacologic characteristics that limit their use. For example, while compositions and methods using IL-1ra are known in the art, they may be associated with issues regarding stability and half-life of IL-1ra as well as the amount and rate of IL-1ra provided. Moreover, many treatments do nothing to address the underlying causes of the inflammatory process. Accordingly, improved methods of treating inflammation are needed, offering one or more of improved efficacy, reduced side effects, and improved dosing characteristics.

SUMMARY

The present technology provides methods for generating solutions rich in anti-inflammatory cytokines for use in treatment of inflammation and other disorders mediated by interleukin-1 and tumor necrosis factor-alpha. Methods for generating such solutions include contacting a liquid volume of cytokine-producing cells with a solid extraction material, removing the solid extraction material from the liquid, and freeze drying the liquid. The liquid volume of cytokine-producing cells is obtained from whole blood by non-centrifugal methods, such as filtration, antibody binding, and electrophoretic methods. Thus, the present technology provides methods for generating a solution rich in interleukin-1 receptor antagonist (IL-1ra) comprising:

(a) obtaining a cytokine cell suspension, such as cytokine-producing cells, by separating cytokine-producing cells from a tissue comprising cytokine-producing cells using a non-centrifugal process;

(b) contacting the cytokine cell suspension with a solid extraction material; and (c) separating the liquid from the solid extraction material to obtain the solution rich in IL-1ra.

The tissue comprising cytokine-producing cells may be selected from the group consisting of whole blood, bone marrow aspirate, adipose tissue, fractions thereof, and mixtures thereof.

In various embodiments, the anti-inflammatory cytokine composition comprises (i) interleukin-1 receptor antagonist (IL-1ra) at a concentration of at least about 10,000 pg/ml;

(ii) soluble Tumor Necrosis Factor Receptor 1 (sTNF-R1) at a concentration of at least about 1,200 pg/ml; and (iii) a protein selected from the group consisting of sTNF-RII, IGF-I, EGF, HGF, PDGF-AB, PDGF-BB, VEGF, TGF-β1, and sIL-1RII, and mixtures thereof, wherein the concentration of the protein in the composition is greater than the concentration of the protein in normal blood.

In some embodiments, the compositions additionally comprise white blood cells, platelets, or combinations thereof. The present technology also provides methods of treating a condition mediated by interleukin-1 receptor, such as inflammation, in a human or other mammalian subject, comprising topical administration of a composition of the present technology.

BRIEF DESCRIPTION OF THE DRAWINGS

FIGS. 2A and 2B show a device for activating a sample to generate anti-inflammatory cytokines, before (FIG. 2A) and after (FIG. 2B) centrifugation.

Figures 1A, 1B:
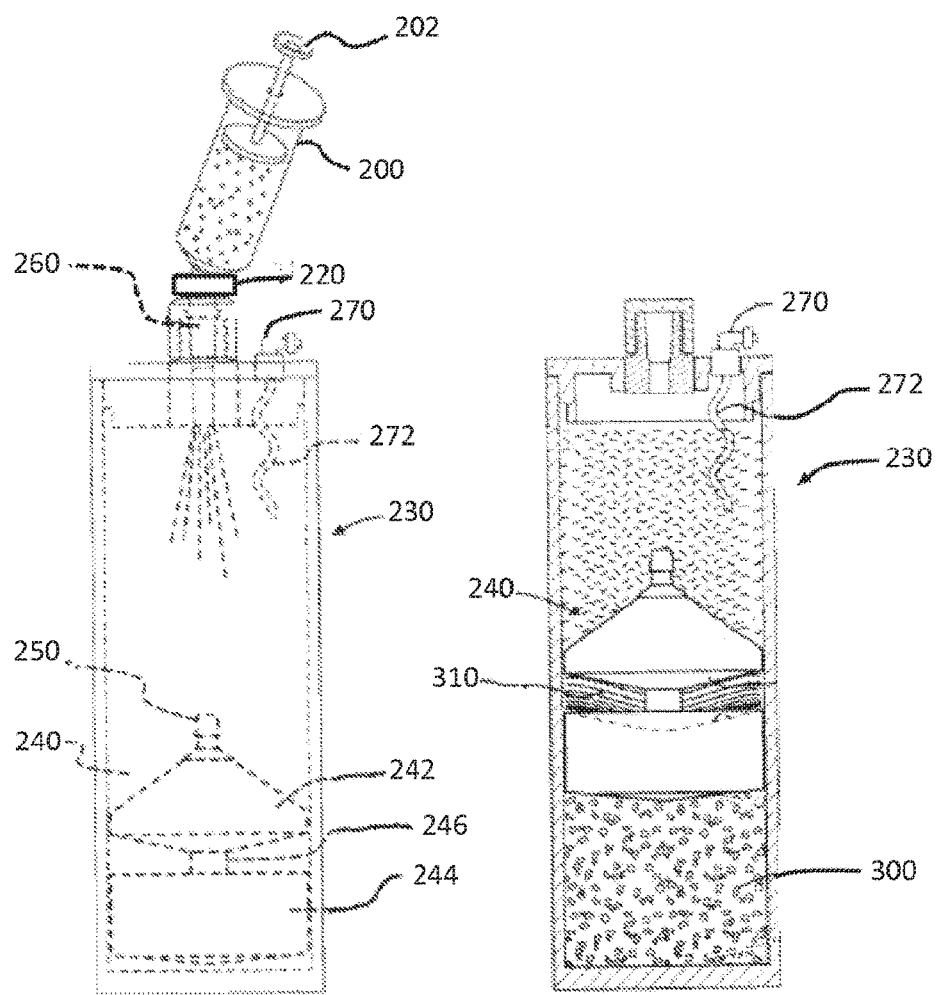
FIGS. 1A-1D show a plan view of a device for making a suspension of white blood cells, before (FIG. 1A) and after (FIG. 1B) centrifugation, and during withdrawal (FIGS. 1C and 1D)

Corresponding reference numerals indicate corresponding parts throughout the several views of the drawings. It should be noted that the figures set forth herein are intended to exemplify the general characteristics of materials, compositions, devices, and methods among those of the present technology, for the purpose of the description of certain embodiments. These figures may not precisely reflect the characteristics of any given embodiment, and are not necessarily intended to fully define or limit specific embodiments within the scope of this technology.

DESCRIPTION

The following description of technology is merely exemplary in nature of the composition, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology relates to compositions, methods of making compositions, and methods of using compositions for the treatment of inflammatory disorders, and other disorders mediated by interleukin-1. In general, such compositions are made by a process comprising:
(a) obtaining a cytokine cell suspension (a "cytokine cell suspension," as discussed further below) by separating cytokine-producing cells from a tissue comprising cytokine-producing cells using a non-centrifugal process; and
(b) fractionating the liquid to produce a protein solution comprising one or more proteins, such as interleukin-1 receptor antagonist.

Protein Compositions

The present technology provides methods for treating inflammatory disorders other disorders mediated by interleukin-1 in humans or other mammalian subjects using compositions (herein referred to as "Protein Solutions") comprising proteins dissolved, suspended or otherwise carried for delivery to a mammalian subject in a physiologically-acceptable medium. In various embodiments, such compositions comprise proteins (e.g., cytokines) that are native to whole blood in normal mammal subjects. Such compositions may also contain viable cells, including platelets, white blood cells, and combinations thereof.

In various embodiments, the Protein Solution comprises at least two proteins selected from the group consisting of IL-1ra, sTNF-RI, sTNF-RII (soluble tumor necrosis factor-receptor 2), IGF-I (insulin-like growth factor 1), EGF (epidermal growth factor), HGF (hepatocyte growth factor), PDGF-AB (platelet-derived growth factor AB), PDGF-BB (platelet-derived growth factor BB), VEGF (vascular endothelial growth factor), TGF-β1 (transforming growth factor-β1, and sIL-1RII (soluble interleukin receptor II), wherein the concentration of each protein in the composition is greater than the concentration of the protein in normal blood. While the concentration of every such protein in the composition may be greater than its respective concentrations in in normal blood, it is not necessary that the concentration of more than two of the proteins be greater than their respective concentrations in normal blood.

In various embodiments, the platelet-rich protein solution comprises the following components.

TABLE 1

Protein Solution Exemplary Protein Components

| Component | Composition Concentration | Normal Whole Blood Concentration |
| --- | --- | --- |
| plasma proteins (total) | about 80 mg/ml or greater<br>about 100 mg/ml or greater<br>about 200 mg/ml or greater<br>about 250 mg/ml or greater | about 67 mg/ml |
| albumin | about 60 mg/ml or greater<br>about 100 mg/ml of greater | about 56 mg/ml |
| fibrinogen | about 3.2 mg/ml or greater<br>about 4 mg/ml or greater | about 2.9 mg/ml |
| IL-1ra | about 10,000 pg/ml or greater<br>about 25,000 pg/ml or greater<br>about 30,000 pg/ml or greater<br>from about 25,000 to about 110,000 pg/ml<br>from about 25,000 to about 40,000 pg/ml | about 4200 pg/ml |
| sTNF-RI | about 1,200 pg/ml or greater<br>about 1,800 pg/ml or greater<br>about 3,000 pg/ml or greater | about 630 pg/ml |
| sTNF-RII | about 3,000 pg/ml or greater<br>about 5,000 pg/ml or greater<br>about 7,000 pg/ml or greater<br>about 9,000 pg/ml or greater | about 1200 pg/ml |
| sIL-1RII | about 15,000 pg/ml or greater<br>about 20,000 pg/ml or greater<br>about 25,000 pg/ml or greater | about 11,800 pg/ml |
| Growth factors | | |
| EGF | about 800 pg/ml or greater<br>about 1,000 pg/ml or greater<br>about 1,200 pg/ml or greater | about 250 pg/ml |
| HGF | about 1,000 pg/ml or greater<br>about 2,500 pg/ml or greater<br>about 2,800 pg/ml or greater<br>about 3,000 pg/ml or greater | about 500 pg/ml |
| PDGF-AB | about 35,000 pg/ml or greater<br>about 50,000 pg/ml or greater<br>about 70,000 pg/ml or greater | about 6,000 pg/ml |
| PDGF-BB | about 10,000 pg/ml or greater<br>about 15,000 pg/ml or greater<br>about 20,000 pg/ml or greater | about 1,500 pg/ml |
| TGF-β1 | about 100,000 pg/ml or greater<br>about 150,000 pg/ml or greater<br>about 190,000 pg/ml or greater | about 10,000 pg/ml |
| IGF-1 | about 130,000 pg/ml or greater<br>about 150,000 pg/ml or greater<br>about 160,000 pg/ml or greater | about 70,000 pg/ml |

TABLE 1-continued

Protein Solution Exemplary Protein Components

| Component | Composition Concentration | Normal Whole Blood Concentration |
|---|---|---|
| VEGF | about 500 pg/ml or greater<br>about 600 pg/ml or greater<br>about 800 pg/ml or greater | about 150 pg/ml |

Protein concentrations can be measured using the methods known in the art. For example, Quantikine® human immunoassays (R&D Systems, Inc., Minneapolis, Minn.) may be used to assay for IL-1ra, IL-1β, IL-8, sTNF-RI, TNF-α, IL-6, sTNF-RII, IL-10, IL-13, and IL-4, according to the manufacturer's instructions. Immunoassays may be performed for hepatocyte growth factor and soluble IL-1RII.

The composition further preferably comprises viable white blood cells, lysed white blood cells, or both. In a preferred composition, the Protein Solution comprises monocytes, granulocytes, and platelets. In various embodiments, a Protein Solution comprises the following components.

TABLE 2

Protein Solution Exemplary Cellular Components

| Component | Composition Concentration | Normal Whole Blood Concentration |
|---|---|---|
| white blood cells | at least about 15 k/μl<br>at least about 30 k/μl<br>from about 30 to about 60 k/μl<br>from about 40 to about 50 k/μl | 6.5 k/μl |
| red blood cells | less than about 3 M/μl<br>less than about 2 M/μl<br>less than about 2.5 M/μl | 4.5 M/μl |
| platelets | at least about 400 k/μl<br>at least about 800 k/μl<br>at least about 1,000 k/μl | 240 k/μl |
| neutrophils | at least about 5 k/μl<br>at least about 10 k/μl<br>at least about 12 k/μl | 3.7 k/μl |
| monocytes | at least about 1 k/μl<br>at least about 2 k/μl<br>at least about 3 k/μl | 0.5 k/μl |
| lymphocytes | at least about 5 k/μl<br>at least about 10 k/μl<br>at least about 20 k/μl | 2 k/μl |
| eosinophiles | at least about 0.15 k/μl<br>at least about 0.18 k/μl | 0.1 k/μl |
| basophils | at least about 0.2 k/μl<br>at least about 0.4 k/μl<br>at least about 0.6 k/μl | 0.1 k/μl |

It will be understood that this concentration is species specific. Further, it is understood that concentrations may vary among individual subjects. Thus, in methods comprising production of a Protein Solution from the blood or other tissue containing cytokine-producing cells, the concentration of proteins and cells in the Protein Solution may vary from those recited above; the values recited above are mean values for concentrations as may be seen in a population of subjects.

In various embodiments, the concentration of one or more of the proteins or other components in the Protein Solution is greater than the concentration of the component in normal blood. (Compositions with such higher concentrations of components are said to be "rich" in such components.) As referred to herein, the concentration of a component in "normal" blood or other tissue is the concentration found in the general population of mammalian subjects from which the tissue is obtained, e.g., in normal whole blood. In methods wherein the anti-inflammatory cytokine composition is derived from tissue from a specific subject, the "normal" concentration of a protein or cell may be the concentration in the blood of that individual before processing is performed to derive the protein or cell.

Thus, in various embodiments, the concentration of one or more components of the Protein Solution is greater than about 1.5 times, about 2 times, or about 3 times, greater than the concentration of the component in normal blood. For example, components may have greater concentrations in the compositions, relative to normal (whole) blood, as follows:

IL-1ra, at a concentration that is at least about 2.5, or at least about 3 or at least about 5, times greater;
sTNF-RI, at a concentration that is at least about 2, or at least about 2.5 or at least about 3, times greater;
sTNF-RII, at a concentration that is at least about 2, or at least about 2.5 or at least about 3, times greater;
sIL-1RII, at a concentration that is at least about 1.5, or at least about 1.8 or at least about 2, times greater;
EGF, at a concentration that is at least about 2, or at least about 3 or at least about 5, times greater;
HGF, at a concentration that is at least about 2, or at least about 3 or at least about 4, times greater;
PDGF-AB, at a concentration that is at least about 2, or at least about 3 or at least about 5, times greater;
PDGF-BB, at a concentration that is at least about 2, or at least about 3 or at least about 5, times greater;
TGF-β1, at a concentration that is at least about 3, or at least about 4 or at least about 6, times greater;
IGF-1, at a concentration that is at least about 1.2, or at least about 1.4 or at least about 1.5, times greater;
VEGF, at a concentration that is at least about 2, or at least about 2.5 or at least about 3, times greater;
white blood cells, at a concentration that is at least about 2, or at least about 3 or at least about 4, times greater;
platelets, at a concentration that is at least about 2, or at least about 3 or at least about 4, times greater;
neutrophils, at a concentration that is at least 1.5, or at least 2 or at least about 3, times greater;
monocytes, at a concentration that is at least about 3, or at least about 4 or at least about 6, times greater;
lymphocytes, at a concentration that is at least 5, or at least 8 or at least 10, times greater; and
basophils, at a concentration that is at least about 2, or at least about 4 or at least 6, times greater Also, the concentration of erythrocytes in the Protein Solution is preferably at least half, or at least a third, of the concentration of erythrocytes in normal blood.

For example, a Protein Solution may comprise:
(a) at least about 10,000 pg/ml IL1-ra;
(b) at least about 1,200 pg/ml sTNF-RI; and
(c) a protein selected from the group consisting of sTNF-RII, IGF-I, EGF, HGF, PDGF-AB, PDGF-BB, VEGF, TGF-β1, and sIL-1RII, and mixtures thereof,
wherein the protein has a concentration higher than the protein's baseline concentration in normal blood. In another example, a Protein Solution comprises:
(a) interleukin-1 receptor antagonist (IL-1ra), at a concentration at least 3 times greater than the concentration of IL-1ra in normal blood;
(b) soluble tissue necrosis factor-r1 (sTNF-r1), at a concentration at least 2 times greater than the concentration of IL-1ra in normal blood;

(c) white blood cells at a concentration at least 2 times greater than the concentration of white blood cells in normal blood; and (d) platelets, at a concentration at least 2 times greater than the concentration of platelets in normal blood.

In some embodiments, the concentration of IL-1ra in the Protein Solution is preferably at least 5,000, or at least 10,000, times greater than the concentration of interleukin-1α in the Protein Solution. The ratio of IL-1ra:interleukin-1β (IL-1β) concentrations is preferably at least 100. In some embodiments, the concentration of IL-1ra in the Protein Solution is preferably at least 1500, or at least 8000, times greater than the concentration of IL-1β in the Protein Solution. The ratio of sIL-1RII:interleukin-1β (IL-1β) concentrations is preferably greater than 1. In some embodiments, the sIL-1RII in the Protein Solution is preferably at least 2000, or at least 45000, times greater the concentration of interleukin-1β in the Protein Solution.

The present technology provides Protein Solutions wherein one or more components of the Protein Solution are obtained from non-autologous sources, such as through recombinant or synthetic methods, or by isolation from allogeneic sources (i.e., from subjects of the same species as the subject to whom the solution is to be administered) or xenogeneic sources (i.e., from animal sources other than the species to whom the solution is to be administered). In some embodiments, the Protein Solutions consists, or consists essentially, of such allogeneic components. However, in various embodiments, the Protein Solution comprises one or more components (e.g., platelets) derived from the subject to whom the solution is to be administered in a treatment methods according to this technology. Such components are, accordingly, "autologous." In some embodiments, the Protein Solution comprises mixtures of autologous and allogeneic components.

Methods of Making Protein Solutions

As discussed above, the Protein Solution is made by fractionating a liquid comprising cytokine-producing cells, to produce a protein solution comprising cytokines, such as IL1-ra. In various embodiments, Protein Solutions are made by derivation of one or more components from tissue comprising cytokine-producing cells. As referred to herein, a "cytokine producing tissue" is a tissue obtained from a mammalian subject, comprising cells that are capable of producing cytokines. Such cells include white blood cells, adipose stromal cells, bone marrow stromal cells, and combinations thereof. It is understood that white blood cells include monocytes, lymphocytes, and granulocytes such as neutrophils, eosinophils, and basophils. White blood cell useful in the methods of this technology preferably include monocytes and neutrophils. Cytokine producing tissues among those useful herein include blood, adipose tissue, bone marrow, and fractions thereof, as further discussed below.

Blood useful herein includes whole blood, plasma, platelet-rich plasma, platelet-poor plasma, and blood clots. In a preferred embodiment, methods of the present technology use platelet-rich plasma (PRP), containing white blood cells and platelets, comprising the buffy coat layer created by sedimentation of whole blood. Adipose tissue useful herein includes any fat tissue, including white and brown adipose tissue, which may be derived from subcutaneous, omental/visceral, mammary, gonadal, or other adipose tissue sites. Bone marrow useful herein includes red marrow and yellow marrow. In a preferred embodiment, bone marrow is bone marrow concentrate, obtained from the red marrow of long bones, comprising hematopoietic and mesenchymal stems cells. As discussed above, compositions of the present technology may be made from blood, adipose, and bone marrow tissue from allogeneic sources, relative to the subject to be treated according to methods of this technology. Compositions may also be made from combinations of allogeneic and autologous tissues.

In some embodiments, methods comprise fractionating a liquid (a "cytokine cell suspension.") comprising cells capable of producing cytokines, such as IL1-ra and sTNF-R1. As discussed above, such cells include white blood cells, adipose stromal cells, bone marrow stromal cells, and combinations thereof. In some embodiments, the cytokine cell suspension is a liquid comprising white blood cells. It should be understood that the cytokine cell suspension comprises cells and an extra-cellular liquid, regardless of the relative proportions of the cells and liquid. In some embodiments, the suspension may comprise primarily cells, with liquid being present as only a minor component, essentially wetting the cells. In some embodiments, the liquid may comprise two phases, consisting of a phase primarily consisting of liquid and a phase primarily consisting of cells, forming a suspension of cells in the liquid only upon agitation or other mixing.

Obtaining a Cytokine Cell Suspension

Obtaining cytokine-producing cells may be performed directly in some methods of this technology, whereby a health care practitioner or other individual performs isolation, processing, or other processes for creating the liquid, in a procedure that includes the contacting and isolating steps. In some embodiments, the processes for creating the liquid are performed contemporaneously with the contacting and isolating steps, as part of a point-of-care procedure, as discussed further herein. Alternatively, obtaining the liquid may be indirect, involving only the acquisition of the liquid for use in the contacting and isolating steps, wherein the processing to create the liquid has previously been performed by another party.

As discussed above, the methods of this technology comprise obtaining a liquid comprising cytokine-producing cells by non-centrifugal processing of a tissue containing cytokine-producing cells (e.g., white blood cells), obtained from a mammalian subject. As referred to herein, a "non-centrifugal method" comprises a process for obtaining tissue fractions comprising cytokine-producing cells from tissue without use of a centrifuge. In some embodiments, methods are "non-gravimetric," wherein, based on physical, chemical or physicochemical properties of the cells other than density, wherein the concentration of white blood cells in the fraction are higher than the concentration of white blood cells in the tissue. Such non-gravimetric methods are, in particular, distinguished from methods wherein a white blood cell fraction is created by centrifugation of whole blood or other tissue. In some embodiments, the non-centrifugal method comprises a process solely based on such properties of white blood cells other than density.

In some embodiments, non-centrifugal methods useful herein include obtaining a volume of cytokine-producing cells and suspending the volume in a suitable medium for subsequent processing in the methods of this technology. In other embodiments, a fraction of cytokine-producing cells is isolated from tissue, wherein the fraction comprises cytokine-producing cells in the medium suitable for subsequent processing. The medium may be constituted so as to maintain viability of the cytokine-producing cells, including physiological saline and serum. Thus, in various embodiments, methods comprise:
  (a) mixing a volume of cytokine-producing cells with a liquid medium to form a cytokine cell suspension;
  (b) contacting the cytokine cell suspension a solid extraction material; and
  (c) separating liquid from the polyacrylamide beads to obtain a solution rich in IL-1ra.

As further discussed below, the volume of cytokine-producing cells may be made by a process comprising one or more of:
  (a) expressing a tissue comprising cytokine-producing cells through a hollow fiber apparatus, forming a liquid volume comprising cytokine-producing cells;
  (b) separation of cytokine-producing cells from whole blood using a density gradient aid;
  (c) electrophoresis; and
  (d) binding of cytokine-producing cells to antibody conjugated beads.

A cytokine cell suspension may be prepared by admixing cells with a suitable liquid, using methods known in the art. For example, white blood cells may be isolated from whole blood by lysing red blood cells or by centrifugation of whole blood utilizing a density gradient aid. An example of a suitable density gradient aid is Ficoll-Paque™ PLUS medium (GE Healthcare Bio-Sciences, Piscataway, N.J., USA), which comprises a hydrophilic polysaccharide which aggregates red blood cells. For example, in such a method, whole blood may be diluted 1:1 with an appropriate buffer, such as phosphate buffered saline (PBS), in a container. A volume of Ficoll-Paque™ PLUS medium is added to a centrifuge tube. The whole blood:PBS mixture is then gently layered on top of the Ficoll-Paque™ PLUS medium. Care should be taken to ensure the Ficoll-Paque™ PLUS medium and whole blood:PBS layers do not mix. The centrifuge tube containing layers of Ficoll-Paque™ PLUS medium and whole blood:PBS is centrifuged to separate blood components. Centrifugation can be from about 25 to about 35 minutes at about 400×g. After centrifugation, the blood components are present in separate layers. The top most layer comprises plasma. Directly below the plasma is a buffy coat, which contains white blood cells. Directly below the buffy coat is the Ficoll-Paque™ PLUS medium, and below the Ficoll-Paque™ PLUS medium are the red blood cells. The buffy coat, containing white blood cells, such as mononuclear cells, is collected and placed in a sterile centrifuge tube. Optionally, the white blood cells can be washed one or more times by suspending the cells in PBS, pelleting the cells by centrifugation, and removing the supernatant. After the cells are washed, they can be re-suspended in an appropriate buffer, such as PBS, or in plasma.

In some cases, a density gradient may be used to further separate mononuclear and polymorphonuclear cells. White blood cells may also be prepared from whole blood using filtration; an example includes the Acelere™ MNC Harvest System filtration system (Pall Life Sciences, Ann Arbor, Mich., USA). White blood cells can also be obtained from bone marrow. The white blood cells may be then suspended in a suitable medium, such as plasma, so as to maintain their viability.

Methods for isolating a liquid comprising white blood cell from a tissue include filtration, antibody binding, and electrophoretic methods. Filtrations methods include size exclusion filters, such as hollow fiber arrays, including such filters known in the art. Commercially available filters include LeukoCatch® syringe filters (Watson Co., Ltd., Kobe, Japan), as described by Okuzaki, et al., BMC Clinical Pathology 2011, 11:9, incorporated herein by reference. The LeukoCatch® syringe filters comprise one or more Leukosorb® B Medium filters (Pall Corp, Port Washington, N.Y.) sandwiched between plastic stoppers and set at the bottom of a 10 ml syringe. Leukocytes, but not red blood cells are captured by the filter. Therefore, a LeukoCatch® syringe comprising a plunger can be used to aspirate a sample of whole blood, wherein the leukocytes are captured by the filter. Pushing the plunger down expels the red blood cells from the syringe, but not the leukocytes, which are retained in the filter. The leukocytes can be washed by aspirating phosphate buffered saline (PBS) by pulling the plunger up, and expelling the PBS by pushing the plunger down. Washing can be repeated one or more times. The leukocytes are then eluted by pulling elution buffer into the syringe, and then expelling the elution buffer, now containing leukocytes, into a clean and sterile container. Elution buffer can comprise 10 mM Tris-HCL (pH 7.5), 100 mM NaCl, 1% Triton X-100, 1 mM EDTA (pH 8.0), 0.1 mg/mL PMSF, 1 mM Aprotinin, 0.001 mg/ml leupeptin, 0.001 mg/ml pepstatin A, 1 mM NaF, 1 mM Na3VO4, and 10 mM β-glycerophosphate.

Another non-centrifugal method for generating a liquid volume comprising cytokine-producing cells comprises inducing electrical fields on electrically charged plates to separate cells based on their affinity for different electrical charges. In one such method as described by Wang, et al., Anal Chem. 2000 Feb. 15; 72(4): 832-839 dielectrophoretic field-flow-fractionation (DEP-FFF) can be used to fractionate leukocytes from blood. Leukocytes have different dielectric properties than erythrocytes. Microelectrodes produce DEP forces that levitate blood cells in a thin chamber comprising a top plate and a bottom plate separated by a spacer. When the cells reach an equilibrium height based on their dielectric properties, a carrier fluid moves through the chamber. Cells at different heights travel through the chamber at different velocities, resulting in their separation. For example, whole blood can be diluted 1:1000 in a sucrose buffer. When placed in the thin chamber, a DEP field of about 10 kHz can be applied for DEP-FFF. With a flow rate of about 0.5 ml/min, leukocytes can be enriched 35-fold.

Yet another non-centrifugal method for generating a liquid volume comprising cytokine-producing cells comprises the use of magnetic particles, such as magnetic beads, that specifically bind to cytokine-producing cells. The magnetic particle can be coupled to a molecule that specifically binds to mononuclear leukocytes. The molecule and be a ligand or an antibody. For example, U.S. Pat. No. 7,867,765, by Faustman, et al., issued Jan. 11, 2011 describes magnetic beads conjugated to proteins that bind specifically to white blood cell surface proteins. Antibody or ligand conjugated beads are added to a container containing a sample comprising cytokine-producing cells. The antibody or ligand binds to cytokine-producing cells. After incubating for a preselected period of time, a magnet is placed or held on the outside of the container. While the magnet is placed or held on the outside of the container, the container is tilted to decant contents that are not attracted to the magnet. The content that is attracted to the magnet, white blood cell conjugated magnetic beads, can be washed one or more times with an appropriate buffer, such as PBS. Optionally, the magnetic beads can be separated from the cytokine-producing cells. Finally, the mononuclear cytokine-producing cells can be resuspended in an appropriate buffer, for example PBS or plasma.

In some embodiments, obtaining cytokine cell suspension comprises filtering blood to isolate white blood cells, and suspending the white blood cells in plasma to form a white blood cell suspension. A device for creating such whole blood cell suspension is shown in FIG. 1A. Collecting white blood cells (leukocytes) from a whole blood sample can be performed using filtration methods, as discussed above. For example, as illustrated in FIG. 1A, a filter 220 can be placed at the end of a syringe 200 in which a volume of whole blood is placed. The volume of whole blood can be passed through the filter 220, such as by forcing the blood via a plunger 202 in the syringe 200. Additionally, a centrifuge or gravity system can be used to force the volume of whole blood through the filter 220. White blood cells are collected in the filter 220 while the remaining components of the whole blood, such as red blood cells and plasma, pass through the filter 220. Collecting the separated the white blood cells can then be performed by backwashing the filter 220 with a selected fluid, such as plasma, saline, or other selected fluid. The backwashed material can be backwashed into a collection container, such as the syringe 200, after the whole blood is expressed through the filter in a first direction.

According to various embodiments, therefore, the syringe 200 can have a volume of whole blood positioned therein. The filter 220 can filter and collect white blood cells from whole blood volume, as the whole blood volume is forced (e.g. expressed) through the filter 220. The filter 220 can be positioned at or on the end of the syringe 200. Once the syringe 200 that included the volume of whole blood has expressed the whole blood through the filter 220, the syringe 200 and the filter 220 can be interconnected with a fluid source for backwashing the filter 220. The plunger 202 can then be moved in a second or direction to fill the syringe 200 to pass the backwashing fluid, such as saline or plasma, through the filter 220 to fill the syringe with the backwashed material from the filter, including the white blood cells.

In addition to expressing the whole blood through the syringe and filter into a separate container, and backwashing with a backwashing material from a different source, various components or fractions of the whole blood sample can also be used to backwash the filter. For example, if whole blood is passed through the filter in a first direction, the remaining plasma and/or buffy coat in the whole blood can be used to backwash the filter. Collection of fractionation of the remaining whole blood portions into plasma and/or buffy coat and/or red blood cells can be performed for the various devices such as those disclosed in U.S. Pat. No. 7,845,499; and U.S. Patent Application Publication No. 2011/0192804, published Aug. 11, 2011. For example, with reference to FIG. 1A, a syringe 200 can be filled with an anti-coagulated whole blood sample that is expressed through a filter 220 into a fractionation vessel or tube 230. The fractionation tube 230 can include a buoy system 240 similar to that disclosed in U.S. Patent Application Publication No. 2011/0192804. The buoy system 240 can include a first buoy member 242 that is moveable or fixed relative to a second buoy member 244 with a third buoy member 246. The buoy system 240 can have a connection port or valve or opening 250 that is connectable or permanently connectable with an extraction and/or filling tube with the input port 260. The input port 260 can also be used as an extraction port from the tube 230. Additionally, a separate or plasma extraction port 270 can also be provided into the separation tube 230. An extraction or straw tube 272 can be interconnected with the plasma extraction port 270.

Figure 1C:
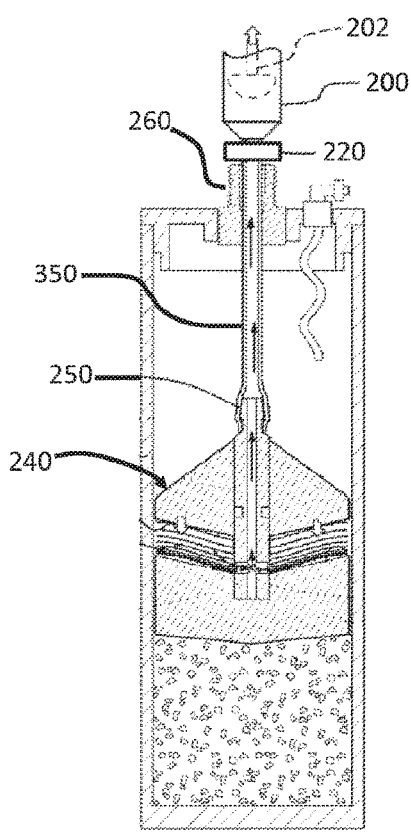
Figure 1D:
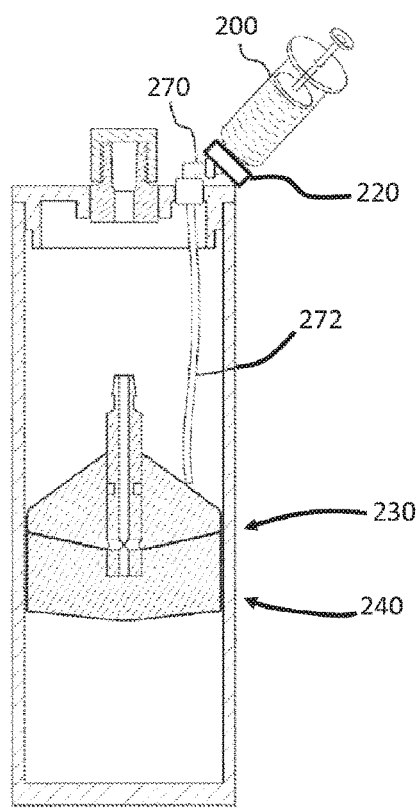

Once the separation tube 230 is filled with the whole blood after it has passed through the white blood filter 220, the tube 230 can be centrifuged to separate the filtered whole blood into selected fractions, such as a red blood cells fraction 300, a buffy coat 310, and a plasma fraction 320. The buoy system 240 can be used to separate the three fractions 300, 310, and 320 for withdrawal from the fractionation tube 230. The fractionated filtered blood, as illustrated in FIG. 1B, can allow for withdrawal of the selected fraction from a single separation tube 230 based upon the selected fraction desired for further processing and/or application. Additionally, as discussed above, the filter 220 can include the white blood cells, or a majority or selected portion of the white blood cells, from the whole blood sample included in the syringe 200. The syringe 200 can then be used to withdraw a selected or multiple fractions from the separation tube 230 by connecting with either the input port 260 or a collection tube 350 connected with the port, valve, or opening 250 of the buoy system 240, as illustrated in FIG. 1C and/or connecting with the plasma extraction port 270 to withdraw material through the plasma extraction tube 272, as illustrated in FIG. 1D.

It is understood that the filter 220 can be positioned between the syringe 200 and the respective ports 260, 270 such that the material withdrawn from the separation tube 230 will backwash the filter 220.

As discussed above, the fractions within the separation tube 230 can be based upon separation of the filtered whole blood sample positioned within the tube 230. According to various embodiments, the factions can include at least a red blood cell fraction 300, a buffy coat fraction as the fraction 310 and the plasma fraction as the fraction 320. Accordingly, according to various embodiments, the buffy coat fraction 310 can be used to backwash the filter 220, as illustrated in FIG. 1B. Alternatively, or in addition to the buffy coat backwash, the plasma fraction 320 can be used to backwash the filter 220, as illustrated in FIG. 1B. It is understood that either or both of the fractions, including the buffy coat fraction 310 and/or the plasma fraction 320 can be used to backwash the filter 220. Accordingly, the separation tube 230 can be used to separate a filtered whole blood sample into selected fractions to backwash the filter 220 for various purposes. It is further understood that additional materials can be used to backwash the filter either initially, intermediately, or following a backwash with the separated whole blood, such as with saline. Accordingly, it is understood that the filter 220 can be backwashed to remove the filtered white blood cells from the filter 220 for use as discussed further herein.

Contacting with a Solid Extraction Material

In some embodiments, fractionating a cytokine cell suspension comprises contacting the liquid with a solid extraction material. Such processes comprise:
  (a) obtaining a cytokine cell suspension;
  (b) contacting the liquid with a solid extraction material; and
  (c) isolating a protein-containing liquid from the solid extraction material.

Accordingly, In various embodiments, the cytokine cell suspension is incubated or otherwise contacted with a solid extraction material to produce a protein-containing liquid. This liquid is then isolated from the solid extraction material, as a Protein Solution of the present technology. Without limiting the scope, mechanism or function of the present technology, solid extraction materials useful herein concentrate cytokines or other proteins in the liquid volume of cytokine-producing cells and may, in some embodiments, activate, stimulate or otherwise increase production of cytokines, including IL-1ra. Thus, in some embodiments, methods comprising activating a cytokine cell suspension with a solid extraction material.

The solid extraction material can include various materials that provide a particular surface area to contact the cells. The solid extraction material may be a continuous material or may be discontinuous and comprise a plurality of separate particles. For example, the solid extraction material may be in the form of a plurality of beads, fibers, powder, a porous material, or a surface of a container comprising the liquid containing the cells. The solid extraction material may comprise geometric forms having various cross-sectional shapes, such as spherical, oval, or polygonal, among others. The solid extraction material can also comprise a continuous porous network, similar to a sponge, or can include a plurality of individual porous particles. The solid extraction material may also provide a larger surface area by being porous in comparison to a non-porous material.

In some embodiments, the solid extraction material includes particles having a large aspect ratio, for example, where the particles are needle-like in shape. The solid extraction material may also be formed as long fibers and may be or take a form similar to glass wool.

In some cases, the solid extraction material can comprise the internal walls of a container holding the cytokine cell suspension. For example, the solid extraction material may comprise the lumen of a syringe that contains the cytokine cell suspension. Other containers include tubes, such as centrifuge tubes, or a blood fractionation device or concentrator assembly as described elsewhere herein.

Where the solid extraction material is a continuous material, such as a porous sponge-like material, the solid extraction material can be used in an amount sufficient to absorb or adsorb or include substantially the entire liquid volume of cytokine-producing cells within the pores or interstices of the solid extraction material. Where the solid extraction material is a discontinuous material, such as a plurality of particles, the solid extraction material can be combined with the liquid containing the cells to form a slurry-like composition. The slurry can vary in consistency from paste-like, having a high-solids fraction, to a readily flowable slurry having a low-solids fraction.

The solid extraction material can provide a large surface area with which to contact the cells. However, in some cases, the solid extraction material can be further treated to increase its surface area, for example, by physically or chemically etching or eroding the surface of the solid extraction material. With respect to chemical etching, a corrosive agent can be used to modify the surface of the solid extraction material depending on the nature of the material. The modified surface may be produced by employing an alkali or an acid, for example chromosulphonic acid, in particular about 20% to about 80% in strength, preferably about 50% chromosulphonic acid. The solid extraction material can be incubated with the corrosive agent for about 5 min to about 30 min in order to chemically etch the surface and increase the surface area. The solid extraction material can then be washed to remove the corrosive agent. For example, the solid extraction material can include the internal walls of a container for holding the cytokine cell suspension where the internal walls are etched to subsequently increase the surface area in contact with the liquid.

Various polymers, metals, ceramics, and glasses can be used as the solid extraction material. In some embodiments, the solid extraction material comprises a hygroscopic material. Examples of suitable solid extraction material materials include glasses, minerals, polymers, metals, and polysaccharides. Minerals include corundum and quartz. Polymers include polystyrene, polyethylene, polyvinyl chloride, polypropylene, and polyacrylamide. Metals include titanium. Polysaccharides include dextran and agarose. A preferred solid extraction material comprises, or consists essentially of, polyacrylamide, as further described below.

The solid extraction material may comprise, for example, continuous solid extraction material of glass or a plurality of glass particles, glass wool, a continuous solid extraction material of metal such as titanium, a plurality of metal beads, metal powder, and combinations thereof. A continuous solid extraction material of metal can include a block or other three-dimensional shape formed of porous metal or metal alloys with an open cell structure. The solid extraction material may include various beads or particles of various sizes including substantially spherical beads. Beads include polystyrene beads, polyacrylamide beads, glass beads, metal (e.g., titanium) beads, or any other appropriate beads. Beads may be any size appropriate for the container and the amount of cytokine cell suspension being used. In some instances, bead sizes can range from about 0.001 millimeters to about 3 millimeters in diameter. Where the bead size is sufficiently small, the beads can appear more like a powder.

Polyacrylamide beads used as the solid extraction material can be formed by polymerizing acrylamide monomer using controlled and standardized protocols as known in the art to produce relatively uniform beads formed of polyacrylamide gel. In general, polyacrylamide is formed by polymerizing acrylamide with a suitable bifunctional crosslinking agent, most commonly N,N'-methylenebisacrylamide (bisacrylamide). Gel polymerization is usually initiated with ammonium persulfate and the reaction rate is accelerated by the addition of a catalyst, such as N,N,N',N'-tetramethylethylenediamine (TEMED). In various embodiments, polyacrylamide beads comprise 0.5 micromole of carboxyl groups per milliliter of beads, imparting a slight anionic character (negative charge). The beads are also typically resistant to changes in pH, and are stable in many aqueous and organic solutions. By adjusting the total acrylamide concentration, the polyacrylamide gel can be formed in a wide range of pore sizes. Moreover, the polyacrylamide beads can be formed in many sizes and can have relatively uniform size distributions. Bead size may range from several micrometers in diameter to several millimeters in diameter. For example, various types of Bio-Gel™ P polyacrylamide gel beads (Bio-Rad Laboratories, Hercules, Calif., USA) have particle sizes ranging from less than about 45 µm up to about 180 µm. Polyacrylamide beads are also available from SNF Floerger (Riceboro, Ga., USA), Pierce Biotechnology, Inc. (Rockford, Ill., USA), and Polymers, Inc. (Fayetteville, Ark., USA).

Once polymerized, polyacrylamide beads can be dried and stored in a powder-like form. The dry beads are insoluble in water but can swell considerably upon being rehydrated. Rehydration returns the polyacrylamide beads to a gel consistency that can be from about two to about three times the dry state size. Thus, dry polyacrylamide beads (i.e., desiccating polyacrylamide beads) may be used to absorb a portion of a liquid volume, including solutes smaller than the bead pore size, and can serve to concentrate IL-1ra and other proteins produced by the cytokine-producing cells. For example, combining dry polyacrylamide beads with the blood and/or platelet-rich plasma in step 230 activates production of IL-1ra by the cytokine-producing cells and also reduces the total liquid volume as the dry beads rehydrate and swell.

Without limiting the scope, mechanism or function of the present technology, it has been discovered that surface contact with the solid extraction material can activate the cells and the solid extraction material can, in some cases, assist in the separation and concentration of the resulting Protein Solution rich in cytokines, including IL-1ra. For example, in the case of a porous solid extraction material, a portion of the liquid comprising the cells can enter the pores and remain therein. Cells in the liquid may contact this additional surface area. In some embodiments, the pores are too small for the cells to enter, but a portion of the liquid can enter the pores. Liquid can be removed from the solid extraction material and pores by centrifuging, for example.

The solid extraction material is preferably sterilized, using techniques among known in the art, in order to prevent contamination of the cytokine cell suspension. For example, heat and pressure sterilization methods, such as autoclaving, may be used depending on the particular composition of the solid extraction material. Alternative methods, such as chemical sterilization or irradiation, can be used where the solid extraction material may be adversely affected by the autoclaving process.

In some embodiments, the cytokine cell suspension is incubated with solid extraction material for a time effective to remove a portion of the liquid. The incubation may be carried out over a period from about 30 seconds to about 72 hours and may be carried out at a temperature from about 20° C. to about 41° C. For example, the incubation may be from about one minute to about 48 hours, from about 2 minutes to about 24 hours, from about 5 minutes to about 12 hours, from about 10 minutes to about 6 hours, from about 15 minutes to about 5 hours, from about 30 minutes to about 4 hours, from about 1 hour to about 3 hours, or from about 2 hours to about 2.5 hours. In some embodiments, the incubation is conducted at about 37° C. In some embodiments the liquid is not incubated, but is contacted with the solid extraction material for only so long as necessary to perform subsequent processing. The contacting may occur at ambient conditions, e.g., at a temperature of about 20-25° C.

In some embodiments, the cytokine cell suspension and the solid extraction material are agitated to more thoroughly mix these components during contact. The agitation may be accomplished by inverting, shaking, rocking, stirring, or vortexing the liquid and solid extraction material. Agitation may increase contact of the cells within the liquid with the solid extraction material. Agitation may be performed once, repeated multiple times, repeated periodically, or may be continuous. The liquid comprising the cells and the solid extraction material may also be agitated while the liquid is stimulated with an electromagnetic field, as described below. Additional aspects and features relating to producing protein-rich solutions using polyacrylamide beads and other solid extraction materials are described in: U.S. Patent Application Publication No. 2009/0220482, Higgins et al., published Sep. 3, 2009; U.S. Patent Application Publication No. 2010/0055087, Higgins et al., published Mar. 4, 2010; U.S. Patent Application Publication 2011/0052561, Hoeppner, published Mar. 3, 2011; International Application Publication 2012/030593, Higgins et al., published Mar. 8, 2012; and U.S. Patent Application Publication 2012/0172836, Higgins et al., published Jul. 5, 2012.

Contacting of the liquid containing cytokine-producing cells with the solid extraction material may be performed using a suitable container or other apparatus to effect the contact. Contacting may be performed in a continuous process wherein a flow of the liquid is passed over or through the solid extraction material, or the liquid and solid extraction material may be contained in a vessel. As discussed above, the vessel may comprise the solid extraction material, or may merely serve as a container holding the beads or other forms of the material. Containers useful in the present technology include those known in the art, such as the Plasmax™ Plus Plasma Concentrator, commercially available from Biomet Biologics, LLC (Warsaw, Ind., USA) and may include those devices and methods of use as described in U.S. Pat. No. 7,553,413, Dorian et al., issued Jun. 30, 2009; and U.S. Pat. No. 7,694,828, Swift et al., issued Apr. 13, 2010.

Such a device is shown in FIGS. 2A and 2B, for exemplary use with a polyacrylamide gel bead solid extraction material. The device 400 has an upper chamber 405 and a lower chamber 410. The upper chamber 405 has an end wall 415 through which the agitator stem 420 of a gel bead agitator 425 extends. The device 400 also has an inlet port 430 that extends through the end wall 415 and into the upper chamber 405. The device 400 also includes an outlet port 435 that communicates with a plasma concentrate conduit 440. The floor of upper chamber 405 includes a filter 445, the upper surface of which supports desiccated concentrating polyacrylamide beads 450.

During use, a fluid 455 containing cytokine-producing cells and, optionally, platelets is injected to the upper chamber 405 via the inlet port 430 and mixed with the polyacrylamide beads 450. The fluid 455 and polyacrylamide beads 450 may be mixed by rotating the agitator stem 420 and the gel bead agitator 425, to help mix the fluid 455 and beads 450. The mixed fluid 455 and polyacrylamide beads 450 are then incubated for the desired time at the desired temperature. The device 400 is then centrifuged so that liquid passes to the lower chamber 410 while the polyacrylamide beads 450 are retained by a filter 445, thereby separating the polyacrylamide beads 150 from the resulting solution 460 of IL-1ra and other proteins that collects in the lower chamber 410. The solution 460 may be removed from the device via outlet port 435.

The cytokine cell suspension can be stimulated with an electromagnetic field, before or during the contacting of the liquid with a solid extraction material. Thus, in some embodiments, stimulation of the liquid comprising the cells can be performed prior to contacting the liquid and the solid extraction material. However, it is preferred that at least a portion of the contacting step and at least a portion of the stimulating step overlap in time such that the liquid comprising the cells is concurrently in contact with the solid extraction material and stimulated with the electromagnetic field.

Stimulating the cytokine cell suspension with an electromagnetic field may involve various forms of electromagnetic stimulation, such as a pulsed electromagnetic field or a capacitively coupled electromagnetic field. In some embodiments, the liquid is stimulated using a power source coupled to a stimulation coil. The current passing through the coil produces a pulsing magnetic field which induces in the liquid a pulsing electric field. The coil may partially surround the liquid as it is held within a container, such as a tube or syringe. The coil may be integrated into to the container holding the cytokine cell suspension or may be removable. For example, a plastic tube can be formed with an integrated coil or the coil can be temporarily coupled to the container or placed within the container; for example, the tube can be configured so that the coil can be snapped onto the container. The power source can be coupled to the coil as needed to perform the stimulating step.

Stimulation of the liquid with an electromagnetic field may also include placing at least two electrodes across the liquid. Electrical energy may then be applied to the electrodes so as to capacitively couple the electrodes and generate the electromagnetic field there between. The electromagnetic field is therefore able to pass through the liquid so as to increase the rate and/or amount of cytokine production. In other embodiments, electrodes can be used to produce a direct current or one or more coils can be used to produce a pulsed electromagnetic field.

The strength of the electromagnetic field during stimulation can be at least about 0.5 microvolts per centimeter, whether produced by direct current, capacitively coupled current, or pulsed electromagnetic field. In the case of a direct current electrode, the amplitude of the current can be from about 1 to about 200 microamperes, and in some embodiments, the amplitude may be from about 20 to about 100 microamperes. In still further embodiments, the current may be about 20, about 60, or about 100 microamperes. It should be understood, however, that the amplitude of the current may be of other suitable magnitudes.

The electromagnetic field applied during the stimulating step may be constant or vary over time. For example, a sinusoidal time varying electromagnetic field can be applied using the electrodes placed across the liquid. Such a sinusoidal time varying electromagnetic field can have a peak voltage across the electrodes from about 1 volt to about 10 volts, and in some embodiments, the peak voltage can be about 5 volts. The corresponding electric field produced can have an amplitude of from about 0.1 millivolt per centimeter (mV/cm) to about 100 mV/cm, and in some embodiments can be about 20 mV/cm. The sinusoidal time varying electric field may have a frequency of from about 1,000 Hz to about 200,000 Hz, and in some embodiments the frequency may be about 60,000 Hz.

The electromagnetic field applied to the liquid may also be a pulsed electromagnetic field. The pulsed electromagnetic field can be induced using an external coil and a pulse generator. In this regard, a pulsed electromagnetic field may have a pulse duration of from about 10 microseconds per pulse to about 2000 microseconds per pulse. The pulse duration in one embodiment can be about 225 microseconds. The pulses may include electromagnetic bursts, in which a burst can comprise from 1 pulse to about 200 pulses. Alternatively, the electromagnetic field may have bursts that comprise from about 10 pulses to about 30 pulses. In this regard, in one embodiment each burst may comprise about 20 pulses.

The frequency at which bursts in the pulsed electromagnetic are applied may vary. In this regard, bursts can be repeated at a frequency of from about 1 Hz to about 100 Hz in some embodiments, and can be repeated at a frequency of about 10 Hz to about 20 Hz in other embodiments. Furthermore, bursts can repeat at a frequency of about 1.5 Hz, about 15 Hz or about 76 Hz. A burst can have a duration from about 10 microseconds up to about 40,000 microseconds. In this regard, a burst can have a duration of about 4.5 milliseconds.

Suitable devices for generating a capacitively coupled electromagnetic field include SpinalPak® spinal stimulator (EBI, L.P., Parsippany, N.J.) or a DC stimulation device such as an SpF4 XL IIb spinal fusion stimulator (EBI, L.P., Parsippany, N.J.). Pulsed electromagnetic fields can be produced using various known methods and apparatuses, such as using a single coil or a pair of Helmholtz coils. For example, a suitable apparatus includes the EBI Bone Healing System Model 2001 healing device (EBI, L.P., Parsippany, N.J.) and the Biomet Trauma and Biomet Spine (BTBS) (Biomet, Warsaw, Ind.) stimulation coil. With respect to direct current, an electric field may be generated using any known device for generating a direct current electric field, such as for example, the Osteogen™ implantable bone growth stimulator (EBI, L.P., Parsippany, N.J.). Other suitable devices for generating electromagnetic fields may be used.

Electromagnetic stimulation of the cytokine cell suspension can be continued and/or repeated as desired with respect to contacting the liquid and the solid extraction material. It should be understood, however, that the step of stimulating the liquid with an electromagnetic field includes fields other than, or in addition to, electric or electromagnetic fields associated with ambient conditions (such the electromagnetic fields generated by casual exposure to radios, telephones, desktop computers or similar devices).

In some embodiments, both the contacting and stimulating steps as shown in FIG. 1 are performed in less than about 1 hour. The contacting and stimulating steps can also be performed at temperatures ranging from about 20° C. to about 37° C. In a preferred embodiment, the temperature of the cytokine cell suspension is kept at about 37° C. during the contacting and stimulating steps. One or both of the contacting and stimulating steps are typically performed ex vivo.

Therapeutic Compositions

The present technology also provides compositions comprising a Protein Solution and a second component comprising active materials, physiological carriers, and combinations thereof. In some embodiments, compositions comprise a safe and effective amount of the Protein Solution and a safe and effective amount of a second active. A "safe and effective" amount of a component is an amount that is sufficient to have the desired therapeutic effect in the human or other mammalian subject, without undue adverse side effects (such as toxicity, irritation, or allergic response), commensurate with a reasonable benefit/risk ratio when used in the manner of this technology. The specific safe and effective amount of the component will, obviously, vary with such factors as the particular condition being treated, the physical condition of the patient, the nature of concurrent therapy (if any), the specific components used, the specific route of administration and dosage form, the carrier (if any) employed, and the desired dosage regimen.

Active materials among those useful herein include biologics and pharmaceutical actives. Biologics include blood fractions, such as PRP, blood products, and concentrated bone marrow aspirate (cBMA).

Accordingly, in some embodiments, the present technology provides compositions comprising a safe and effective amount of a Protein Solution and a safe and effective amount of cBMA. An autologous therapeutic composition comprises APS and cBMA in an APS:cBMA ratio of about 1:1, about 1:2, about 1:3, about 1:4, about 1:5, about 1:6, about 1:7, about 1:8, about 1:9 or about 1:10. Alternatively, the APS:cBMA ratio can be about 2:1, about 3:1, about 4:1, about 5:1, about 6:1, about 7:1, about 8:1, about 9:1 or about 10:1. cBMA can include hematopoietic, stem cells, stromal stem cells, mesenchymal stem cells, endothelial progenitor cells, red blood cells, cytokine-producing cells, fibroblasts, reticulocytes, adipose cells, or endothelial cells.

In some embodiments, the cBMA and Protein Solution may be produced simultaneously. Thus, in reference to FIG. 1 and the processes described above, bone marrow aspirate may be added to the whole blood, prior to or during the contacting with a solid extraction material; such a process involves operation of both steps 115 and 130. For example, bone marrow aspirate may be added to whole blood prior or during isolation of platelet-rich plasma in step 120. Such methods include those described in U.S. Application Publication No. 2006/0278588, Woodell-May, published Dec. 14, 2006.

Pharmaceutical actives among those useful herein include herein include organic molecules, proteins, peptides, peptidomimetics, nucleic acids, nucleoproteins, antisense molecules, polysaccharides, glycoproteins, lipoproteins, carbohydrates and polysaccharides, botanical extracts, and synthetic and biologically engineered analogs thereof, living cells (other than cytokine-producing cells stromal cells) such as chondrocytes, bone marrow cells, viruses and virus particles, natural extracts, and combinations thereof. Specific non-limiting examples of bioactive materials include hormones, antibiotics and other anti-infective agents, hematopoietics, thrombopoietics, antiviral agents, antitumor agents (chemotherapeutic agents), antipyretics, analgesics, anti-inflammatory agents, antiallergy agents, vasodilators, cytokines, growth factors, gene regulators, vitamins, minerals and other nutritionals, nutraceuticals and combinations thereof. In particular, actives include bronchodilators (such as albuterol, levabuterol, irbuterol, ipatropium, salmeterol, and formoterol), glucocorticosteroids (such as mometasone, fluticasone, budesonide, and beclomethosone), antibiotics, antivirals, and combinations thereof. In some embodiments, compositions may comprise growth factors in addition to those present in the Protein Solution, such Platelet-Derived Growth Factor (PDGF), Transforming Growth Factor Beta (TGF-β), Insulin-Like Growth Factor (IGF), Fibroblast Growth Factor (FGF), Epidermal Growth Factor (EGF), Vascular Endothelial Growth Factor (VEGF), and Bone Morphogenetic Proteins (BMPs).

In some embodiments, Protein Solutions comprise one or more cytokines from synthetic or recombinant sources. In particular, by way of example, a Protein Solution may comprise interleukin-1 receptor antagonist (IL-1ra) that is synthetic or recombinant, or isolated from autologous, allogeneic or xenogeneic blood or other biologic sources, aside from the methods described above. For example, Kineret™ (anakinra) is a recombinant, non-glycosylated form of IL-1ra, sold by Amgen Manufacturing, Ltd. (Thousand Oaks, Calif.). Various recombinant interleukin-1 inhibitors and methods of treatment are described in U.S. Pat. No. 6,599,873, Sommer et al., issued Jul. 29, 2003; U.S. Pat. No. 5,075,222, Hannum et al., issued Dec. 24, 1991; and U.S. Application Publication No. 2005/0197293, Mellis et al., published Sep. 8, 2005. In addition, methods for producing IL-1ra from body fluids, including the use of autologous fluids, are described in U.S. Pat. No. 6,623,472, Reinecke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004. When an allogeneic anti-inflammatory cytokine composition is to be generated, multiple sources of IL-1ra from multiple subjects may be pooled together.

In some embodiments, Protein Solutions comprise one or more cytokines derived from a tissue comprising cytokine-producing cells, by contacting a cytokine cell suspension with a solid extraction material, wherein the liquid is isolated from a tissue using centrifugation or other gravimetric methods. Liquids comprising cytokine-producing cells include blood, adipose tissue, bone marrow, and fractions thereof, such as platelet-rich plasma. Solid extraction materials include those described above. Devices for making blood fractions by centrifugation of whole blood are described in U.S. Pat. No. 7,992,725, Leach et al., issued Aug. 9, 2011, U.S. Pat. No. 7,374,678, Leach, issued May 20, 2008; U.S. Pat. No. 7,179,391 to Leach et al., issued Feb. 20, 2007; U.S. Pat. No. 7,992,725, Leach et al., issued Aug. 9, 2011; U.S. Pat. No. 7,806,276, Leach et al., issued Oct. 5, 2010; and U.S. Pat. No. 8,048,297, Leach et al., issued Nov. 1, 2011. Methods for making solutions rich in cytokines are described in U.S. Patent Application Publication No. 2009/0220482, Higgins et al., published Sep. 3, 2009; U.S. Patent Application Publication No. 2010/0055087, Higgins et al., published Mar. 4, 2010; U.S. Patent Application Publication 2011/0052561, Hoeppner, published Mar. 3, 2011; International Application Publication 2012/030593, Higgins et al., published Mar. 8, 2012; and U.S. Patent Application Publication 2012/0172836, Higgins et al., published Jul. 5, 2012.

Other methods for producing components of Protein Solutions useful herein are described in the following co-filed applications, the disclosures of which are incorporated by reference herein: Compositions and methods useful in aspects of the present technology are also described in the following applications filed concurrently with this disclosure: U.S. patent application Ser. No. 13/840,562, Binder et al., Methods and Non-Immunugenic Compositions for Treating Inflammatory Diseases; U.S. patent application Ser. No. 13/841,083, Landrigan, et al., Treatment of Inflammatory Respiratory Disease Using Protein Solutions; U.S. patent application Ser. No. 13/837,005, Woodell-May et al., Methods and Acellular Compositions for Treating Inflammatory Disorders; U.S. patent application Ser. No. 13/837,480, Treatment of Pain Using Protein Solutions; U.S. patent application Ser. No. 13/840,129, Matusuka, et al., Treatment of Collagen Defects Using Protein Solutions; and U.S. patent application Ser. No. 13/841,103, Landrigan, et al., Treatment of Peripheral Vascular Disease Using Protein Solutions, all of which are incorporated by reference herein.

The compositions may comprise a carrier material, in addition to any liquid comprising the Protein Solution. It should be understood that in various embodiments of the present technology, methods of treatment employ the Protein Solution as comprised and made above, without further carrier, by direct injection or other application to the site of treatment. However, in other embodiments, an additional carrier material may be used for such reasons as for ease of administration, to facilitate administration using a particular delivery device, enhancing activity, an increasing the length of time the Protein Solution remains at the site of administration. Carriers among those useful herein include saline, hyaluronic acid, collagen, buffers (such as Hank's Buffer), cell culture media, blood products (such as PRP and platelet poor plasma), and mixtures thereof.

Protein Solutions, and compositions comprising Protein Solutions may be sterilized prior to administration, by any suitable method. For example, a Protein Solution may be sterilized by including a sterile filter to process the product made by the processes described above. In some embodiments, an antibiotic may be included in the solid extraction material during the contacting step described above, or may be added at one or more of the various steps in the methods and treatments described herein. Alternatively, or in addition, the Protein Solution may be produced aseptically.

Protein Solutions and compositions comprising Protein Solutions may also be lyophilized (freeze drying, or cryo-desiccation) after production, using methods among those known in the art. Thus, the Protein Solution can be lyophilized after it is isolated from the solid extraction material. When freeze dried, the anti-inflammatory cytokine composition can be hydrated with a suitable media 170, at a time before administration or at a time of administration.

Hydration may be accomplished by mixing the composition with a solution including saline, buffers, blood, blood fractions, bone marrow aspirate, concentrated bone marrow aspirate, and combinations thereof.

In some embodiments, a crypreservative storage solution is be added to the Protein Solution, to provide stability for subsequent storage at reduced temperatures. Suitable storage solutions include those in the art, such as glycerol and dimethylsulfoxide (DMSO). The composition may be stored at reduced temperatures, such as from about 1° C. to about 6° C. In some embodiments, the composition is stored under liquid nitrogen, at about −80° C. Preferably, the cryopreservative storage solution is removed from the Protein Solution prior to administration to a mammalian subject. Removal of the storage solution may be performed by methods including those known in the art for processing stored blood comprising cryopreservatives. Washing may be performed using a wash solution, such as saline. In such embodiments, the blood type of the subject to be treated may be matched to the blood type of the donor from whom the cytokine cell suspension was obtained.

Methods of Treatment

The present technology provides methods for the treatment of an inflammatory disorder or other disorder mediated by IL1-ra in a human or other mammalian subject, comprising administration of a Protein Solution of the present technology to the subject. Methods include treating an inflammatory disorder using a Protein Solution that is made by contacting a cytokine cell suspension with a solid extraction material, wherein the liquid is whole blood, bone marrow aspirate, adipose tissue, or fractions thereof.

Such diseases may be characterized by elevated neutrophil counts. Without limiting the mechanism, utility or function of the present technology, the methods and treatments of this technology mediate the effects of interleukin-1 and its role in the inflammation cascade. As generally discussed above, interleukin-1 (IL-1) includes a family of cytokines that can stimulate lymphocytes, neutrophils, and macrophages, activate phagocytes, increase airway fibrosis, promote lymphocyte nodules in the airways, increase production of both MMP-9 and MMP-12, and are involved in many chronic inflammatory conditions. IL-1 can be generated by macrophages, monocytes, and dendritic cells, and can be part of the inflammatory response against infection. See, Lappalainen et al., "Interleukin-1β Causes Pulmonary Inflammation, Emphysema, and Airway Remodeling in the Adult Murine Lung" American Journal of Respiratory Cell and Molecular Biology, vol. 32, no. 4, pages 311-318 (April 2005).

The mode of action of IL-1 can be mediated by IL-1ra. IL-1ra binds to the same receptor on the cell surface as IL-1, and thus prevents IL-1 from sending a signal to that cell. IL-1ra is secreted from cytokine-producing cells, including monocytes, macrophages, neutrophils, polymorphonuclear cells (PMNs), and other cells, and can modulate a variety of IL-1 related immune and inflammatory responses, as described by Arend W P, Malyak M, Guthridge C J, Gabay C (1998) "Interleukin-1 receptor antagonist: role in biology" Annu. Rev. Immunol. 16: 27-55. Production of IL-1ra is stimulated by several substances including adherent immunoglobulin G (IgG), other cytokines, and bacterial or viral components. Likewise, the mode of action of TNF-α can be mediated by sTNF-RI and sTNF-RII, which prevent TNF-α from binding to membrane bound TNF-RI and/or TNF-RII.

Examples of inflammatory disorders treated by the methods of this technology include rheumatoid arthritis, osteoarthritis, osteolytis, tendonitis, synovitis, peripheral vascular disease, and inflammatory respiratory diseases (such as chronic obstructive pulmonary disease, fibrosis, emphysema, acute respiratory distress syndrome, and pneumonia). Treatment methods also include the prevention, reduction or elimination of pain associated with various disorders, such as pain associated with traumatic injury, muscle strain, arthritis (rheumatoid arthritis and osteoarthritis), synovitis, sacroiliac joint disorders, back disorders, post-surgical injections, tendon injections, sports medicine procedure (for example, ACL repair, MCL repair, BTB repair, patella repair, or cartilage repair), contusions, muscle strains, post traumatic osteoarthritis. Methods also include stimulation of chondrocyte production at the site of a collagen defect, such as defects at joints associated with arthritis, injuries or surgical procedures.

In some embodiments, methods of the present technology comprise administration of a Protein Solution to the site of a tissue defect to prevent or treat a disorder associated with IL-1ra. As referred to herein, such "tissue defects" include any condition involving tissue which is inadequate for physiological or cosmetic purposes. Examples of such defects include those that are congenital, those that result from or are symptomatic of disease, disorder, or trauma, and those that are consequent to surgical or other medical procedures. Embodiments include treatment for vascular, bone, skin, nerve, and organ tissue defects. Examples of such defects include those resulting from osteoporosis, spinal fixation procedures, hip and other joint replacement procedures, chronic wounds, fractures, sclerosis of tissues and muscles, and spinal cord or other nerve injury. In various embodiments, the compositions and methods of this invention may be used in methods associated with the repair bone or cartilage defects.

In various embodiments, methods are for the treatment of inflammatory disorders in a human. In other embodiments, treatment is for non-human mammals, such as companion, working, and sports animals. For example, such methods of this technology may be used for the treatment of inflammatory disorders in horses.

The present technology also provides point-of-care methods for making a Protein Solution. As referred to herein, a "point-of-care method" wherein the processes of the present technology are performed at a time proximate to the administration of the Protein Solution to the subject being treated. Such methods may be performed at a location proximate, such as in the same room (for example, bed side) or otherwise immediately adjacent, to the mammalian subject to be transfused with the RBCs. In various embodiments, a "proximate time" may be, for example, within 12 hours, within 8 hours, within 2 hours, within 1 hour or within 30 minutes of administration of the Protein Solution to the subject.

In some embodiments, the Protein Solution is administered with a concomitant therapy. Such therapies include, for example, the administration of pharmaceutical actives or biologics, as described above. In some embodiments, concomitant therapies are administered concurrently with a Protein Solution. For example, methods may comprise administration of a Protein Solution with a safe and effective amount of an active selected from the group consisting of glucocorticosteroids, non-steroidal anti-inflammatories, antibiotics, antivirals, and combinations thereof.

In some embodiments, methods comprise administration of a Protein Solution with concentrated bone marrow aspirate, as described above. For example, cBMA and a Protein Solution may be administered concomitantly. Accordingly, in some embodiments, the present technology provides compositions comprising a safe and effective amount of a Protein Solution and a safe and effective amount of cBMA. An autologous therapeutic composition comprises APS and cBMA in an APS:cBMA ratio of about 1:1, about 1:2, about 1:3, about 1:4, about 1:5, about 1:6, about 1:7, about 1:8, about 1:9 or about 1:10. Alternatively, the APS:cBMA ratio can be about 2:1, about 3:1, about 4:1, about 5:1, about 6:1, about 7:1, about 8:1, about 9:1 or about 10:1. cBMA can include hematopoietic, stem cells, stromal stem cells, mesenchymal stem cells, endothelial progenitor cells, red blood cells, white blood cells, fibroblasts, reticulocytes, adipose cells, or endothelial cells. Methods for producing cBMA among those useful herein are described in U.S. Application Publication No. 2006/0278588, Woodell-May, published Dec. 14, 2006.

Methods of the present technology generally comprise administration of a Protein Solution to the site of inflammation in a mammalian subject. Administration of the Protein Solution can be performed with any suitable device, including such devices known in the art for topical delivery of compositions to the muscle, joint, vascular, lung or other tissue. For example, topical delivery for treatment of inflammation or pain associated with joint disorders may comprise injection of a Protein Solution at or near the joint. Treatment for inflammatory respiratory diseases may comprise delivery of a Protein Solution by endotracheal tubes, inhalers and nebulizers.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The disclosure of all references, including published and pending patents and patent applications, cited in this disclosure are incorporated by reference herein.

The description and specific examples, while indicating embodiments of the technology, are intended for purposes of illustration only and are not intended to limit the scope of the technology. Equivalent changes, modifications and variations of specific embodiments, materials, compositions and methods may be made within the scope of the present technology, with substantially similar results. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "prefer" or "preferable" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein. Further, as used herein the term "consisting essentially of" recited materials or components envisions embodiments "consisting of" the recited materials or components.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

What is claimed is:

1. A method for generating a solution rich in interleukin-1 receptor antagonist (IL-1ra) comprising:
   obtaining a liquid volume comprising white blood cells by separating white blood cells from a tissue comprising any one of: (a) whole blood, bone marrow aspirate, adipose tissue; (b) a fraction thereof; or (c) a mixture of any of the foregoing, using dielectrophoretic field-flow-fractionation (DEP-FFF), wherein separating the white blood cells concentrates the white blood cells to at least about 15,000/µl; and
   contacting the liquid volume comprising white blood cells with a solid extraction material to obtain a solution rich in IL-1ra.

2. The method according to claim 1, wherein the solution rich in IL-1ra further comprises one or more proteins selected from the group consisting of epidermal growth factor (EGF), hepatocyte growth factor (HGF), platelet-derived growth factor BB (PDGF-BB), and soluble interleukin one receptor II (sIL-1RII).

3. The method according to claim 1, wherein the solution rich in IL-1ra comprises:
   (i) interleukin-1 receptor antagonist (IL-1ra) at a concentration of at least about 10,000 pg/ml;
   (ii) soluble Tumor Necrosis Factor Receptor 1 (sTNF-R1) at a concentration of at least about 1,200 pg/ml; and
   (iii) EGF, HGF, PDGF-BB, or soluble interleukin one receptor II (sIL-1RII) at a concentration of at least about 2,000 pg/ml.

4. The method according to claim 1, wherein the solid extraction material comprises any one of corundum, quartz, titanium, dextran, agarose, polyacrylamide, polystyrene, polyethylene, polyvinyl chloride, polypropylene, or a combination of any of the foregoing.

5. The method according to claim 4, wherein the solid extraction material comprises polyacrylamide.

6. The method according to claim 1, wherein the solid extraction material comprises a form selected from the group consisting of a bead, fiber, powder, porous material, and combinations thereof.

7. The method according to claim 1, wherein the surface of the solid extraction material is etched to increase its surface area.

8. The method according to claim 1, wherein the contacting is for a period of time from about 30 seconds to about 2 hours.

9. The method according to claim 1, wherein the contacting comprises subjecting the liquid to an electromagnetic field.

10. The method according to claim 9, wherein the electromagnetic field comprises a pulsed electromagnetic field or a capacitively coupled electromagnetic field.

11. A method of preparing an enriched biological solution, comprising:
    (a) separating white blood cells from a tissue selected from whole blood, bone marrow aspirate, adipose tissue, a fraction thereof, or a mixture thereof to produce a volume of concentrated white blood cells, including subjecting the tissue to di electrophoretic field-flow-fractionation (DEP-FFF), wherein the separating separates at least about one-half of red blood cells in the tissue from the volume of white blood cells;
    (b) mixing the volume of white blood cells with a liquid medium to form a cytokine cell suspension, wherein the cytokine cell suspension comprises white blood cells, and at least one of platelets, adipose stromal cells, and mesenchymal stromal cells;
    (c) contacting the cytokine cell suspension with polyacrylamide beads for a period of time between about 30 seconds and about 72 hours; and
    (d) separating liquid from the polyacrylamide beads to obtain a solution rich in IL-1ra and rich in at least one of epidermal growth factor (EGF), hepatocyte growth factor (HGF), platelet-derived growth factor-BB (PDGF-BB), and soluble interleukin-1 receptor II (sIL-1RII).

12. The method according to claim 11, wherein the tissue is autologous with the subject.

13. The method according to claim 11, wherein the solution rich in IL-1ra has an IL-1ra concentration of at least about 10,000 pg/ml.

14. The method according to claim 11, wherein the solution rich in IL-1ra further comprises at least one protein selected from soluble tumor necrosis factor receptor II (sTNF-RII), insulin-like growth factor-I (IGF-I), platelet-derived growth factor-AB (PDGF-AB), vascular endothelial growth factor (VEGF), and transforming growth factor-β1 (TGF-β1), wherein the concentration of the selected protein in the solution is greater than the concentration of the selected protein in normal blood.

15. The method according to claim 11, wherein separating comprises:
    (a) diluting the tissue comprising white blood cells in a sucrose buffer to form a biological sample;
    (b) loading the biological sample into a chamber comprising a top plate and a bottom plate, wherein the top plate and bottom plate are coupled to microelectrodes;
    (c) applying a dielectrophoretic (DEP) field to the biological sample, wherein white blood cells are suspended in the biological sample; and
    (d) isolating a volume of white blood cells by flowing a carrier fluid through the chamber.

16. The method according to claim 15, wherein the DEP field comprises a frequency of about 10 kHz.

17. The method according to claim 11, wherein the white blood cells are concentrated to at least about 15,000/µl.

18. The method according to claim 11, further comprising:
    (e) administering the solution rich in IL-1ra to a mammalian subject.

19. A method for generating a biological solution enriched in anti-inflammatory cytokines and growth factors, the method comprising:
    subjecting a tissue comprising any one of: (a) whole blood, bone marrow aspirate, adipose tissue; (b) a fraction thereof; or (c) a combination of any of the foregoing, to dielectrophoretic field-flow-fractionation to separate white blood cells from the tissue to produce a volume of white blood cells at a concentration of at least about 15,000/µl, wherein the volume of white blood cells includes about one-half or less of red blood cells from the tissue; and contacting the volume of white blood cells with a solid extraction material to obtain the biological solution enriched in at least one protein selected from interleukin-1 receptor II, platelet-derived growth factor BB, epidermal growth factor, and hepatocyte growth factor.

20. The method of claim 19, wherein the at least protein is at a concentration of at least 2,000 pg/ml.

21. The method of claim 19, wherein the at least one protein is present in a concentration greater than the concentration of the at least one protein in normal blood.

22. The method of claim 19, wherein the at least one protein is a growth factor at a concentration of at least about 1,500 pg/ml.

23. The method of claim 19, wherein the solution further comprises at least one supplemental protein selected from soluble tumor necrosis factor receptor II (sTNF-RII), insulin-like growth factor-I (IGF-I), platelet-derived growth factor-AB (PDGF-AB), vascular endothelial growth factor (VEGF), and transforming growth factor-$\beta$1 (TGF-$\beta$1), wherein the concentration of the selected supplemental protein in the solution is greater than the concentration of the selected supplemental protein in normal blood.

24. The method of claim 19, wherein the contacting comprises subjecting the white blood cells to an electromagnetic field.

25. The method of claim 19, wherein the contacting is for a period of less than 30 minutes.

26. The method according to claim 19, wherein the solid extraction material comprises any one of corundum, quartz, titanium, dextran, agarose, polyacrylamide, polystyrene, polyethylene, polyvinyl chloride, polypropylene, or a combination of any of the foregoing.

* * * * *

UNITED STATES PATENT AND TRADEMARK OFFICE
CERTIFICATE OF CORRECTION

PATENT NO. : 10,208,095 B2  
APPLICATION NO. : 13/839280  
DATED : February 19, 2019  
INVENTOR(S) : Leach et al.

It is certified that error appears in the above-identified patent and that said Letters Patent is hereby corrected as shown below:

On the Title Page

In item (71), in "Applicant", in Column 1, Line 1, delete "Biologics," and insert --Manufacturing,-- therefor In Column 2, under "U.S. Patent Documents", Line 12, delete "3,469,369 A 7/1969 Flodin et al." and insert --3,453,364 A 7/1969 Flodin et al.
3,469,369 A 9/1969 Helmke-- therefor On page 7, in Column 1, under "Other Publications", Line 9, delete "toher acive" and insert --other active-- therefor On page 7, in Column 2, under "Other Publications", Line 57, delete ""Therapuetic" and insert --"Therapeutic-- therefor On page 7, in Column 2, under "Other Publications", Line 61, delete ""Intratrachael" and insert --"Intratracheal-- therefor On page 8, in Column 1, under "Other Publications", Line 43, delete "Nov. 5," and insert --Nov. 15,-- therefor On page 9, in Column 1, under "Other Publications", Line 67, delete "13/841,083," and insert --13/841,103,-- therefor On page 9, in Column 2, under "Other Publications", Line 23, delete "Jan. 15," and insert --Jan. 25,-- therefor On page 9, in Column 2, under "Other Publications", Line 29, delete "14/808,828,Preliminary" and insert --14/808,828, Preliminary-- therefor Signed and Sealed this
Twenty-eighth Day of April, 2020

Andrei Iancu
*Director of the United States Patent and Trademark Office*

CERTIFICATE OF CORRECTION (continued)
U.S. Pat. No. 10,208,095 B2

On page 9, in Column 2, under "Other Publications", Line 44, delete "Jun. 20," and insert --Jun. 10,-- therefor On page 12, in Column 1, under "Other Publications", Line 44, delete "Protofibral" and insert --Protofibril-- therefor On page 12, in Column 2, under "Other Publications", Line 27, delete "ensor" and insert --tensor-- therefor On page 12, in Column 2, under "Other Publications", Line 38, delete "homrone" and insert --hormone-- therefor On page 12, in Column 2, under "Other Publications", Line 61, delete "lntra-Operative" and insert --Intra-Operative-- therefor On page 13, in Column 1, under "Other Publications", Line 56, delete "preclincial" and insert --preclinical-- therefor On page 13, in Column 2, under "Other Publications", Line 20, delete "(IL)-1a, IL-1b" and insert --(IL)-1α, IL-1β-- therefor On page 13, in Column 2, under "Other Publications", Line 23, delete "(TNF)-a," and insert --(TNF)-α,-- therefor On page 13, in Column 2, under "Other Publications", Line 23, delete "(TGF)-B2," and insert --(TGF)-$β_2$,-- therefor On page 13, in Column 2, under "Other Publications", Line 24, delete "(TGF)-(32" and insert --(TGF)-$β_2$-- therefor On page 13, in Column 2, under "Other Publications", Line 24, delete "IFN-y" and insert --IFN-γ-- therefor On page 14, in Column 1, under "Other Publications", Line 2, delete "Hemostatis"," and insert --Hemostasis",-- therefor On page 14, in Column 1, under "Other Publications", Line 20, delete "Regneration" and insert --Regeneration-- therefor On page 14, in Column 1, under "Other Publications", Line 27, delete "cellbased" and insert --cell based-- therefor In the Claims In Column 26, Line 2, in Claim 11, delete "di electrophoretic" and insert --dielectrophoretic-- therefor